(12) United States Patent
MacKenzie et al.

(10) Patent No.: US 6,242,438 B1
(45) Date of Patent: *Jun. 5, 2001

(54) 3-AZETIDINYLALKYLPIPERIDINES OR -PYRROLIDINES AS TACHYKININ ANTAGONISTS

(75) Inventors: Alexander Roderick MacKenzie; Allan Patrick Marchington; Donald Stuart Middleton; Sandra Dora Meadows, all of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/297,736

(22) PCT Filed: Dec. 9, 1996

(86) PCT No.: PCT/EP96/05613

§ 371 Date: Jun. 1, 1998

§ 102(e) Date: Jun. 1, 1998

(87) PCT Pub. No.: WO97/25322

PCT Pub. Date: Jul. 17, 1997

(30) Foreign Application Priority Data

Jan. 5, 1996 (GB) .................................................. 9600235

(51) Int. Cl.⁷ ........................ A61K 31/445; C07D 401/06
(52) U.S. Cl. ........................ 514/210; 540/524; 540/544; 544/60; 544/62; 544/130; 544/141; 544/364; 544/372; 544/373; 546/187; 546/196; 546/201; 546/205; 546/208; 546/212; 546/216; 548/314.7; 548/455; 548/466; 548/467; 548/518; 548/950

(58) Field of Search .................................... 540/524, 544; 544/60, 62, 130, 141, 364, 372, 373; 546/187, 196, 201, 205, 208, 212, 216; 548/314.7, 455, 466, 467, 518, 950; 514/210

(56) References Cited

U.S. PATENT DOCUMENTS 5,340,822 * 8/1994 Emonds et al. ...................... 514/316
5,968,923 * 10/1999 MacKenzie et al. ................ 514/210

FOREIGN PATENT DOCUMENTS

| 0512901A1 | 4/1992 | (EP) . | |
| 962457 | * 8/1999 | (EP) . | |
| 992493 | * 4/2000 | (EP) . | |
| WO9605193 | 2/1996 | (WO) | ............................ C07P/401/06 |
| 97/27185 | * 7/1997 | (WO) . | |

* cited by examiner

Primary Examiner—Ceila Chang
(74) Attorney, Agent, or Firm—Peter C. Richardson; Paul H. Ginsburg; Jolene W. Appleman

(57) ABSTRACT

The present invention provides compounds of formula (I) and the pharmaceutically acceptable salts thereof. Such compounds and salts are tachykinin antagonists.

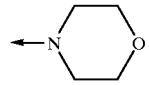

16 Claims, No Drawings

3-AZETIDINYLALKYLPIPERIDINES OR -PYRROLIDINES AS TACHYKININ ANTAGONISTS

This application is a 371 of PCT/EP96/05613 filed Dec. 9, 1996.

This invention relates to therapeutic agents, specifically azetidinylalkyl derivatives of N-substituted nitrogen heterocycles, and to processes for the preparation of, intermediates used in the preparation of, compositions containing and uses of, such heterocycles.

International Patent Publication Number WO 96/05193 discloses various (azetidin-1-ylalkyl)lactams as tachykinin antagonists.

The present heterocycles are antagonists of tachykinins, including neurokinin A (NKA), neurokinin B (NKB), and Substance P, acting at the human neurokinin-1 ($NK_1$), neurokinin-2 ($NK_2$) or neurokinin-3 ($NK_3$) receptor, or a combination of two or more thereof. The heterocycles are therefore useful for preventing or treating an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, a disease caused by *Helicobacter pylori* or other urease positive gram negative bacteria, a urogenital tract disorder such as incontinence, hyperreflexia, impotence or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as poison ivy, a vasospastic disease such as angina or Reynaud's disease, a proliferative disorder such as cancer or a disorder involving fibroblast proliferation, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Alzheimer's disease or multiple sclerosis, a disorder related to immune enhancement or suppression such as systemic lupus erythematosis, a rheumatic disease such as fibrositis, emesis, cough, acute or chronic pain, migraine, an opthalmic disease such as proliferative retinopathy, influenza or a cold.

The present derivatives are particularly potent and selective antagonists of tachykinins, including NKA, NKB and Substance P, acting at the human $NK_1$, $NK_2$ and $NK_3$ receptors or combinations of two or more thereof. They are particularly useful for treating or preventing an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, a urogenital tract disorder such as incontinence or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a bum, herpetic neuralgia or post-herpetic neuralgia, cough or acute or chronic pain.

The present invention provides compounds of the formula:

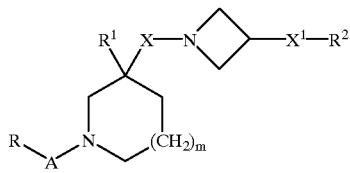

(I)

and the pharmaceutically acceptable salts thereof, wherein

R is $C_3$–$C_7$ cycloalkyl, aryl or $C_1$–$C_6$ alkyl, said $C_1$–$C_6$ alkyl being optionally substituted by fluoro, —COOH, —COO($C_1$–$C_4$) alkyl, $C_3$–$C_7$ cycloalkyl, adamantyl, aryl or $het^1$, and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro($C_1$–$C_4$) alkyl and fluoro ($C_1$–$C_4$)alkoxy;

A is CO or $SO_2$;

$R^1$ is phenyl, benzyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;

$R^2$ is —$CO_2H$, —$CONR^3R^4$, —$CONR^5(C_3$–$C_7$ cycloalkyl), —$NR^5(C_2$–$C_5$ alkanoyl), —$NR^3R^4$, —$NR^5CONR^5R^6$, ($C_3$–$C_7$ cycloalkyl-$C_1$–$C_4$ alkyl) $R^5N$—, ($C_3$–$C_7$ cycloalkyl-$C_1$–$C_4$ alkyl)$_2N$—, —$NR^5COCF_3$, —$NR^5SO_2CF_3$, —$NR^5(SO_2C_1$–$C_4$ alkyl), —$NR^5SO_2NR^5R^6$, —$NR^5(SO_2$ aryl), —N(aryl) ($SO_2C_1$–$C_4$ alkyl), —$OR^5$, —$O(C_3$–$C_7$cycloalkyl), —$SO_2NR^5R^6$, $het^3$ or a group of the formula:

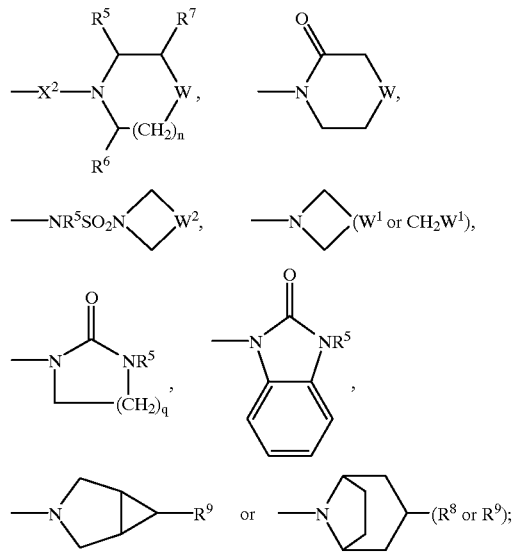

$R^3$ and $R^4$ are each independently selected from H and $C_1$–$C_4$ alkyl optionally substituted by hydroxy, $C_1$–$C_4$ alkoxy, —$S(O)_p(C_1$–$C_4$ alkyl), amino, —$NH(C_1$–$C_4$ alkyl), —$N(C_1$–$C_4$ alkyl)$_2$ or $het^2$;

$R^5$ and $R^6$ are each independently selected from H, $C_1$–$C_4$ alkyl and $C_3$–$C_7$ cycloalkyl-$C_1$–$C_4$ alkyl, said $C_1$–$C_4$ alkyl and $C_3$–$C_7$ cycloalkyl-$C_1$–$C_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro ($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5(SO_2C_1$–$C_4$ alkyl), —$NR^5SO_2NR_5R^6$, —$NR^5COO(C_1$–$C_4$ alkyl), —$NR^5CONR^5R^6$, —$NR^5(SO_2$morpholino), —$NR^5(SO_2$ aryl), —$N$(aryl)($SO_2C_1$–$C_4$ alkyl) or a group of the formula:

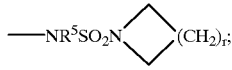

X is $C_1$–$C_4$ alkylene;

$X^1$ is a direct link or $C_1$–$C_6$ alkylene;

$X^2$ is a direct link, CO, $SO_2$ or $NR^5CO$;

W is methylene, CO, CH(OH), C(OH)$_2$, CH($C_1$–$C_4$ alkoxy), CHCO$_2$H, CHCO$_2$($C_1$–$C_4$ alkyl), CHCONR$^5$R$^6$, CHF, CF$_2$, CH(azetidin-1-yl), CH(pyrrolidin-1-yl), CH(piperidin-1-yl), CH(morpholino), CH(benzoxazol-2-yl), CHR$^9$, O, S(O)$_p$, NR$^5$, N(C$_3$–C$_7$ cycloalkyl), NSO$_2$(C$_1$–C$_4$ alkyl), NSO$_2$NR$^5$R$^6$, NSO$_2$CF$_3$, NSO$_2$(morpholino), NSO$_2$(aryl),

NCONR$^5$R$^6$, NCOR$^5$, NCO(aryl) or NCO$_2$(C$_1$–C$_4$ alkyl);

$W^1$ is methylene, CO, CH(OH), C(OH)$_2$, CH(C$_1$–C$_4$ alkoxy), CHCO$_2$H, CHCO$_2$(C$_1$–C$_4$ alkyl), CHCONR$^5$R$^6$, CHF, CF$_2$, CH(azetidin-1-yl), CH(pyrrolidin-1-yl), CH(piperidin-1-yl), CH(morpholino) or CHR$^9$;

$W^2$ is $W^1$, —CH$_2$W$^1$—, —CH$_2$WCH$_2$— or —CH$_2$CH$_2$WCH$_2$—;

m is 0, 1 or 2;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R^9$ and W, means naphthyl or phenyl, each optionally substituted by $C_1$–$C_4$ alkyl, halo, —$OR^5$, fluoro($C_1$–$C_4$)alkyl, $C_2$–$C_5$ alkanoyl, —$CONR^5R^6$, —$SO_2NR^5R^6$ or phenyl;

"het", used in the definition of R, means thienyl or a 5- or 6-membered ring heteroaryl group containing either 1 or 2 nitrogen heteroatoms or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro ($C_1$–$C_4$ alkyl) and fluoro($C_1$–$C_4$ alkoxy);

"het", used in the definitions of $R^3$ and $R^4$, means a 4- to 7-membered ring, non-aromatic, heterocyclic group containing 1 or 2 heteroatoms each independently selected from nitrogen, oxygen and S(O)$_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —$CONR^5R^6$ or —$SO_2NR^5R^6$ substituent;

and "het", used in the definition of $R^2$ means an optionally benzo-fused, N-linked, 5-membered ring heteroaryl group containing from 1 to 4 nitrogen heteroatoms, which is optionally substituted, including in the benzo-fused portion, by 1 or 2 substituents each independently selected from $C_1$–$C_4$ alkyl, fluoro and fluoro($C_1$–$C_4$) alkyl.

In the above definitions, the term "halo" means fluoro, chloro, bromo or iodo and alkyl, alkylene and alkoxy groups containing three or more carbon atoms and alkanoyl groups containing four or more carbon atoms can be straight- or branched-chain.

Preferably R is aryl, $C_3$–$C_7$ cycloalkyl optionally substituted by fluoro or $C_1$–$C_6$ alkyl substituted by $C_3$–$C_7$ cycloalkyl.

More preferably, R is phenyl optionally substituted by $C_1$–$C_4$ alkoxy, $C_3$–$C_7$ cycloalkyl optionally substituted by fluoro or $C_1$–$C_6$ alkyl substituted by $C_3$–$C_7$ cycloalkyl.

Most preferably R is phenyl, 2-methoxyphenyl, cyclopropyl, cyclohexyl, 4,4-difluorocyclohex-1-yl or cyclopropylmethyl.

Preferably, A is CO.

Preferably, $R^1$ is phenyl optionally substituted by 1 or 2 halo substituents.

More preferably, $R^1$ is phenyl optionally substituted by 1 or 2 substituents each independently selected from fluoro and chloro.

Yet more preferably, $R^1$ is phenyl, 3,4-difluorophenyl, 3-chlorophenyl, 4-chlorophenyl or 3,4-dichlorophenyl.

Most preferably, $R^1$ is 3,4-dichlorophenyl.

Preferably, $R^2$ is —$CONR^3R^4$, —$CONR^5(C_3$–$C_7$ cycloalkyl), —$NR^3R^4$, het$^3$ or a group of the formula:

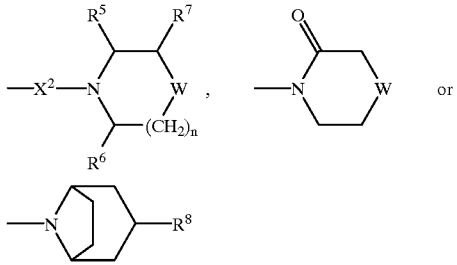

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CHF, CO, CH(C$_1$–C$_4$ alkoxy), CHCO$_2$H, CHCO$_2$(C$_1$–C$_4$ alkyl), CH(benzoxazol-2-yl), CHNR$^5$R$^6$, CHNR$^5$COR$^5$, CHNR$^5$(SO$_2$C$_1$–C$_4$ alkyl), CHNR$^5$COO(C$_1$–C$_4$ alkyl), O, S(O)$_p$, NR$^5$, NSO$_2$(C$_1$–C$_4$ alkyl), NSO$_2$NR$^5$R$^6$, NSO$_2$(morpholino), NCONR$^5$R$^6$, NCOR$^5$, NCO(aryl) or NCO$_2$(C$_1$–C$_4$ alkyl), n is 1 or 2 when W is other than methylene and is 0 or 1 when W is methylene, and p is 0, 1 or 2.

More preferably, $R^2$ is —$CONR^3R^4$, —$CONR^5(C_3$–$C_7$ cycloalkyl), —$NR^3R^4$, a N-linked, 5-membered ring heteroaryl group containing 1 or 2 nitrogen heteroatoms, or a group of the formula:

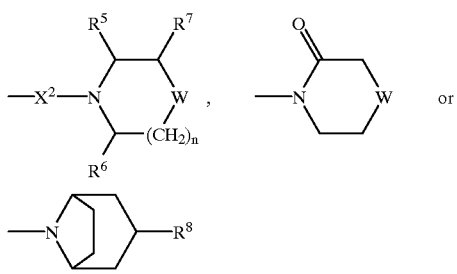

where $R^3$ and $R^4$ are each independently selected from methyl and $C_1$–$C_4$ alkyl substituted by hydroxy or methoxy, $R^5$ and $R^6$ are each independently selected from H, methyl, trifluoromethyl and cyclopropylmethyl, $R^7$ is H, hydroxy or phenyl, $R^8$ is hydroxy or acetyloxy, W is methylene, CH(OH), CHOCH$_3$, CHF, CO, CHOCH$_2$CH$_3$, CHO(CH$_2$)$_2$CH$_3$, CHOC(CH$_3$)$_3$, CHCO$_2$H, CHCO$_2$CH$_3$, CHCO$_2$CH$_2$CH$_3$, CH(benzoxazol-2-yl), CHNH$_2$, CHNHCH$_2$(cyclopropyl), CHNHCOCH$_3$, CHNHSO$_2$CH$_3$, CHNHCO$_2$C(CH$_3$)$_3$, O, S(O)$_p$, NH, NCH$_3$, NCH$_2$(cyclopropyl), NSO$_2$CH$_3$, NSO$_2$NH$_2$, NSO$_2$NHCH$_3$, NSO$_2$N(CH$_3$)$_2$, NSO$_2$(morpholino), NCONH$_2$, NCONHCH$_3$, NCOCH$_3$, NCOCF$_3$, NCO(phenyl) or NCO$_2$C(CH$_3$)$_3$, n is 1 or 2 when W is other than methylene and is 0 or 1 when W is methylene, and p is 0, 1 or 2.

Yet more preferably, $R^2$ is N-(2-methoxyethyl)-N-methylcarbamoyl, N-cyclohexylcarbamoyl, N-(2-hydroxyethyl)-N-methylamino, N-(2-hydroxy-2-methylpropyl)-N-methylamino, N-(2-methoxyethyl)-N-methylamino, imidazol-1-yl, 3-hydroxypyrrolidin-1-yl, piperidin-1-yl, 2,6-dimethylpiperidin-1-yl, 3-hydroxypiperidin-1-yl, 4-hydroxypiperidin-1-yl, 4-methoxypiperidin-1-yl, 4-ethoxypiperidin-1-yl, 4-(n-propoxy)piperidin-1-yl, 4-(t-butoxy)piperidin-1-yl, 4-carboxypiperidin-1-yl, 4-methoxycarbonylpiperidin-1-yl, 4-ethoxycarbonylpiperidin-1-yl, 4-(benzoxazol-2-yl)piperidin-1-yl, 4-aminopiperidin-1-yl, 4-cyclopropylmethylaminopiperidin-1-yl, 4-acetamidopiperidin-1-yl, 4-methanesulphonamidopiperidin-1-yl, 4-(t-butoxycarbonylamino)piperidin-1-yl, morpholino, 2-phenylmorpholino, homomorpholino, thiomorpholino, 1-oxothiomorpholino, 1,1-dioxothiomorpholino, piperazin-1-yl, 4-methylpiperazin-1-yl, 4-cyclopropylmethyl-piperazin-1-yl, 4-methanesulphonylpiperazin-1-yl, 4-aminosulphonylpiperazin-1-yl, 4-methyl-aminosulphonylpiperazin-1-yl, 4-dimethylamino-sulphonylpiperazin-1-yl, 4-morpholinosulphonylpiperazin-1-yl, 4-carbamoylpiperazin-1-yl, 4-N-methyl-carbamoylpiperazin-1-yl, 4-acetylpiperazir 1-yl, 4-trifluoroacetylpiperazin-1-yl, 4-benzoylpiperazin-1-yl, 4-(t-butoxycarbonyl)piperazin-1-yl, pyrrolidin-1-ylcarbonyl, piperidin-1-ylcarbonyl, 3-oxomorpholino, 3-hydroxy-8-azabicyclo[3,2,1]oct-8-yl, 3-acetyloxy-8-azabicyclo[3,2,1]oct-8-yl, 4-fluoropiperidin-1-yl or 4-oxopiperidin-1-yl.

Most preferably, $R^2$ is 4-aminopiperidin-1-yl, 4-carboxypiperidin-1-yl, 4-hydroxypiperidin-1-yl, morpholino, 1-oxothiomorpholino, 4-amino-sulphonylpiperazin-1-yl, 4-methanesulphonylpiperazin-1-yl, 4-methylaminosulphonylpiperazin-1-yl, 4-morpholinosulphonylpiperazin-1-yl, 4-fluoropiperidin-1-yl or 4-oxopiperidin-1-yl.

Preferably, X is ethylene or propylene.
Preferably, $X^1$ is a direct link.
Preferably, $X^2$ is a direct link.

Preferably, m is 0 or 1.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1–19 (1977).

A compound of the formula (I) may contain one or more asymmetric carbon atoms and may therefore exist in two or more stereoisomeric forms. The present invention includes the individual stereoisomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

The preferred compound of formula (I) and salts thereof have the stereochemistry shown below in formula (IA) at the position of attachment of the X and $R^1$ groups to the N-acylated or N-sulphonylated ring:

(IA)

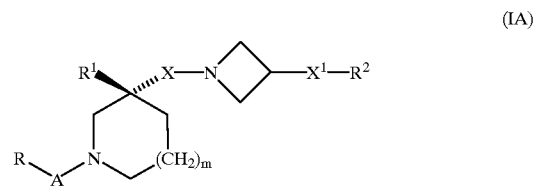

Preferred examples of a compound of formula (I) are those wherein:

(i) R is phenyl, A is CO, $R^1$ is 3,4-dichlorophenyl, $R^2$ is morpholino, X is propylene, $X^1$ is a direct link and m is 1;

(ii) R is phenyl, A is CO, $R^1$ is 3,4-dichlorophenyl, $R^2$ is 4-aminosulphonylpiperazin-1-yl, X is propylene, $X^1$ is a direct link and m is 1;

(iii) R is cyclohexyl, A is CO, $R^1$ is 3,4-dichlorophenyl, $R^2$ is morpholino, X is propylene, $X^1$ is a direct link and m is 1;

(iv) R is cyclohexyl, A is CO, $R^1$ is 3,4-dichlorophenyl, $R^2$ is 4-aminosulphonylpiperazin-1-yl, X is propylene, $X^1$ is a direct link and m is 1;

(v) R is cyclopropyl, A is CO, $R^1$ is 3,4-dichlorophenyl, $R^2$ is morpholino, X is propylene, $X^1$ is a direct link and m is 1;

(vi) R is cyclopropyl, A is CO, $R^1$ is 3,4-dichlorophenyl, $R^2$ is 4-aminosulphonylpiperazin-1-yl, X is propylene, $X^1$ is a direct link and m is 1;

(vii) R is phenyl, A is CO, $R^1$ is 3,4-dichlorophenyl, $R^2$ is morpholino, X is ethylene, $X^1$ is a direct link and m is 0;

(viii) R is 2-methoxyphenyl, A is CO, $R^1$ is 3,4-dichlorophenyl, $R^2$ is morpholino, X is ethylene, $X^1$ is a direct link and m is 0;

(ix) R is phenyl, A is CO, $R^1$ is 3,4-dichlorophenyl, $R^2$ is morpholino, X is ethylene, $X^1$ is a direct link and m is 1;

(x) R is 2-methoxyphenyl, A is CO, $R^1$ is 3,4-dichlorophenyl, $R^2$ is morpholino, X is ethylene, $X^1$ is a direct link and m is 1;

(xi) R is phenyl, A is $SO_2$, $R^1$ is 3,4-dichlorophenyl, $R^2$ is morpholino, X is ethylene, $X^1$ is a direct link and m is 1;

(xii) R is cyclopropylmethyl, A is CO, $R^1$ is 3,4-dichlorophenyl, $R^2$ is morpholino, X is ethylene, $X^1$ is a direct link and m is 1;

(xiii) R is cyclopropylmethyl, A is CO, $R^1$ is 3,4-dichlorophenyl, $R^2$ is 4-methanesulphonylpiperazin-1-yl, X is ethylene, $X^1$ is a direct link and m is 1;

or any such compound with the stereochemistry shown above in formula (IA) at the position of attachment of the X and $R^1$ groups to the N-acylated or N-sulphonylated ring, or a pharmaceutically acceptable salt of any thereof.

The compounds of the formula (I) provided by the invention can be prepared by the following methods:

1) The compounds of the formula (I) where X is $(C_0-C_3$ alkylene)$CH_2$—, the methylene group of which is attached to the azetidine nitrogen atom, and R, $R^1$, A, $R^2$, $X^1$ and m are as previously defined for a compound of the formula (I) can be prepared by reductive amination using as starting materials a compound of the formula:

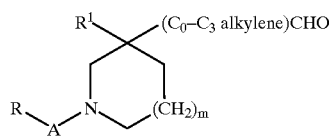
(II)

where R, A, $R_1$ and m are as previously defined for a compound of the formula (I), and a compound of the formula:

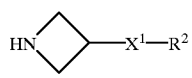
(III)

or an acid addition salt thereof, where $R^2$ and $X^1$ are as previously defined for a compound of the formula (I). The reaction is preferably carried out in the presence of a suitable acid, e.g. acetic acid.

The reaction proceeds via the initial formation of an intermediate iminium salt of the formula:

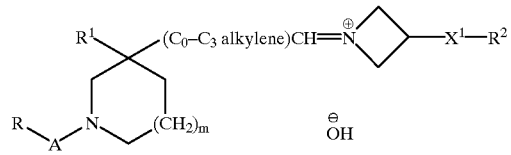
(IIIA)

which may stable and isolatable. The reaction is preferably carried out without isolation of the intermediate of the formula (IIIA) in which case it is reduced in situ to provide a compound of formula (I).

In a typical procedure, an aldehyde of the formula (II) is first reacted with an azetidine of the formula (III) in a suitable solvent, e.g. tetrahydrofuran, and the mixture then treated with a suitable reducing agent, e.g. sodium triacetoxyborohydride or sodium cyanoborohydride, in the presence of a suitable acid, e.g. acetic acid, to give the required product. If an acid addition salt of an azetidine of the formula (III) is used as a starting material, a suitable acid acceptor, e.g. triethylamine, can be added prior to the addition of the reducing agent.

The reaction is typically carried out at room temperature.

The starting aldehydes of the formula (II) can be prepared by the method shown in the Scheme I:

SCHEME I $R^1CH_2CN$ (IV)

1) Base
2) Z($C_0-C_3$ alkylene)$CH_2O$—[THP] (V)

↓

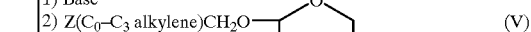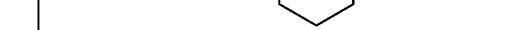 (VI)

1) Base
2) $Z^1CH_2(CH_2)_mCO_2(C_1-C_4$ alkyl) (VII)

↓

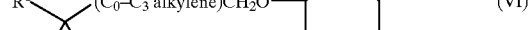 (VIII)

Reduction ↓

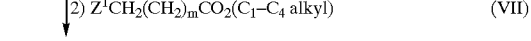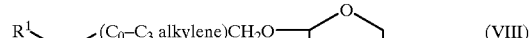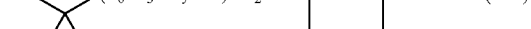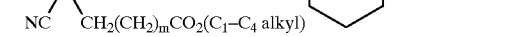 (IX)

Reduction ↓

-continued

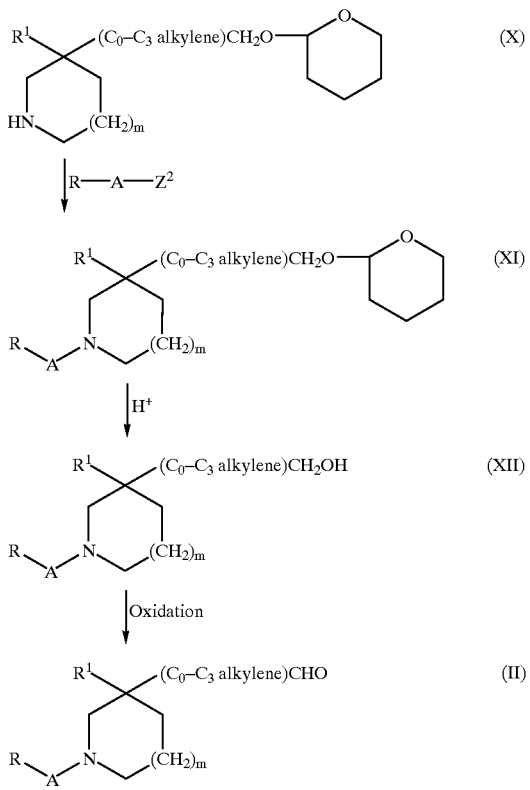

where R, A, $R^1$ and m are as previously defined for a compound of the formula (I) and Z and $Z^1$ are each a suitable leaving group, e.g. chloro, bromo, iodo, methanesulphonyloxy, p-toluenesulphonyloxy or trifluoromethylsulphonyloxy, and R—A—$Z^2$ is $RCO_2H$ or a derivative thereof suitable for acylation of amines, or $RSO_2Z^2$ suitable for sulphonylation of amines.

Examples of $Z^2$ include chloro, bromo and iodo.

In a typical procedure, the acetonitrile derivative of the formula (IV) is first deprotonated using a suitable base, e.g. sodium hydride, and then alkylated in situ with an alkylating agent of the formula (V) where Z is preferably bromo. The reaction is typically carried out in a suitable solvent, e.g. tetrahydrofuran, at about 0° C. for the deprotonation and at about room temperature for the alkylation. The reaction can also be carried out under phase transfer conditions using a suitable base, e.g. sodium hydroxide, a suitable phase transfer catalyst, e.g. tetra-n-butylammonium chloride, and a suitable solvent, e.g. cyclohexane, n-pentane or toluene.

The acetonitrile derivative of the formula (VI) that is produced is then first deprotonated using a suitable base, e.g. lithium diisopropylamide, and then alkylated in situ with a compound of the formula (VII) where $Z^1$ is preferably bromo. The reaction is typically carried out in a suitable solvent, e.g. tetrahydrofuran, at about –70° C., warming to about room temperature to complete the reaction. Tetra-n-butylammonium iodide can optionally be added following addition of the compound of the formula (VII) to increase the rate of reaction.

The compound of the formula (VIII) prepared is then reduced and cyclised to a lactam of the formula (IX) under suitable conditions, e.g. using Raney nickel under an atmosphere of hydrogen at atmospheric pressure and room temperature using ammoniacal ethanol as the solvent.

The lactam of formula (IX) is then reduced using a suitable reducing agent e.g. a metal hydride such as lithium aluminium hydride, under suitable conditions such as under an atmosphere of nitrogen, and in a suitable solvent such as tetrahydrofuran.

The cyclic amine (X) so produced is then reacted with $RSO_2Z^2$, or an acid or acid derivative $RCOZ^2$. In a typical procedure for A=CO, an acid chloride, RCOCl, is added to a mixture of a suitable base such as triethylamine, amine (X), and a suitable solvent such as dichloromethane. In a typical procedure for A=$SO_2$, a sulphonyl chloride, $RSO_2Cl$, is added to a mixture of a suitable base such as triethylamine, amine (X) and a suitable solvent such as dichloromethane.

The (sulphon)amide of the formula (XI) produced is then treated with a saturated solution of hydrogen chloride in a suitable $C_1$–$C_4$ alcohol, e.g. methanol, at about room temperature to remove the tetrahydropyran protecting group. The deprotection can also be carried out using a suitable ion exchange resin, e.g. Amberlyst 15 (trade mark), and in a suitable solvent, e.g. methanol.

The alcohol of the formula (XII) prepared is oxidised to an aldehyde of the formula (II) under suitable conditions, e.g. under Swern oxidation conditions (oxalyl chloride, dimethylsulphoxide, triethylamine, and using dichloromethane as the solvent).

An alternative method for the preparation of aldehyde of the formula (II) is illustrated in Scheme 2:

Scheme 2

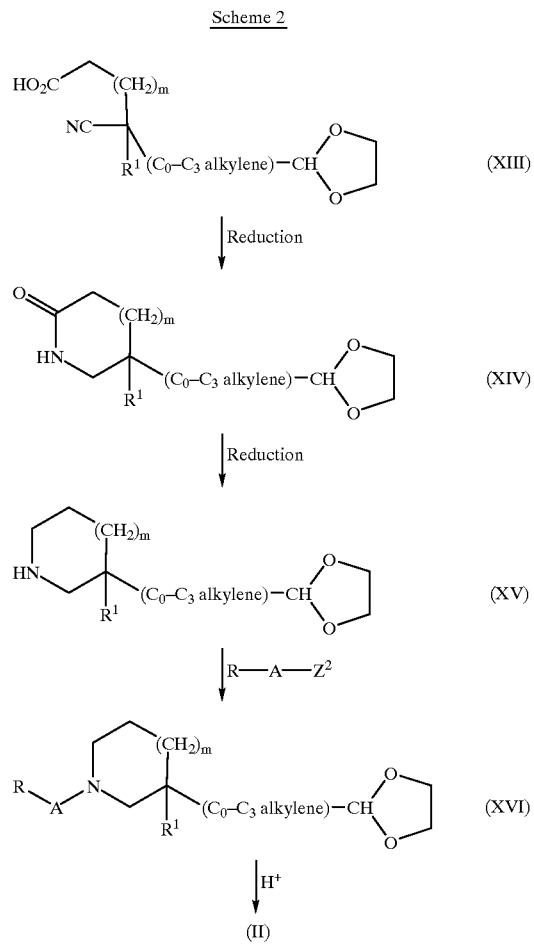

where R, A, $R^1$ and m are as previously defined for a compound of the formula (I) and R—A—$Z^2$ is as previously defined in reference to Scheme 1 above.

The starting cyano-acids of the formula (XIII) may be prepared by conventional methods.

In a typical procedure, the nitrile group of the cyano-acid of formula (XIII) is reduced and cyclised using a suitable system, for example catalytic hydrogenation. The reaction is typically carried out in a suitable solvent, e.g. glacial acetic acid, at room temperature and at elevated pressures, and over a suitable catalyst, such as platinum oxide.

The so produced lactam (XIV) is then reduced to the cyclic amine (XV). In a typical procedure, a solution of lactam (XIV) is added to a suitable reducing system such as lithium aluminium hydride, in a suitable solvent such as tetrahydrofuran.

The so produced cyclic amine (XV) is then reacted with R—A—$Z^2$ where R—A—$Z^2$ is as defined above in relation to Scheme 1. In a typical procedure for A=CO, amine (XV) and acid $RCO_2H$ are condensed to form amide (XVI; A=CO), using a coupling system such as N-methylmorpholine/1-hydroxybenzotriazole hydrate/1-(3-dimethylaminopropyl)-3-ethylcarbodiimide hydrochloride, in a suitable solvent, such as dichloromethane.

The (sulphon)amide (XVI) so produced is then treated with a suitable acid such as hydrochloric acid, in a suitable solvent e.g. tetrahydrofuran, at about room temperature, to remove the acetal protecting group. The deprotection can also be carried out using Amberlyst 15™ in a suitable solvent such as acetone/water. Other suitable deprotections for acetals are to be found in "Protective Groups in Organic Synthesis" by T W Greene and P G M Wuts (2nd edn., Wiley Interscience).

Yet another alternative method for the preparation of aldehydes of the formula (II) where m=1 is illustrated in Scheme 3:

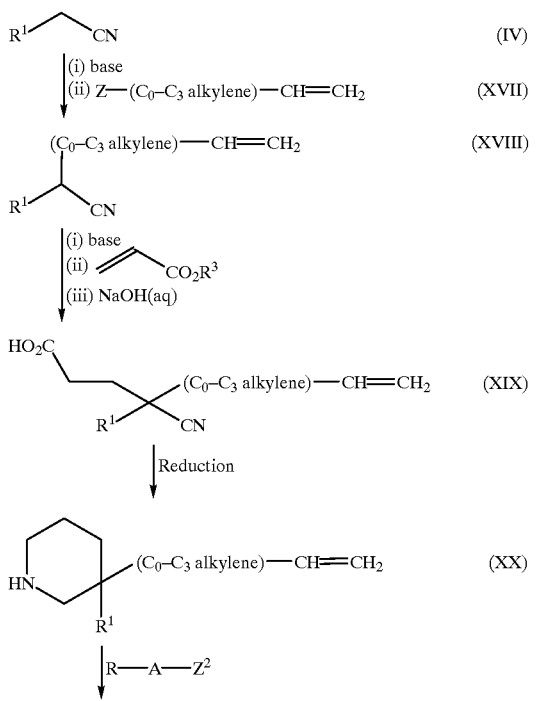

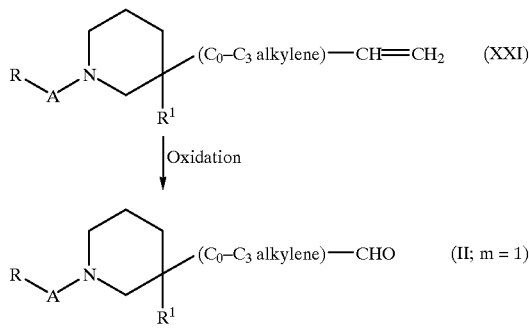

where $R^1$, $R^3$, Z, R, A and $Z^2$ are as previously defined.

In a typical procedure, a nitrile of formula (IV) is treated with a suitable base such as sodium hydride, then alkylated in situ with a compound of formula (XVII), where Z is as defined before. Compounds of formula (XVII) can be prepared by conventional methods. Z is preferably chloro, bromo, iodo or methanesulphonyloxy. The reaction is typically carried out in a suitable solvent such as N,N-dimethylformamide.

The so-prepared nitrile (XVIII) can then be deprotonated with a suitable base such as potassium t-butoxide, then reacted with a suitable acrylate ester, such as ethyl acrylate. The so-formed ester intermediate can then be hydrolysed to cyano-acid (XIX) using suitable hydrolysing systems such as 2N aqueous sodium hydroxide solution under suitable conditions such as stirring at room temperature.

The so-formed nitrile (XIX) can then be transformed by reduction using a suitable reducing agent, such as lithium aluminium hydride, in a suitable solvent such as tetrahydrofuran or by hydrogenation followed by reduction of the so-formed amide by borane.

The so-formed piperidine (XX) is then reacted in a similar manner as described for the transformations (X)→(XI) (Scheme 1) and (XV)→(XVI) (Scheme 2), above.

The amine derivative (XXI) so produced is then oxidised, such as, for example, by ozonolysis, in a suitable solvent such as methanol, followed by work up with a suitable reducing agent such as dimethyl sulphide, to give the aldehydes of formula II where m is 1.

The starting azetidines of the formula (III) may be prepared by conventional methods.

2) All the compounds of the formula (I), where X, A, $X^1$, $R^1$, $R^2$ and m are as previously defined for a compound of the formula (I), can be prepared by reaction of a compound of the formula (XXII):

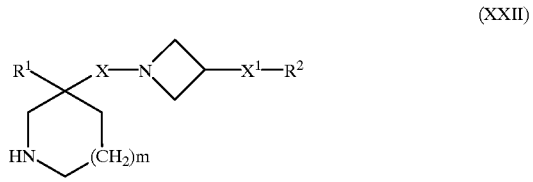

with a compound of the formula:

where R, A and $Z^2$ are as previously defined and the reactions are carried out in a similar manner to those described earlier for the transformation (X)→(XI) or, where A is CO, for (XV)→(XVI).

The starting materials of the formula (XXII) and R—A—$Z^2$ can be prepared by conventional methods such as by adaptation of the preparations described in "Advanced Organic Chemistry" by J. March (3rd edn., Wiley Interscience) and the references therein.

3) All the compounds of the formula (I) where X, $X^1$, R, A, $R^1$, $R^2$ and m are as previously defined for a compound of the formula (I) can be prepared by reaction of a compound of the formula:

(XXIII)

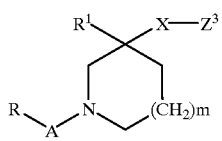

where X, R, A, $R^1$ and m are as previously defined for a compound of the formula (I) and $Z^3$ is a suitable leaving group, e.g. chloro, bromo, iodo, methanesulphonyloxy, trifluoromethanesulphonyloxy or p-toluenesulphonyloxy, with a compound of the formula:

(III)

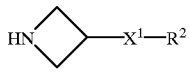

where $R^2$ and $X^1$ is as previously defined for a compound of the formula (I).

In a typical procedure, a compound of the formula (XXIII), where $Z^3$ is preferably methanesulphonyloxy, is reacted with a compound of the formula (III) in the presence of a suitable acid acceptor, e.g. triethylamine or potassium carbonate or a combination thereof, in a suitable solvent, e.g. acetonitrile, and at about the reflux temperature thereof.

The compound of the formula (III) can be prepared in situ from an acid addition salt thereof by using a molar excess of the acid acceptor.

The starting materials of the formula (XXIII) may be prepared by conventional methods such as by hydroxy functional group transformation of alcohols of the formula (XII), e.g. where $Z^3$ is methanesulphonyloxy, by reaction of an alcohol of the formula (XII) with methanesulphonyl chloride in the presence of a suitable acid receptor such as triethylamine.

4) The compounds of the formula (I) where $R^1$ is phenyl and X, $X^1$, R, A, $R^2$ and m are as previously defined for a compound of the formula (I) can be prepared by hydrogenolysis of a compound of the formula (I) where $R^1$ is phenyl substituted by chloro, bromo or iodo and X, $X^1$, R, $R^2$ and m are as previously defined for a compound of the formula (I).

In a typical procedure the hydrogenolysis is carried out in ammoniacal ethanol using a suitable catalyst, e.g. Raney nickel or, preferably, palladium-on-carbon, at about 50° C. and under an atmosphere of hydrogen at about 345 kPa (50 psi).

5) The compounds of the formula (I) where $R^2$ is a group of the formula: —$NHR^4$, ($C_3$–$C_7$ cycloalkyl-$C_1$–$C_4$ alkyl) HN—,

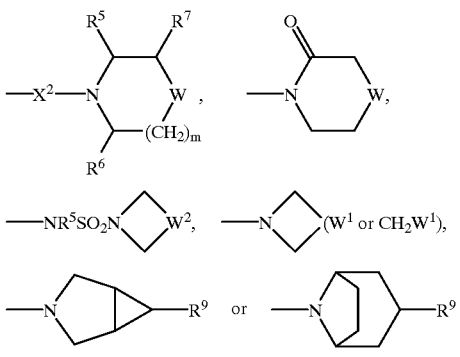

$R^9$ is —$NHR^5$, W is NH or $CHNHR^5$, $W^1$ is $CHNHR^5$, $W^2$ is $W^1$, —$CH_2W^1$—, —$CH_2WCH_2$— or —$CH_2CH_2WCH_2$—, and X, $X^1$, $X^2$, R, $R^1$, $R^5$, $R^6$, $R^7$, m and n are as previously defined for a compound of the formula (I), can be prepared by deprotection of a compound of the formula:

(XXIV)

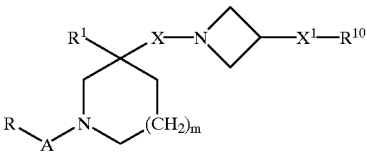

where $R^{10}$ is a group of the formula:

$NZ^4R^4$, ($C_3$–$C_7$ cycloalkyl-$C_1$–$C_4$ alkyl)$Z^4N$—,

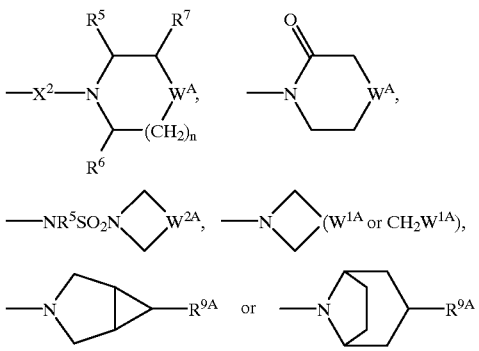

respectively, $R^{9A}$ is —$NZ^4R^5$, $W^A$ is $NZ^4$ or $CHNZ^4R^5$, $W^{1A}$ is $CHNZ^4R^5$, $W^{2A}$ is $W^{1A}$, —$CH_2W^{1A}$—, —$CH_2W^ACH_2$— or —$CH_2CH_2W^ACH_2$—, X, $X^1$, $X^2$, R, A, $R^1$, $R^4$, $R^5$, $R^6$, $R^7$, m and n are as previously defined for a compound of the formula (I) and $Z^4$ is a suitable protecting group, e.g. t-butoxycarbonyl (e.g. a compound of the formula (I) where W is $NCO_2C(CH_3)_3$ or $R^9$ is —$NR^5CO_2C(CH_3)_3$) or benzyloxycarbonyl.

Suitable protecting groups that may be used in this Method, together with methods for deprotection, are well known to the skilled person, e.g. see Greene et al, "Protective Groups in Organic Synthesis", Second Edition, 1991, Wiley-Interscience.

In a typical procedure where $Z^4$ is t-butoxycarbonyl, the deprotection can be carried out using trifluoroacetic acid in a suitable solvent, e.g. dichloromethane, at room temperature.

The starting materials of the formula (XXIV) can be prepared by conventional methods such as by appropriate adaptation of the Methods described herein for preparing the compounds of the formula (I).

6) The compounds of the formula (I) where $R^2$ is a group of the formula:

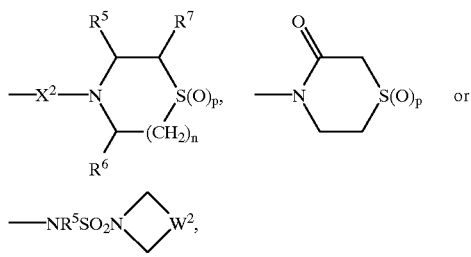

where p is 1 or 2, $W^2$ is —$CH_2S(O)_pCH_2$— or —$CH_2CH_2S(O)_pCH_2$— and X, $X^1$, $X^2$, R, A, $R^1$, $R^5$, $R^6$, $R^7$, m and n are as previously defined for a compound of the formula (I) can be prepared by oxidation of a compound of the formula (I) where $R^2$ is a group of the formula:

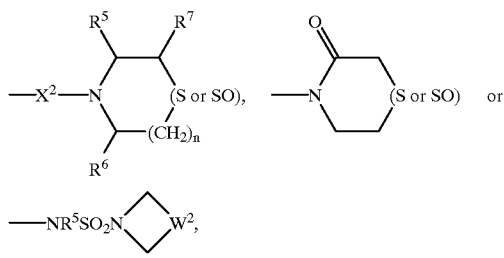

as appropriate, wherein $W^2$ is —$CH_2$(S or SO)$CH_2$— or —$CH_2CH_2$(S or SO)$CH_2$—, and X, $X^1$, $X^2$, R, A, $R^1$, $R^5$, $R^6$, $R^7$, m and n are as previously defined for a compound of the formula (I). The oxidation is carried out with at least one molar equivalent of a suitable oxidising agent when converting a sulphoxide to a sulphone, at least two molar equivalents of a suitable oxidising agent when converting a sulphide to a sulphone and substantially one molar equivalent of a suitable oxidising agent for the conversion of a sulphide to a sulphoxide.

Suitable oxidising agents and conditions for this purpose are aqueous hydrogen peroxide solution under basic conditions (e.g. in the presence of potassium carbonate, acetonitrile and using methanol as the solvent) or m-chloroperbenzoic acid in a suitable solvent, e.g. dichloromethane.

7) The compounds of the formula (I) where $R^2$ is a group of the formula:

and X, $X^1$, R, A, $R^1$ and m are as previously defined for a compound of the formula (I), can be prepared by deprotection of a compound of the formula:

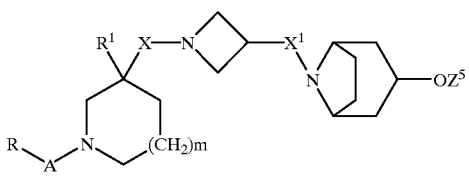
(XXV)

where $Z^5$ is a suitable protecting group, e.g. acetyl (i.e. a compound of the formula (I) where $R^8$ is acetyloxy) or tetrahydropyran-2-yl, and X, $X^1$, R, A, $R^1$ and m are as previously defined for a compound of the formula (I).

Suitable protecting groups that may be used for this Method, together with methods for deprotection, are well known to the skilled person, e.g. see Greene et al, "Protective Groups in Organic Synthesis", Second Edition, 1991, Wiley-Interscience.

In a typical procedure where $Z^5$ is acetyl the deprotection can be carried out using an aqueous alcoholic solution of a suitable strong base, e.g. sodium hydroxide. The reaction is typically carried out in aqueous methanol at about room temperature.

The starting materials of the formula (XXV) can be prepared by conventional methods such as by adaptation of the Methods described herein for preparing the compounds of the formula (I).

8) The compounds of the formula (I) where $X^1$ is a direct link and $R^2$ is —$NR^3R^4$, ($C_3$–$C_7$ cycloalkyl-$C_1$–$C_4$ alkyl)$R^5N$—, ($C_3$–$C_7$ cycloalkyl-$C_1$–$C_4$ alkyl)$_2N$—, or is a group of the formula:

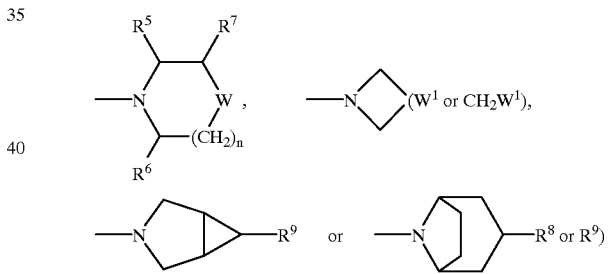

and X, W, $W^1$, R, A, $R^1$, $R^3$, $R^4$, $R^5$, $R^6$, $R^7$, $R^8$, $R^9$, m and n are as previously defined for a compound of the formula (I), can be prepared by reaction of a compound of the formula:

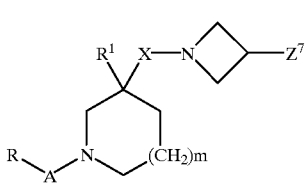
(XXVI)

where X, R, A, $R^1$ and m are as previously defined for a compound of the formula (I) and $Z^7$ is a suitable leaving group, e.g. methanesulphonyloxy or p-toluenesulphonyloxy, with a compound of the formula:

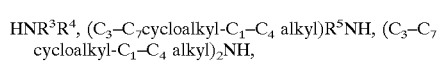

17

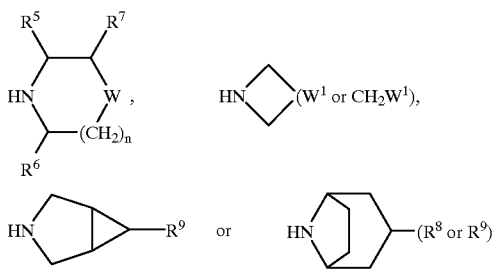

respectively, where W, W$^1$, R$^3$, R$^4$, R$^5$, R$^6$, R$^7$, R$^8$, R$^9$ and n are as previously defined for a compound of the formula (I).

In a typical procedure, the reaction is carried out using an excess of the amine and in a suitable solvent, e.g. acetonitrile or dichloromethane, and at the reflux temperature of the solvent. Alternatively, a further suitable acid acceptor, e.g. potassium carbonate, can be added to the reaction mixture.

The starting amines can be prepared by conventional methods.

The starting materials of the formula (XXVI) can also be prepared by conventional methods such as by reductive amination using as starting materials a compound of the formula (II) and ammonia to prepare the corresponding primary amine, reaction of the amine with epichlorohydrin or 1,3-dichloropropan-2-ol to prepare the corresponding azetidin-3-ol derivative, followed by hydroxy functional group interconversion to provide a compound of the formula (XXVI).

9) The compounds of the formula (I) where X, X$^1$, R, A, R$^1$, R$^2$ and m are as previously defined for Method (8) can be prepared by reductive amination using as starting materials a compound of the formula:

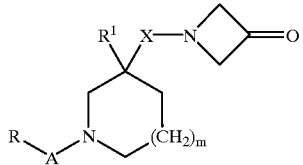

(XXVII)

where X, R, A, R$^1$ and m are as previously defined for a compound of the formula (I), and a compound of the formula:

HNR$^3$R$^4$, (C$_3$–C$_7$ cycloalkyl-C$_1$–C$_4$ alkyl)R$^5$NH, (C$_3$–C$_7$ cycloalkyl-C$_1$–C$_4$ alkyl)$_2$NH,

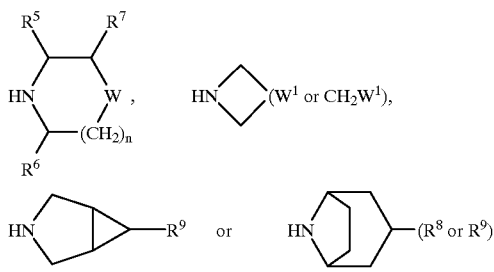

as appropriate, or an acid addition salt thereof, where W, W$^1$, R$^3$, R$^4$, R$^5$, R$^6$, R$^7$, R$^8$, R$^9$ and n are as previously defined for a compound of the formula (I). The reaction is preferably carried out in the presence of a suitable acid, e.g. acetic acid.

18

A typical procedure that can be followed is described in Method (1).

If a primary amine is used, the reaction proceeds via an imine intermediate. If a secondary amine is used, the reaction proceeds via an intermediate iminium salt (cf. a compound of the formula (IIIA)). Both the imine and iminium salts may be stable and isolatable. The reaction is preferably carried out without isolation of the imine or iminium salt intermediate in which case it is reduced in situ to provide a compound of the formula (I).

The starting materials of the formula (XXVII) can be prepared by oxidation of the corresponding azetidin-3-ol derivatives (preparation described in the preparation of the starting materials for Method (8) under conventional conditions, e.g. using pyridinium chlorochromate or tetrapropylammonium perruthenate as the oxidising agent.

10) The compounds of the formula (I) where R$^2$ is morpholino and X, X$^1$, R, A, R$^1$ and m are as previously defined for a compound of the formula (I), can be prepared by reaction of a compound of the formula (I) where R$^2$ is —NH$_2$ and X, X$^1$, R, A, R$^1$ and m are as previously defined for a compound of the formula (I), with bis(2-chloroethyl) ether.

In a typical procedure, a compound of the formula (I) where R$^2$ is —NH$_2$ is reacted with bis(2-chloroethyl)ether in the presence of a suitable acid acceptor, e.g. triethylamine, and in a suitable solvent, e.g. dichloromethane.

Certain of the starting amine derivatives, i.e. 3-aminoazetidine derivatives, can be prepared by reacting a compound of the formula (XXVI) where Z$^7$ is a suitable leaving group, e.g., methanesulphonyloxy, with a suitable azide, e.g. sodium azide or trimethylsilyl azide, to provide the corresponding 3-azidoazetidine derivative, followed by reduction thereof, e.g. using sodium borohydride, to provide the required 3-aminoazetidine derivative (see also Method (8)).

11) Certain compounds of the formula (I) can be prepared by derivatisation of certain amines of the formula (I). For example, a compound of the formula (I) wherein R$^2$ is

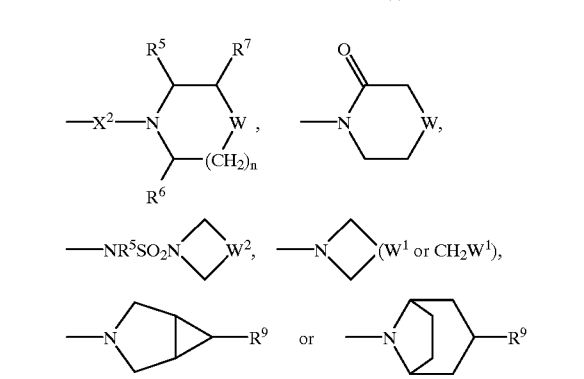

wherein W is NH or CHNHR$^5$, W$^1$ is CHNHR$^5$, W$^2$ is W$^1$, —CH$_2$W$^1$—, —CH$_2$WCH$_2$— or —CH$_2$CH$_2$WCH$_2$—, or R$^9$ is —NHR$^5$ and X, X$^1$, X$^2$, R, A, R$^1$, R$^5$, R$^6$, R$^7$, m and n are as previously defined for a compound of the formula (I), may be converted to (a) a compound of the formula (I) wherein W is NR$^5$ or CHNR$^5$R$^6$, W$^1$ is CHNR$^5$R$^6$ or R$^9$ is —NHR$^5$, or an acid addition salt thereof, as appropriate, wherein R$^5$ and R$^6$ are as previously defined for a compound of the formula (I) with the provisos that R$^5$ is not H and it has a methylene group bonded to the nitrogen atom, by reductive amination with an aldehyde of the formula ($C_1$–$C_3$ alkyl)CHO or ($C_3$–$C_7$ cycloalkyl-$C_1$–$C_3$ alkyl) CHO, said $C_1$–$C_3$ alkyl and $C_3$–$C_7$ cycloalkyl-$C_1$–$C_3$ alkyl being optionally substituted by fluoro.

Suitable conditions for this conversion are described in Method (1);

(b) a compound of the formula (I) wherein W is NCONHR$^6$ or CHNR$^5$CONHR$^6$, W$^1$ is CHNR$^5$CONHR$^6$ or R$^9$ is —NR$^5$CONHR$^6$, as appropriate, wherein R$^5$ and R$^6$ are as previously defined for a compound of the formula (I) with the proviso that R$^6$ is not H, by reaction with an isocyanate of the formula:

R$^6$NCO wherein R$^6$ is as previously defined for this Method. The reaction is typically carried out using a suitable solvent, e.g. dichloromethane or tetrahydrofuran;

(c) a compound of the formula (I) wherein W is NSO$_2$CF$_3$ or CHNR$^5$SO$_2$CF$_3$, W$^1$ is CHNR$^5$SO$_2$CF$_3$ or R$^9$ is —NR$^5$SO$_2$CF$_3$, as appropriate, wherein R$^5$ is as previously defined for a compound of the formula (I), by reaction with trifluoromethanesulphonyl chloride or trifluoromethanesulphonic anhydride, optionally in the presence of a suitable acid acceptor, e.g. triethylamine, pyridine or potassium carbonate. The reaction is typically carried out in a suitable organic solvent, e.g. dichloromethane or acetonitrile;

(d) a compound of the formula (I) wherein W is NSO$_2$($C_1$–$C_4$ alkyl) NSO$_2$NR$^5$R$^6$, NSO$_2$ (morpholino), NSO$_2$(aryl) CHNR$^5$(SO$_2$ $C_1$–$C_4$ alkyl) or CHNR$^5$SO$_2$NR$^5$R$^6$, W$^1$ is CHNR$^5$(SO$_2$ $C_1$–$C_4$ alkyl) or CHNR$^5$SO$_2$NR$^5$R$^6$, or R$^9$ is —NR$^5$(SO$_2$ $C_1$–$C_4$ alkyl) or —NR$^5$SO$_2$NR$^5$R$^6$, as appropriate, wherein R$^5$ and R$^6$ are as previously defined for the formula (I), by reaction with a $C_1$–$C_4$ alkanesulphonyl chloride or bromide, a $C_1$–$C_4$ alkanesulphonic anhydride or a compound of the formula: R$^5$R$^6$NSO$_2$(Cl or Br), (morpholino)SO$_2$(Cl or Br) or (aryl)SO$_2$(Cl or Br), as appropriate, optionally in the presence of a suitable acid acceptor, e.g. triethylamine. The reaction is typically carried out in a suitable organic solvent, e.g. dichloromethane, at from 0° C. to room temperature;

(e) a compound of the formula (I) wherein W is NCQR$^6$ or CHNR$^5$COR$^6$, W$^1$ is CHNR$^5$COR$^6$ or R$^9$ is —NR$^5$COR$^6$, as appropriate, wherein R$^5$ and R$^6$ are as previously defined for a compound of the formula (i) with the proviso that R$^6$ is not H, by reaction with a compound of the formula:

R$^6$CO(Cl or Br) or (R$^6$CO)$_2$O wherein R$^6$ is as previously defined for this Method, optionally in the presence of a suitable acid acceptor, e.g. triethylamine. The reaction is typically carried out in a suitable organic solvent, e.g. dichloromethane, at from 0° C. to room temperature;

(f) a compound of the formula (I) wherein W, W$^1$ or R$^9$ is as previously defined for Method 12(e), as appropriate, by condensation with a compound of the formula:

R$^6$CO$_2$H wherein R$^6$ is as previously defined for this Method. The reaction can be performed under conventional conditions, e.g. using 1,1'-carbonyl-diimidazole or 1-hydroxybenzotriazole/1,3-dicyclohexylcarbodiimide to generate activated intermediates; or (g) a compound of the formula (I) where W is NSO$_2$NR$^5$R$^6$ or CHNR$^5$SO$_2$NR$^5$R$^6$, W$^1$ is CHNR$^5$SO$_2$NR$^5$R$^9$ or R$^9$ is —NR$^5$SO$_2$NR$^5$R$^6$, as appropriate, wherein R$^5$ and R$^6$ are as previously defined for a compound of the formula (I), by reaction with a compound of the formula:

R$^5$R$^6$NSO$_2$NH$_2$

The reaction is typically carried out at an elevated temperature in a suitable solvent, e.g. 1,4-dioxane.

12) The compounds of the formula (I) wherein R$^2$ is:

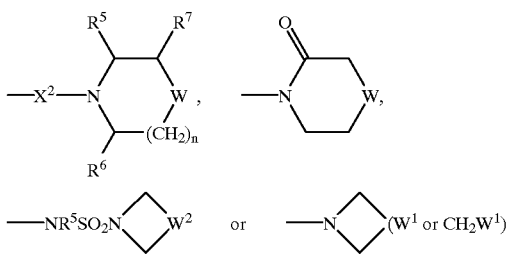

wherein W and W$^1$ are CHCO$_2$H and W$^2$ is W$^1$, —CH$_2$W$^1$—, —CH$_2$WCH$_2$— or —CH$_2$CH$_2$WCH$_2$— and X, X$^1$, X$^2$, A, R, R$^1$, R$^2$, R$^5$, R$^6$, R$^7$, m and n are as previously defined for a compound of the formula (I), may be prepared by hydrolysis of a compound of the formula (I) wherein W and W$^1$ are CHCO$_2$($C_1$–$C_4$ alkyl), W$^2$ is W$^1$, —CH$_2$W$^1$—, —CH$_2$WCH$_2$— or —CH$_2$CH$_2$WCH$_2$— and X, X$^1$, X$^2$, A, R, R$^1$, R$^2$, R$^5$, R$^6$, R$^7$, m and n are as previously defined for a compound of the formula (I). Preferably, W and W$^1$ are CHCO$_2$CH$_3$ or CH$_2$CO$_2$CH$_2$CH$_3$.

The hydrolysis is typically carried out using an aqueous solution of a suitable acid or base, e.g. a mineral acid such as hydrochloric or sulphuric acid or a base such as sodium or potassium hydroxide, optionally in the presence of a suitable organic co-solvent, e.g. methanol or ethanol.

13) The compounds of the formula (I) wherein R$^2$ is

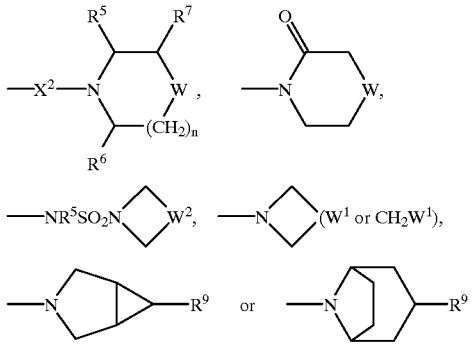

wherein W and W$^1$ are CHNR$^5$R$^6$, W$^2$ is W$^1{}_1$, —CH$_2$W$^1$—, —CH$_2$WCH$_2$— or —CH$_2$CH$_2$WCH$_2$—, R$^9$ is —NR$^5$R$^6$ and X, X$^1$, X$^2$, A, R, R$^1$, R$^2$, R$^5$, R$^6$, R$^7$, m and n are as previously defined for a compound of the formula (I) may be prepared by reaction of a compound of the formula:

(XXVIII)

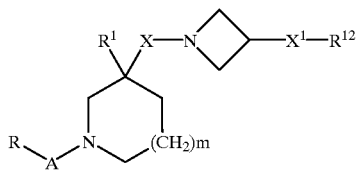

wherein $R^{12}$ is

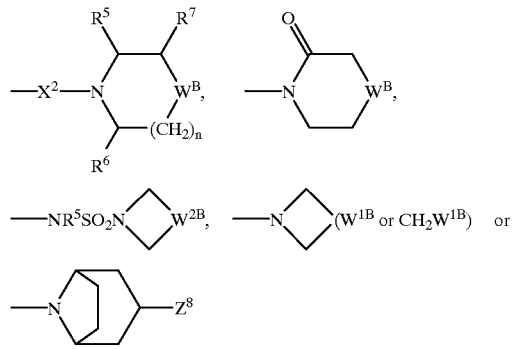

wherein $W^B$ and $W^{1B}$ are $CHZ^8$, $W^{2B}$ is $W^{1B}$, $—CH_2W^{1B}—$, $—CH_2W^BCH_2—$ or $—CH_2CH_2W^BCH_2—$, $Z^8$ is a suitable leaving group, e.g. halo, (preferably chloro or bromo), methanesulphonyloxy, trifluoromethanesulphonyloxy or p-toluenesulphonyloxy, and X, $X^1$, $X^2$, R, A, $R^1$, $R^5$, $R^6$, $R^7$, m and n are as previously defined for a compound of the formula (I), with a compound of the formula:

$HNR^5R^6$ wherein $R^5$ and $R^6$ are as previously defined for a compound of the formula (I), optionally in the presence of a suitable additional acid acceptor, e.g. triethylamine or potassium carbonate.

The reaction is typically carried out in a suitable solvent such as acetonitrile.

14) The compounds of the formula (I) wherein $R^2$ is

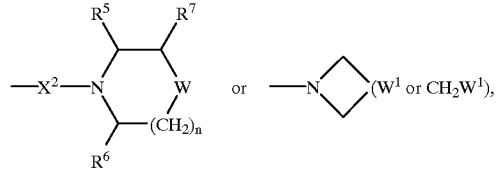

W and $W^1$ are $CHNR^5R^6$ and X, $X^1$, $X^2$, R, A, $R^1$, $R^5$, $R^6$, $R^7$, m and n are previously defined for a compound of the formula (I), may be prepared by reductive amination using as the starting materials a compound of the formula (I):

wherein $R^2$ is

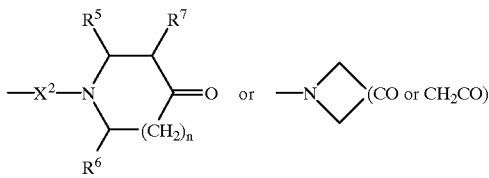

and X, $X^1$, $X^2$, R, A, $R^1$, $R^5$, $R^6$, $R^7$, m and n are as previously defined for a compound of the formula (I), and a compound of the formula:

$HNR^5R^6$ wherein $R^5$ and $R^6$ are as previously defined for a compound of the formula (I).

Conventional conditions are used such as those described for Method (1). Again, the intermediate imine or iminium salt formed may be stable or isolatable. The reaction is preferably carried out without isolation of this intermediate in which case it is reduced in situ to provide a compound of the formula (I).

15) All the compounds of the formula (I) may be prepared by intramolecular cyclisation of a compound of the formula:

(XXIX)

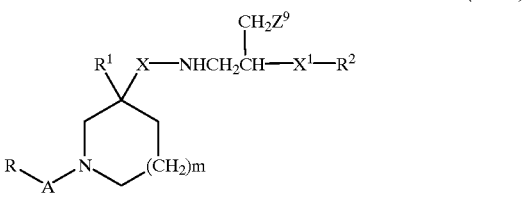

wherein X, $X^1$, R, A, $R^1$, $R^2$ and m are as previously defined for a compound of the formula (I) and $Z^9$ is a suitable leaving group, e.g. halo (preferably chloro or bromo), methanesulphonyloxy or p-toluenesulphonyloxy, optionally in the presence of a suitable acid acceptor, e.g. triethylamine.

The reaction is typically carried out in a suitable solvent, e.g. dichloromethane.

16) Compounds of the formula (I) where A is CO may be prepared by intramolecular cyclisation of a compound of the formula (XXX):

(XXX)

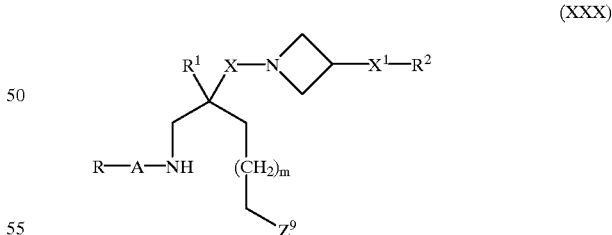

wherein X, $X^1$, R, A, $R^1$, $R^2$ and m are as previously defined for a compound of formula (I), and $Z^9$ is as defined above for method 15 and the reaction is carried out by treatment with a suitable base such as n-butyllithium.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of formula (I) and their salts for the human $NK_1$ receptor can be tested in vitro by testing their ability to inhibit [$^3$H]–Substance P binding to membranes prepared from the human IM9 cell line expressing the human $NK_1$ receptor using a modification of the method described in McLean, S. et al, J. Pharm. Exp. Ther., 267, 472–9 (1993) in which whole cells were used.

The affinity of the compounds of formula (I) and their salts for the human $NK_2$ receptor can be tested in vitro by testing their ability to compete with [3H] or [$^{125}$I]NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [$^{125}$I]NKA and with a range of concentrations of the test compound. Non-specific binding was determined in the presence of 10 μM NKA.

The $NK_2$ receptor antagonist activity of the compounds of the formula (I) can be tested, in vitro, by testing their ability to antagonise the contractile effects of the selective $NK_2$ receptor agonist [βAla$^8$]NKA$_{(4-10)}$ in the rabbit pulmonary artery, using the method of Patacchini and Maggi, Eur. J. Pharmacol., 236, 31–37 (1993).

The compounds of the formula (I) and their salts can be tested for $NK_2$ receptor antagonist activity, in vivo, by testing their ability to inhibit bronchoconstriction induced by [βAla$^8$]NKA$_{(4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for $NK_3$ receptor antagonist activity, in vitro, by testing their ability to antagonise the contractile effects of the selective $NK_3$ receptor agonist senktide in the guinea-pig ileum using the method of Maggi et al, Br. J. Pharmacol., 101, 996–1000 (1 990).

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.1 to 1 0, and most preferably from 0.5 to 5, mg/kg (in single or divided doses). Thus tablets or capsules of the compounds will contain from 0.1 to 500, preferably from 50 to 200, mg of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect on a tachykinin acting at the human $NK_1$, $NK_2$ or $NK_3$ receptor, or a combination of two or more thereof;

iv) use as in (iii) where the disease is an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a bum, herpetic neuralgia or post-herpetic neuralgia, cough or acute or chronic pain;

v) a method of treatment of a human to treat a disease by producing an antagonist effect on a tachykinin acting at the human $NK_1$, $NK_2$ or $NK_3$ receptor, or a combination of two or more thereof, which comprises treating said human with an effective amount of a compound of the formula (I) or with a pharmaceutically acceptable salt or composition thereof;

vi) a method as in (v) where the disease is an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a bum, herpetic neuralgia or post-herpetic neuralgia, cough or acute or chronic pain;

vii) a compound of the formula (II), (IIIA), (XXII), (XXIII), (XXIV), (XXV), (XXVI), (XXVII), (XXVIII), (XXIX) or (XXX).

The following Examples illustrate the preparation of the compounds of the formula (I):

EXAMPLE 1

1-Benzoyl-3-(3,4-dichlorophenyl)-3-(3-[3-morpholinoazetidin-1-yl]propyl)piperidine

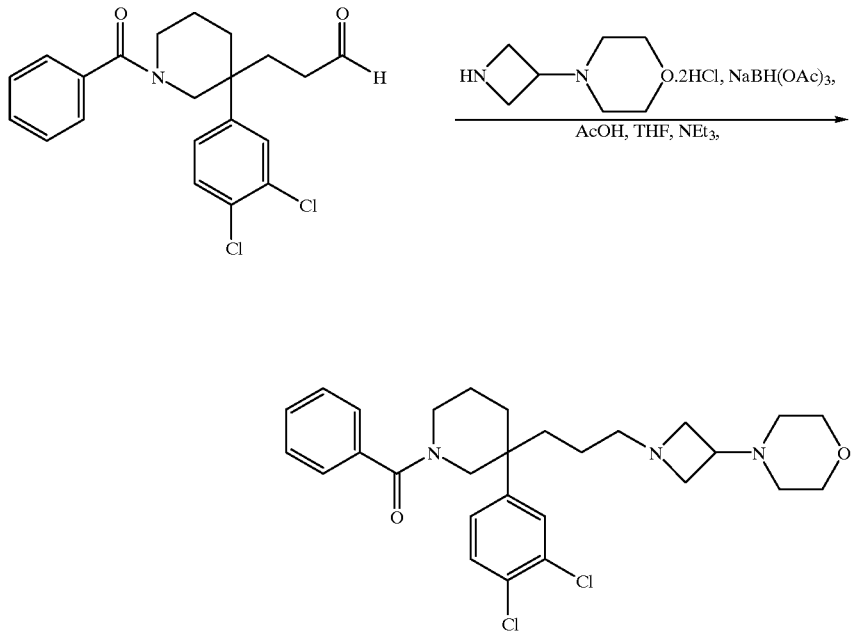

To a solution of the aldehyde (see PREPARATION 7) (0.48 g, 1.23 mmol.) and 3-morpholinoazetidine dihydrochloride (see PREPARATION 13) (0.291 g, 1.1 mol. equiv.) in tetrahydrofuran (20 ml) under nitrogen was added triethylamine (0.38 ml, 2.2 mol. equiv.). After thirty minutes, sodium triacetoxyborohydride (0.391 g, 1.5 mol. equiv.) was added, followed immediately by glacial acetic acid (0.07 ml) and the mixture was stirred for eighteen hours. The solvent was removed under reduced pressure and the residue was partitioned between 10% aqueous potassium carbonate solution (20 ml) and ethyl acetate (20 ml). The aqueous phase was then extracted again with ethyl acetate (2×20 ml) and the combined organics dried over sodium sulphate. The solution was then filtered and the solvent was removed under reduced pressure. The residue was then chromatographed using silica gel, eluting with dichloromethane:methanol (9:1 by volume to give, the title compound (166 mg). TLC $R_f$=0.25 (silica, dichloromethane:methanol, 9:1 by volume). LRMS m/z= 516 (m+1)$^+$. Found C, 61.07; H, 6.18; N, 8.04. $C_{28}H_{35}N_3O_2Cl_2 \cdot 0.5CH_2Cl_2$ requires C, 61.23; H, 4.49; N, 7.52%.

$^1$H-NMR (CDCl$_3$): δ=0.95–1.1 (m), 1.2–1.5 (m), 1.55–1.9 (m), 2.0–2.1 (m), 2.25–2.3 (m), 2.4–2.6 (m), 2.9–3.0 (m), 3.25–3.4 (m), 3.6–3.7 (m), 7.2–7.4 (m).

EXAMPLES 2–8

The compounds of the following tabulated preparations of the general formula:

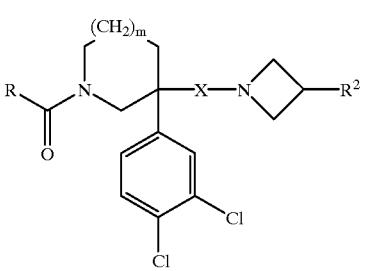

were prepared by a similar method to that used in EXAMPLE 1 using the appropriate aldehyde (see PREPARATIONS 7,6,9,36 and 37) and either 3-morpholinoazetidine dihydrochloride (PREPARATION 13) or 3-(4-aminosulphonylpiperazin-1-yl)azetidine bistrifluoroacetate (PREPARATION 16).

| Ex. no. | m | X | R | R² | LRMS m/z | Analysis/¹H-NMR |
|---|---|---|---|---|---|---|
| 2 | 1 | (CH₂)₃ | 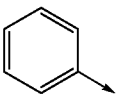 | 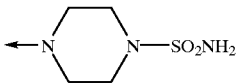 | 515 (m-SO₂—NH₂)⁺ | ¹H-NMR (CDCl₃): δ = 1.6–1.9 (m,5H), 2.1–2.2 (m,1H), 2.25–2.45 (m,7H), 2.7–2.8 (m,2H), 2.9–3.0 (m,1H), 3.2–3.3 (m,7H), 3.35–3.5 (m,6H), 4.3–4.4 (m,1H), 7.25–7.5 (m,8H). Found: C, 53.26; H, 6.03; N, 10.69.C₂₈H₃₇N₅O₃Cl₂.S.0.5CH₂Cl₂. 0.0313.CH₃CO₂C₂H₅ requires C, 53.73; H 6.03; N, 10.95. |
| 3 | 1 | (CH₂)₃ | 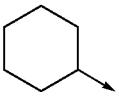 | 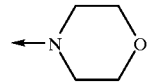 | 522 (m + 1)⁺ | ¹H-NMR (CDCl₃): δ = 1.1–1.85 (m,16H), 2.0–2.1 (m,1H), 2.2–2.5 (m,8H), 2.8–3.05 (m,3H), 3.15–3.3 (m,2H), 3.4–3.6 (m,4H), 3.65–3.7 (m,4H), 7.1–7.2 (m,1H), 7.3–7.4 (m,2H). Found: C, 61.81; H, 7.92; N, 7.82; C₂₈H₄₁N₃O₂Cl₂.0.25CH₂Cl₂ requires C, 62.39; H, 7.69; N, 7.73. |
| 4 | 1 | (CH₂)₃ | 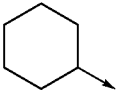 | 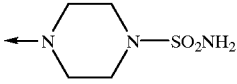 | 600 (m + 1)⁺ | ¹H-NMR (CDCl₃): δ = 1.2–1.9 (m), 1.95–2.05 (m), 2.3–2.7 (m), 3.1–3.25 (m), 3.3–3.55 (m), 3.65–3.9 (m), 4.1–4.2 (m), 4.45–4.6 (m), 7.1–7.15 (m), 7.3–7.4 (m). Found: C, 50.08; H, 6.61; N, 10.02. C₂₈H₄₈N₅O₃Cl₂S.O.88.CH₂Cl₂.0.5H₂O requires C, 50.70; H, 6.74; N, 10.24. |
| 5 | 1 | (CH₂)₃ |  | 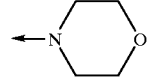 | 480 (m + 1)⁺ | ¹H-NMR (CDCl₃) δ = 0.7–1.3 (m,6H), 1.45–2.1 (m,8H), 2.25–2.3 (m,4H), 2.4–2.55 (m,2H), 2.9–3.1 (m,3H), 3.4–3.75 (m,9H), 7.15–7.2 (m,1H), 7.35–7.4 (m,2H) Found: C, 57.03; H, 7.33; N, 6.94.C₂₅H₃₅N₃O₂Cl.0.63CH₂Cl₂.0.5H₂O requires C, 56.72; H, 6.92; N, 7.75. |
| 6 | 1 | (CH₂)₃ |  | 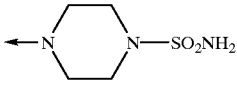 | 558 (m + 1)⁺ | |
| 7 | 0 | (CH₂)₂ | 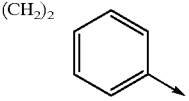 | 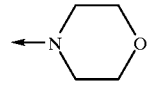 | 488 (m + 1)⁺ | ¹H-NMR-(CDCl₃): δ = 1.45–1.95 (m,br.) 2.6–2.95 (m,br), 3.25–4.0 (m,br.), 6.9–7.55 (m,br.). Found: C, 63.25; H, 6.56; N, 8.40. C₂₆H₃₁Cl₂N₃O₂.0.1.CH₂Cl₂ requires C, 63.06; H, 6.32; N, 8.45. |
| 8 | 0 | (CH₂)₂ | 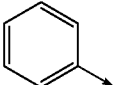 | 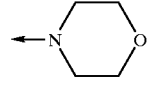 | 518 (m + 1)⁺ | ¹HNMR (CDCl₃) δ : 1.55–1.9 (m), 2.0–2.3 (m), 2.65–2.9 (m), 3.1–4.1 (m), 6.85–7.4 (m). Found: C, 61.52; H, 6.69; N, 7.90. C₂₇H₃₃N₃O₃Cl₂.0.5H₂O requires C, 61.47; H, 6.31; N, 7.96. |

EXAMPLE 9

1-Benzoyl-3-(3,4-dichlorophenyl)-3-(2-[3-morpholinoazetidin-1-yl]ethyl)piperidine

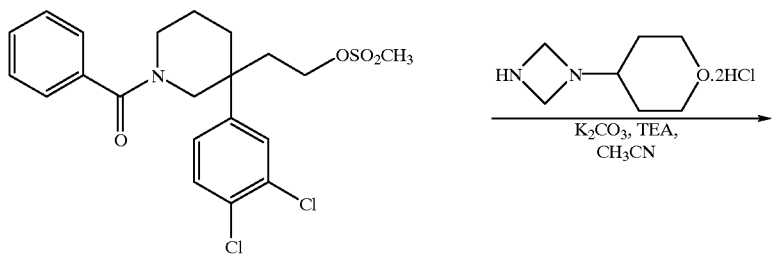

-continued

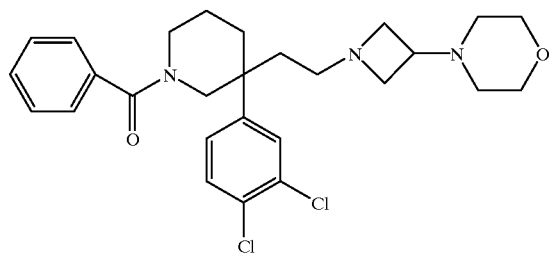

To a solution of the mesylate (see PREPARATION 24) (137 mg, 0.3 mmol.), 3-morpholinoazetidine dihydrochloride (PREPARATION 13) (160 mg, 3 mol. equiv.), triethylamine (0.125 ml, 3 mol.equiv.) and potassium carbonate (83 mg, 2 mol. equiv.) in acetonitrile (5 ml) were added, and the mixture was heated under reflux for four hours. The reaction was cooled to room temperature, water (2 ml) was added and the acetonitrile was removed under reduced pressure. Saturated aqueous sodium bicarbonate (20 ml) and ethyl acetate (20 ml) were then added, and the aqueous phase was extracted with ethyl acetate (3×20 ml). The combined organics were then dried using anhydrous magnesium sulphate, filtered and the solvent was removed under reduced pressure. The residue was chromatographed using silica gel, eluting with a solvent gradient of dichloromethane:methanol (9:1 to 4:1, by volume) to give the title compound (43 mg). $R_f$=0.16 (silica, dichloromethane:methanol, 19:1 by volume). LRMS m/z 502 (m+1)$^+$.

$^1$H-NMR (CDCl$_3$): δ=1.35–1.95 (m, 6H), 2.05–2.15 (m, 2H), 2.25–2.4 (m, 4H), 2.7–2.95 (m, 3H), 3.3–3.6 (m, 5H), 3.65–3.75 (m, 4H), 4.35–4.5 (M, 1H), 7.2–7.5 (m, 8H).

EXAMPLE 10

3-(3,4-Dichlorophenyl)-1-(2-methoxybenzoyl)-3-(2-[3-morpholinoazetidin-1-yl]ethyl)piperidine

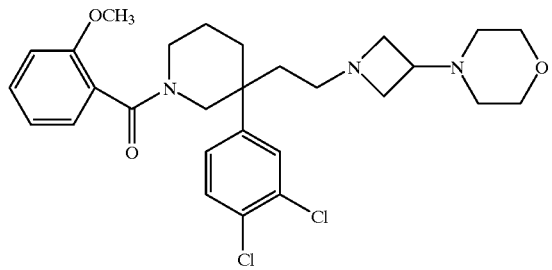

This compound was prepared by a similar method to that used in EXAMPLE 9 using the mesylate as prepared in PREPARATION 25 and 3-morpholinoazetidine dihydrochloride (PREPARATION 13).

LRMS (m/z) 532 (m+1)$^+$.

$^1$HNMR (CDCl$_3$): δ=1.3–2.15 (m, 8H), 2.2–2.4 (m, 5H), 2.7–3.1 (m, 3H), 3.15–4.0 (m, 11H), 4.65–4.7 (m, 1H), 6.8–7.1 (m, 3H), 7.1–7.5 (m, 4H).

EXAMPLE 11

3-(3,4-Dichlorophenyl)-3-(2-[3-morpholinoazetidin-1-yl]ethyl)-1-phenylsulohonylpiperidine

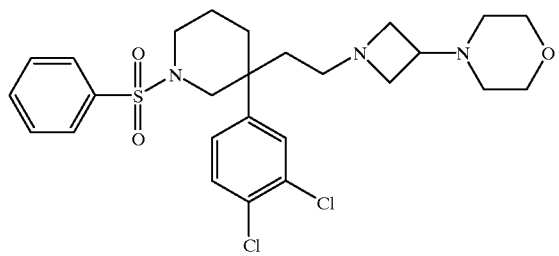

This was prepared by a similar method to that used in EXAMPLE 9 using the mesylate as prepared in PREPARATION 45.

LRMS (m/z) 538 (m+1)$^+$.

Found: C,57.26;H,6.01 ;N,7.97.C$_{26}$H$_{33}$Cl$_2$N$_3$O$_3$S.O.1.CH$_2$Cl$_2$ requires C,57.31 ;H,6.11 ;N,7.68.

$^1$HNMR(CDCl$_3$):δ=1.5–1.9 (m, 6H), 1.95–2.1 (m, 1H), 2.15–2.3 (m, 5H), 2.7–3.0 (m, 5H), 3.1–3.2 (m, 1H), 3.3–3.5 (m, 2H), 3.55–3.75 (m, 5H), 7.2–7.3 (m, 1H), 7.35–7.45 (m, 2H), 7.5–7.65 (m, 3H), 7.7–7.8 (m, 2H).

EXAMPLE 12

3(S)-1-Cyclopropylacetyl-3-(3,4-dichlorophenyl)-3-(2-[3-morpholinoazetidin-1-yl]ethyl)piperidine

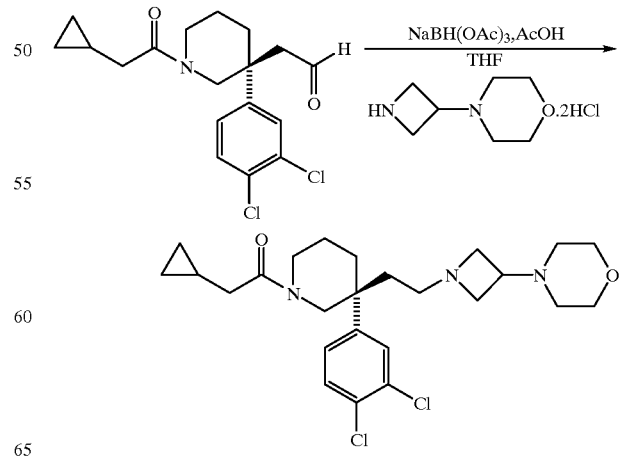

To a solution of the compound of PREPARATION 42 (0.319, 0.88 mmol), 3-morpholinoazetidine dihydrochloride (0.187 g, 1 mol. equiv.) (PREPARATION 13) and triethylamine (0.122 ml, 1 mol. equiv.) in tetrahydrofuran (10 ml), was added sodium triacetoxyborohydride (251 mg, 1.35 mol. equiv.) and glacial acetic acid (0.053 ml, 1 mol. equiv.). The mixture was stirred at room temperature for 64 hours. The mixture was then concentrated to ca. 5 ml and partitioned between ethyl acetate (30 ml) and saturated aqueous sodium bicarbonate solution (20 ml). The organic layer was dried over anhydrous magnesium sulphate, filtered and the solvent was removed under reduced pressure. The residue was purified by flash column chromatography using silica gel, eluting with a solvent gradient of dichloromethane:methanol (92:8 to 9:1 by volume) to give the title compound (220 mg). TLC Rf=0.2 (silica, methanol:dichloromethane 8:92 by volume).

LRMS m/z=480 (m+1)$^+$.

Found: C, 60.78;H, 7.13;N, 7.31. $C_{25}H_{35}N_3Cl_2O_2 \cdot 0.25CH_2Cl_2$ requires C, 60.45;H, 7.3;N, 8.38%.

$^1$H-NMR(CDCl$_3$) δ:0.1–0.2 (m, 2H), 0.5–0.55 (m, 2H), 0.85–0.95 (m, 1H), 1.35–2.3 (m, 14H), 2.65–2.8 (m, 2H), 2.85–2.95 (m, 1 H), 3.2–4.4 (m, 10H), 7.2–7.4 (m, 3H).

EXAMPLE 13

3(S)-1-Cyclopropylacetyl-3-(3,4-dichlorophenyl-3-(2-[3-{4-methanesulphonylpiperazin-1-yl}azetidin-1-yl]ethyl)piperidine

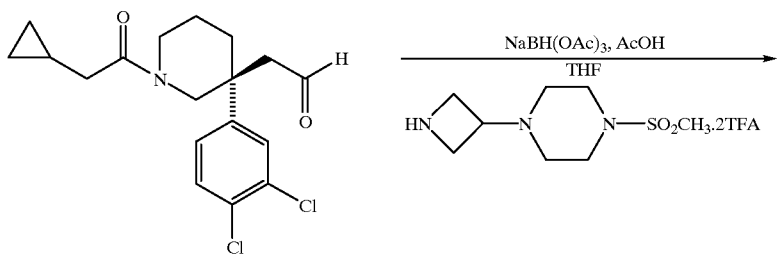

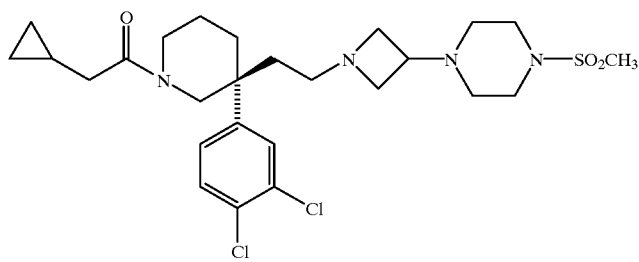

To a solution of the compound of PREPARATION 42 (0.31 g, 0.88 mmol) 3-(4-methanesulphonylpiperazin-1-yl) azetidine bis-trifluoroacetate (0.39 g, 1 mol equiv.) (PREPARATION 46) and triethylamine (0.1 22 ml, 1 mol equiv.) in tetrahydrofuran (10 ml) was added sodium triacetoxyborohydride (186 mg, 1 mol equiv.) and glacial acetic acid (0.053 ml, 1.05 mol equiv.). The mixture was stirred at room temperature for 16 hours. The reaction mixture was then concentrated to ca. 3 ml and partitioned between ethyl acetate (30 ml) and saturated aqueous sodium bicarbonate solution (30 ml). The organic layer was dried over anhydrous magnesium sulphate and filtered. The solvent was removed under reduced pressure to give a residue which was purified by flash column chromatography using silica gel, eluting with dichloromethane:methanol, 10:1 by volume) to give the title compound (375 mg).

TLC Rf=0.35 (silica, dichloromethane:methanol 10:1, by volume).

LRMS m/z=557 (m+1)$^+$.

Found: C, 54.98; H, 6.80; N, 9.40. $C_{28}H_{38}Cl_2N_4O_3S \cdot 0.25CH_2Cl_2$ requires: C,54.63;H,6.72;N, 9.70%.

$^1$H-NMR(CDCl$_3$)δ: 0.05–0.15 (m, 2H), 0.45–0.55 (m, 2H), 0.9–1.0 (m, 1H), 1.4–2.4 (m, 14H), 2.7–3.0 (m, 6H), 3.2–4.4 (m, 10H), 7.2–7.4 (m, 3H).

EXAMPLE 14

3(R)-3-(3-[3-(4-Aminosulphonylpiperazin-1-yl) azetidin-1-yl]propyl)-1-benzoyl-3-(3,4-dichlorophenyl)piperidine

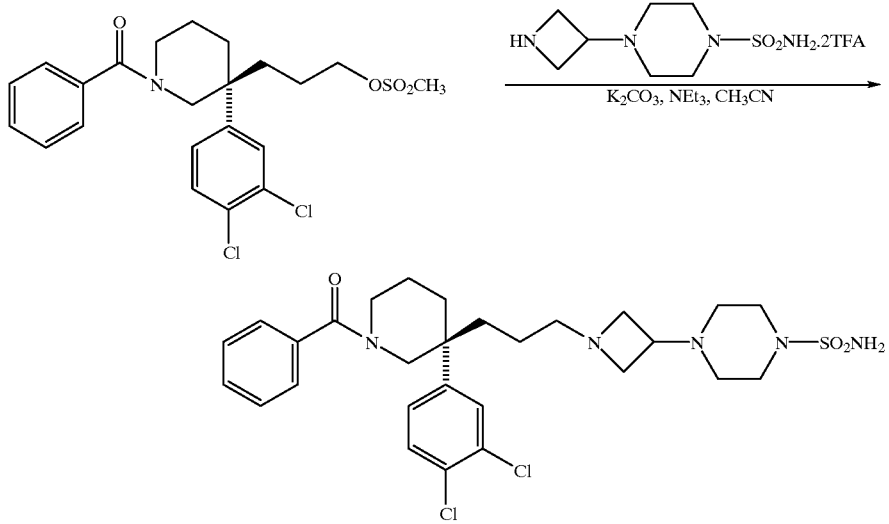

A mixture of the compound of PREPARATION 54 (190 mg, 0.404 mmol.), 1-aminosulphonyl-4-(azetidin-3-yl) piperazine bistrifluoroacetate (PREPARATION 16) (542 mg, 3 mol. equiv.), potassium carbonate (334 mg, 6 mol. equiv.) and triethylamine (0.335 ml, 6 mol equiv.) in acetonitrile (15 ml) were heated under reflux for 8 hours.

The reaction was cooled to room temperature, dichloromethane (50 ml) was added, and the mixture was washed with water (100 ml). The organic layer was dried over anhydrous magnesium sulphate and filtered. The solvent was removed under reduced pressure to give a residue, which was chromatographed on silica gel, eluting with a solvent gradient of ethyl acetate:methanol (9:1 to 3:2, by volume) to give the title compound (19 mg). LRMS (m/z) 515 (m-$SO_2NH_2$)$^+$.

$^1$H-NMR(CDCl$_3$) δ:1.6–1.9 (m, 5H), 2.1–2.2 (m, 1H), 2.25–2.45 (m, 8H), 2.7–2.8 (m, 2H), 2.9–3.0 (m, 1H), 3.2–3.3 (m, 7H), 3.35–3.5 (m, 6H), 4.3–4.4 (m, 1H), 7.25–7.5 (m, 5H).

The following Preparations illustrate the preparation of certain starting materials used in the preceding Examples.

Preparation 1

2-(3,4-Dichlorophenyl)hex-5-enenitrile

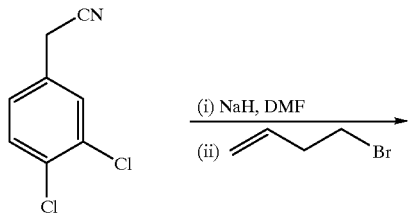

-continued

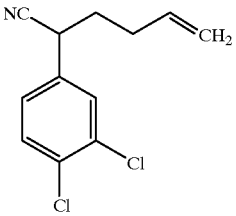

To a solution of sodium hydride (14.8 g, 370.4 mmol, 60% dispersion in mineral oil) in dimethylformamide (150 ml) at 0° C. under nitrogen was added a solution of 3,4-dichlorophenylacetonitrile (68.9 g, 1 mol. equiv.) in dimethylformamide (300 ml), and the mixture was stirred for three hours. A solution of 4-bromobut-1-ene (50 g, 1 mol equiv.) in dimethylformamide (100 ml) was then added, and the mixture was stirred at room temperature for one hour, then heated to 60° C. for five hours.

The reaction mixture was then cooled, and water (11) was added. The mixture was then extracted with ethyl acetate (2×500 ml). The combined organics were then washed with water (2×1 l), dried over anhydrous magnesium sulphate and the solvent was removed under reduced pressure. The residue was then purified by column chromatography using silica gel, eluting with a solvent gradient of ethyl acetate-:hexane (1:19 to 1:6, by volume) to give the title compound (51.5 g). TLC R$_f$=0.47 (silica, hexane:ethyl acetate, 6:1 by volume);

$^1$H-NMR (CDCl$_3$): δ=1.85–2.1 (m, 2H), 2.2–2.3 (m, 2H), 3.75–3.8 (m, 1H), 5.05–5.1 (m, 2H), 5.7–5.8 (m, 1H), 7.15–7.2 (m, 1H), 7.4–7.45 (m, 2H).

Preparation 2

4-Cyano-4-(3,4-dichlorophenyl)-oct-7-enoic acid

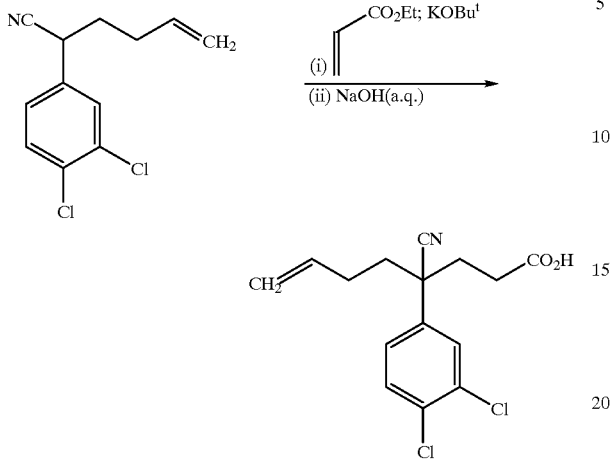

To a solution of the compound of PREPARATION 1 (50.5 g, 210.4 mmol) in dioxan (150 ml) at 0° C. under nitrogen was added potassium tert-butoxide (1.5 g, 0.06 mol. equiv.) and ethyl acrylate (25.4 ml, 1.11 mol. equiv.), and the mixture was stirred for one hour. Aqueous sodium hydroxide solution (2N, 150 ml) was then added and the mixture was stirred at room temperature for seventy minutes.

Methyl tert-butyl ether (300 ml) was then added, and the mixture was acidified to pH1 using aqueous 2N hydrochloride acid solution. The solution was then extracted with methyl tert-butyl ether (2×300 ml), and the combined organics were then dried over anhydrous magnesium sulphate and filtered. Removal of the solvent under reduced pressure gave the title compound (68.12 g), which was used in the next step without further purification.

$^1$H-NMR (CDCl$_3$): δ7 =1.8–2.6 (m, 9H), 4.9–5.0 (m, 2H), 5.65–5.75 (m, 1H), 7.2–7.25 (m, 1H), 7.45–7.5 (m, 2H).

Preparation 3

3-(But-1-en-4-yl)-3-(3,4-dichlorophenyl)-piperidine

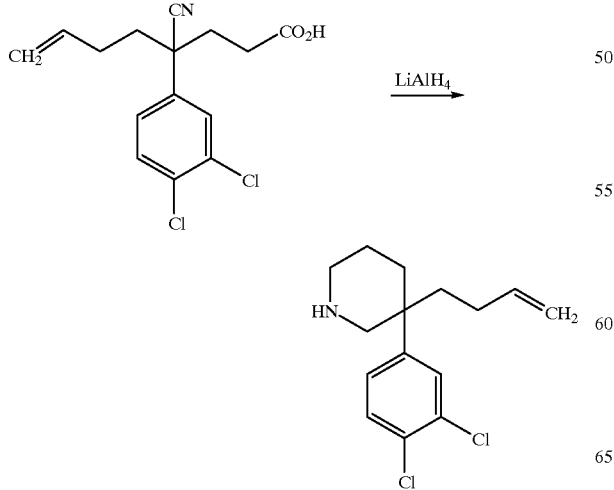

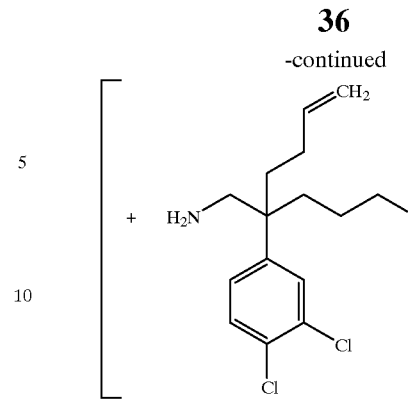

To a solution of lithium aluminium hydride (16.6 g, 2 mol equiv.) in tetrahydrofuran (300 ml) at 0° C. under nitrogen was slowly added a solution of the compound of PREPARATION 2 (68.12 g) in tetrahydrofuran (300 ml), and the reaction was stirred for two hours.

Water (60 ml) was then added carefully, followed by aqueous sodium hydroxide solution (2N, 300 ml). The mixture was then filtered and the solid residue was washed with methyl tert-butyl ether (300 ml). The organic washings were then combined with the filtrate, dried over anhydrous magnesium sulphate, filtered and the solvent was removed under reduced pressure. The residue was then chromatographed using silica gel, eluting with a solvent gradient of methanol ethyl acetate (1:19 to 2:5, by volume) to give the title compound as a mixture with the uncyclised amino-alcohol (19.6 g) which was used in the next step without further purification.

Preparation 4

3-(But-1-en-4-yl)-1-benzoyl-3-(3,4-dichlorophenyl) piperidine

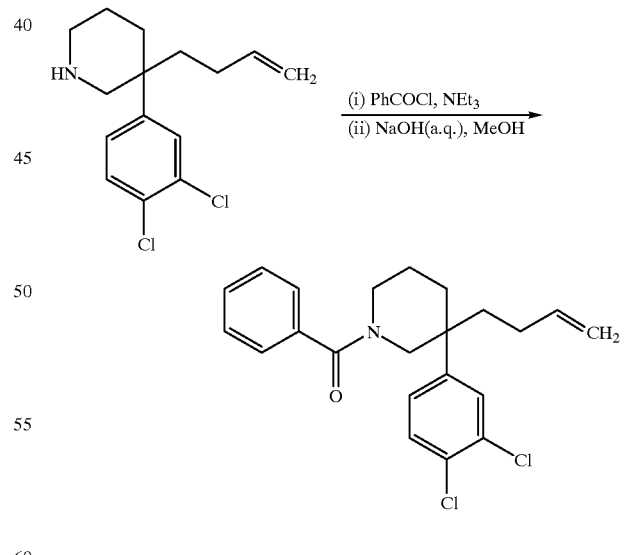

To a solution of the product of PREPARATION 3 (6.02 g) in dichloromethane (70 ml) at 0° C. under nitrogen was added benzoyl chloride (9.37 ml, 4 mol. equiv.) and triethylamine (13.8 ml, 5 mol. equiv.), and the mixture was stirred for 45 minutes.

Dichloromethane (50 ml) was then added, and the mixture was washed with 2N aqueous hydrochloric acid solution (2×100 ml). The organic phase was then dried over anhydrous magnesium sulphate and filtered. The solvent was removed under reduced pressure. A 4% solution of sodium hydroxide in methanol (100 ml) was then added and the mixture was stirred at room temperature for 50 minutes. Dichloromethane (200 ml) was then added, the mixture was washed with water (2×200 ml). The organic phase was dried over anhydrous magnesium sulphate, and then filtered. The solvent was removed under reduced pressure to give a residue. Chromatography using silica gel, eluting with a solvent gradient of ethyl acetate:hexane (1:4 to 3:5, by volume), gave the title compound (3.37 g). TLC $R_f$=0.87 (silica, hexane:ethyl acetate, 3:5 by volume).

LRMS m/z 388 (m+1)$^+$.

$^1$H-NMR (CDCl$_3$): δ=1.3–2.2 (m, 8H), 3.1–3.6 (m, 3H), 1.5–1.7 (m, 1H), 4.85–4.95 (m, 2H), 5.55–5.7 (m, 1H), 7.2–7.55 (m, 8H).

Preparation 5

3-(But-1-en-4-yl)-1-cyclohexanoyl-3-(3,4-dichlorophenyl)piperidine

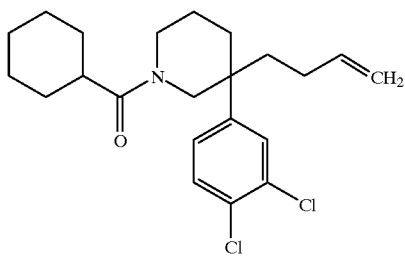

This compound was prepared by the same method as described in PREPARATION 4, using cyclohexanoyl chloride in place of benzoyl chloride.

$^1$H-NMR (CDCl$_3$):=1.1–1.9 (m, 19H), 2.05–2.15 (m, 1H), 2.35–2.5 (m, 1H), 3.1–3.3 (m, 2H), 3.5–3.65 (m, 1H), 4.45–4.5 (m, 1H), 4.8–4.9 (m, 2H), 5.55–5.7 (m, 1H), 7.1–7.15 (m, 1H), 7.3–7.4 (m, 2H).

Preparation 6

3-(But-1-en-4-yl)-1-cyclopropanoyl-3-(3,4-dichlorophenyl)piperidine

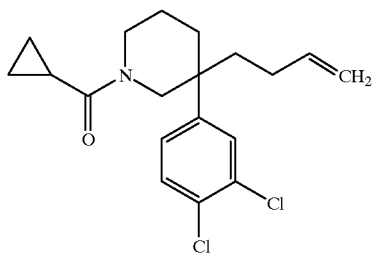

This compound was prepared by the same method as described in PREPARATION 4, using cyclopropanoyl chloride in place of benzoyl chloride.

LRMS m/z 352 (m+1)$^+$.

$^1$H-NMR (CDCl$_3$): δ=0.65–1.1 (m, 4H), 1.4–2.15 (m, 8H), 3.15–3.45 (m, 2H), 3.7–3.9 (m, 2H), 4.35–4.45 (m, 1H), 4.8–4.95 (m, 2H), 5.55–5.7 (m, 1H), 7.1–7.4 (m, 3H).

Preparation 7

1-Benzoyl-3-(3,4-dichlorophenyl)-3-(2-formylethyl)piperidine

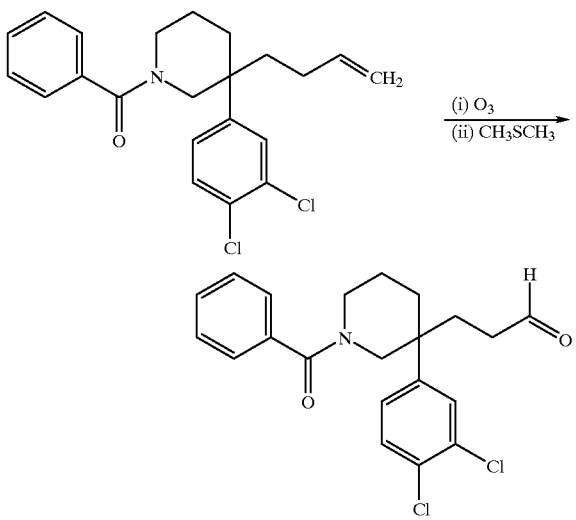

Into a solution of the compound of PREPARATION 4 (3.37 g, 8.7 mmol) in methanol (110 ml) under nitrogen at −78° C. was bubbled ozone at a rate of 50 ml/min. (using a charge of 1.5 A to generate the ozone from oxygen) for ten minutes. After this time the ampage was reduced to zero and oxygen bubbled through the reaction mixture at a rate of 5 ml/min. for ten minutes. The oxygen supply was then removed, and nitrogen was bubbled through the reaction mixture for twenty minutes. After this time a solution of dimethyl sulphide (6.4 ml, 14 mol. equiv.) in methanol (15 ml) was added dropwise, and the reaction was left to warm to room temperature over eighteen hours. The solvent was then removed under reduced pressure and the reaction mixture was partitioned between ethyl acetate (20 ml) and water (15 ml). The organic layer was separated and the aqueous portion was further extracted with ethyl acetate (2×20 ml). The organic layers were then combined, dried using magnesium sulphate, filtered and the solvent was removed under reduced pressure to give the title compound (3.18 g), which was used without further purification.

$^1$H-NMR (CDCl$_3$): δ=1.3–2.1 (m, 6H), 3.15–3.25 (m, 4H), 3.35–3.55 (m, 2H), 7.2–7.45 (m, 8H), 9.6 (s. br., 1H).

Preparations 8.9

The compounds of the general formula:

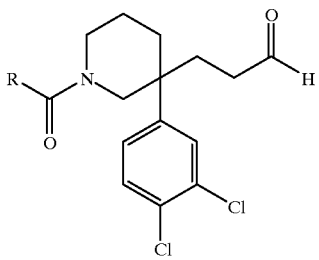

were prepared to a similar method to that used in PREPARATION 7, using the compounds of PREPARATIONS 5 AND 6 respectively.

| Preparation number | R | LRMS m/z | ¹H-NMR (CDCl₃) |
|---|---|---|---|
| 8 | 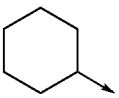 | 396 (m + 1)⁺ | δ = 1.15–1.9 (m, 17H), 1.95–2.1 (m, 1H), 2.3–2.45 (m, 1H), 3.3–3.55 (m, 3H), 4.1–4.3 (m, 1H), 7.15–7.2 (m, 1H), 7.35–7.4 (m, 2H), 9.6 (s, 1H). |
| 9 |  | 354 (m + 1)⁺ | δ = 0.7–0.85 (m, 2H), 0.9–1.05 (m, 2H), 1.45–2.1 (m, 8H), 2.25–2.4 (m, 1H), 3.4–3.7 (m, 3H), 4.05–4.2 (m, 1H), 7.15–7.2 (m, 1H), 7.35–7.45 (m, 2H), 9.6 (s, 1H). |

Preparation 10

1-Diphenylmethylazetidin-3-ol

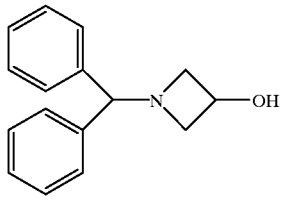

A solution of benzhydrylamine (200 ml, 1.16 mol) and epichlorohydrin (186 ml, 1 mol. equiv.) in methanol (600 ml) was stirred at room temperature for five days and then heated at 40° C. for two days. The solvent was then removed under reduced pressure, the residue dissolved in isopropyl alcohol (500 ml) and the solution heated under reflux for six hours. The solution was cooled to room temperature and the precipitate filtered off. This solid was partitioned between dichloromethane (400 ml) and saturated aqueous sodium bicarbonate solution (500 ml). The aqueous phase was extracted with dichloromethane (2×400 ml) and the combined organic phases dried over magnesium sulphate. The solution was then filtered and the solvent removed from the filtrate under reduced pressure to give the title compound (86 g) as a crystalline solid.

¹H-NMR (CDCl₃): δ=1.8–2.3 (s, br, 1H), 2.85–2.9 (m, 2H), 3.5–3.55 (m, 2H), 4.35 (s, 1H), 4.4–4.5 (m, 1H), 7.15–7.4 (m, 10H).

Preparation 11

1-Diphenylmethyl-3-methanesulphonyloxyazetidine

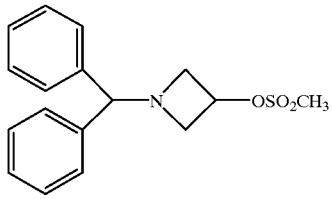

To a solution of 1-diphenylmethylazetidin-3-ol (see Preparation 10) (65.9 g, 275.7 mmol) in dry dichloromethane (700 ml) at 0° C. under nitrogen was added triethylamine (57 ml, 1.2 mol. equiv.). After five minutes, methanesulphonyl chloride (25.6 ml, 1.5 mol. equiv.) was added and the mixture stirred for one hour. Water (300 ml) was then added and the mixture extracted with dichloromethane (3×300 ml). The combined organic layers were dried over magnesium sulphate. The solution was then filtered and the solvent removed from the filtrate under reduced pressure. The residue was chromatographed using silica gel eluting with methanol:dichloromethane (1:49, by volume) to give the title compound (73.4 g) as a solid.

¹H-NMR (CDCl₃): δ=2.95(s, 3H), 3.15–3.25(m, 2H), 3.6–3.65(m, 2H), 4.4(s, 1H), 5.05–5.15(m, 1H), 7.15–7.4(m, 10H).

Preparation 12

1-Diphenylmethyl-3-morpholinoazetidine

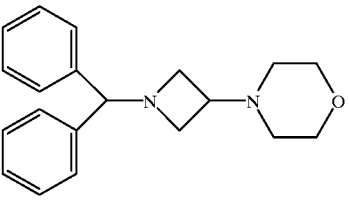

A solution of 1-diphenylmethyl-3-methanesulphonyloxyazetidine (see PREPARATION 11 (24.46 g, 7.72 mmol), potassium carbonate (32 g, 3 mol equiv.) and morpholine (7.34 ml, 1.09 mol. equiv.) in acetonitrile (200 ml) was heated under reflux for four hours. The solution was then cooled to room temperature, water (50 ml) added and the mixture concentrated under reduced pressure. The residue was partitioned between ethyl acetate (400 ml) and water (400 ml) and the organic phase separated and washed with water (2×400 ml). The organic phase was dried over magnesium sulphate, filtered and the solvent removed from the filtrate under reduced pressure. The residue was then chromatographed using silica gel eluting with hexane:diethyl ether (1:1, by volume) to give the title compound (16.5 g).

¹HNMR (CDCl₃: δ=2.25–2.3 (m, 4H), 2.85–3.05 (m, 3H), 3.35–3.4 (m, 2H), 3.7–3.75 (m, 4H), 4.45 (s, 1H), 7.15–7.45 (m, 10H).

Preparation 13

3- Morpholinoazetidine dihydrochloride

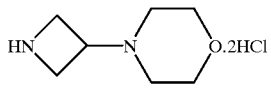

A mixture of 1-diphenylmethyl-3-morpholinoazetidine (see PREPARATION 12) (18.6 g, 60.4 mmol), palladium hydroxide (2 g), ethanol (200 ml) and 1N aqueous hydrochloric acid solution (52 ml) was stirred under an atmosphere of hydrogen at 345 kPa (50 p.s.i.) for three days. The catalyst was then removed by filtration and the filtrate evaporated to dryness. Addition of dichloromethane (100 ml) to the residue and trituration yielded a solid which was recrystallised from methanol to give the title compound (10.2 g) as a crystalline solid.

LRMS m/z 179 (m+1)+.

(N.B. The monohydrochloride, used instead of the dihydrochloride in some reactions, can be similarly prepared using one molar equivalent of hydrogen chloride).

Preparation 14

1-(t-Butoxycarbonyl)-3-(piperazin-1-yl)azetidine

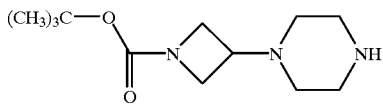

Piperazine (149.2 g, 8 mol. equiv.) was heated to a melt and 1-(t-butoxycarbonyl)-3-methanesulphonyloxy-azetidine (see International Patent Application Publication no. WO93/19059) (54.5 g, 217 mmol) was then added. The mixture was heated at 115° C. for twenty four hours. The reaction was cooled and the excess piperazine removed under reduced pressure. The residue was purified by flash column chromatography on silica gel using methanol:dichloromethane (5:95, by volume) as the eluant to give the title compound (51 g).

LRMS m/z=242 (m+1)+.

$^1$H-NMR (CDCl$_3$): δ=1.4 (m, 9H), 2.5–2.6 (m, 4H), 3.1–3.25 (m, 5H), 3.7–3.8 (m, 2H), 3.9–3.95 (m, 2H), 4.6 (br. s, 1H).

Preparation 15

3-(4-Aminosulphonylpiperazin-1-yl)-1-(t-butoxycarbonyl)azetidine

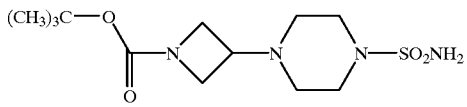

A solution of the compound of PREPARATION 14 (50 g, 132.6 mmol) and sulphamide (88 g, 6.9 mol. equiv.) in 1,4-dioxane (1300 ml) was heated under reflux for fifty five hours. The solution was cooled and the solvent removed under reduced pressure. The residue was purified by flash column chromatography on silica gel using methanol:dichloromethane (5:95, by volume) as the eluant to give the title compound (50 g).

$^1$H-NMR (CDCl$_3$): δ=1.45 (s, 9H), 2.4–2.5 (m, 4H), 3.1–3.2 (m, 1H), 3.25–3.3 (m, 4H), 3.75–3.8 (m, 2H), 3.85–3.9 (m, 2H), 4.3 (br, s, 2H).

Preparation 16

3-(4-Aminosulphonylpiperazin-1-yl)azetidine bistrifluoroacetate

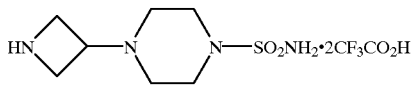

To a solution of the compound of PREPARATION 15 (364 mg, 1.14 mmol) in dichloromethane (6 ml) under an atmosphere of nitrogen at 0° C. was slowly added trifluoroacetic acid (3 ml, 35 mol. equiv.) and the reaction mixture was allowed to warm to room temperature over two hours. The solvent was then removed under reduced pressure and the residue azeotroped with dichloromethane (3×10 ml). The resulting oil was triturated with diethyl ether to give the title compound (379 mg) which was used without further purification.

$^1$H-NMR (CDCl$_3$): δ=2.4–2.6 (m, 4H), 2.95–3.15 (m, 4H), 3.35–3.5 (m, 1H), 3.8–4.1 (m, 4H), 6.6–6.8 (m, 2H), 8.6–8.85 (m, 3H).

Preparation 17

2-(3,4-Dichlorophenyl)-4-(tetrahydropyran-2-yloxy) butanenitrile

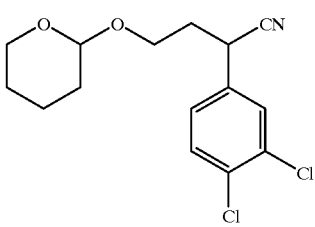

To a mixture of 60% w/w sodium hydride dispersion in oil (19.24 g, 1.05 mol equiv.) in dry tetrahydrofuran (450 ml) at 0° C. under nitrogen was added a solution of 3,4-dichlorophenylacetonitrile (89.5 g, 1 mol. equiv.) in dry tetrahydrofuran (450 ml), dropwise over forty minutes. After a further thirty minutes, a solution of 2-bromoethoxytetrahydropyran (100 g, 1 mol. equiv.) in tetrahydrofuran (100 ml) was added and the mixture allowed to warm to room temperature and stirred for fourteen hours. 30% Aqueous ammonium chloride solution (500 ml) was added and the mixture extracted with diethyl ether (2×400 ml). The organic layers were combined and washed with water (2×400 ml), dried over magnesium sulphate, and the solvent removed under reduced pressure. The residue was then chromatographed using silica gel eluting with a solvent gradient of diethyl ether:hexane (1:9 to 1:1, by volume) to give the title compound (51 g). TLC R$_f$=0.55 (silica, methyl tert-butyl ether:hexane, 1:1, by volume).

LRMS m/z=333 (m+NH$_4$)+.

$^1$H-NMR (CDCl$_3$): δ=1.5–1.9 (m, 6H), 2.05–2.3 (m, 2H), 2.4–2.65 (m, 2H), 2.8–2.95 (m, 2H), 4.0–4.1 (m, 1H), 4.5–4.6 (m, 1H), 7.2–7.25 (m, 1H), 7.25–7.5 (m, 2H).

Preparation 18

Ethyl 4-cyano-4-(3,4-dichlorophenyl)-6-(tetrahydropyran-2-yloxy)hexanoate

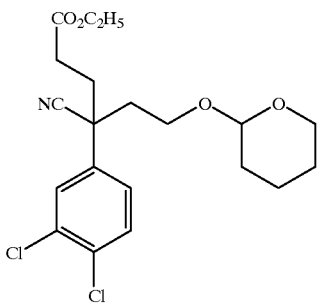

To a solution of diisopropylamine (15 ml, 0.77 mol. equiv.) in tetrahydrofuran (80 ml) at −78° C. under nitrogen was added n-butyllithium (77.3 ml of a 2.5M solution in hexane, 1.4 mol. equiv.) and the solution was then allowed to warm to room temperature over two hours. The solution was cooled to −78° C. and a solution of the compound of PREPARATION 17 (43.9 g, 138 mmol) in tetrahydrofuran (180 ml) was added slowly. The resulting solution was allowed to warm to room temperature slowly over two hours. The solution was then cooled to −78° C. and a solution of ethyl 3-bromopropanoate (22.36 ml, 1.3 mol. equiv.) in tetrahydrofuran (70 ml) added dropwise. Tetra-n-butylammonium iodide (50 g, 1 mol. equiv.) was then added, the reaction allowed to warm to room temperature and stirred for fourteen hours. Water (10 ml) was then added and the solution concentrated under reduced pressure. Water (400 ml) and brine (400 ml) were added and the mixture extracted with ethyl acetate (2×500 ml). The combined organic layers were washed with water (2×300 ml), dried over magnesium sulphate, and the solvent removed under reduced pressure. Chromatography using silica gel eluting with diethyl ether:hexane (1:1, by volume) gave the title compound (35 g).

TLC $R_f$=0.30 (silica, diethyl ether:hexane, 1:1, by volume).

$^1$H-NMR (CDCl$_3$): δ=1.25 (t, 3H), 1.35–1.8 (m, 6H), 2.0–2.55 (m, 6H), 3.3–3.45 (m, 2H), 3.65–3.8 (m, 2H), 4.0–4.1 (m, 2H), 4.4–4.5 (m, 1H), 7.2–7.55 (m, 3H).

Preparation 19

5-(3,4-Dichlorophenyl)-5-(2-[tetrahydropyran-2-yloxy]ethyl)-2(1H)-piperidone

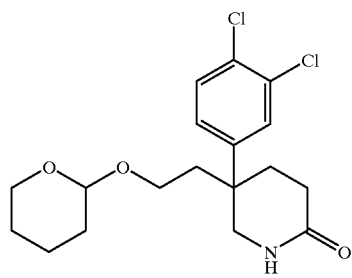

The compound of PREPARATION 18 (18.7 g, 45.2 mmol) was dissolved in saturated ammoniacal ethanol solution (500 ml) which contained Raney nickel (3.5 g). The mixture was stirred under hydrogen at atmospheric pressure for seven hours. The catalyst was then removed by filtration, the ethanol removed under reduced pressure and the residue chromatographed using silica gel eluting initially with diethyl ether and then with methanol:dichloromethane (1:9, by volume) to give the title compound (10.4 g).

TLC $R_f$=0.45 (silica, methanol:dichloromethane, 1:9, by volume).

LRMS m/z=372 (m+1)$^+$.

$^1$H-NMR (CDCl$_3$): δ=1.4–1.8 (m, 6H), 1.9–2.1 (m, 5H), 2.3–2.45 (m, 1H), 3.0–3.2 (m, 1H), 3.35–3.85 (m, 4H), 4.35–4.4 (m, 1H), 6.05), (s, br., 1H), 7.15–7.45 (m, 3H).

Preparations 20 and 21

3-(3,4-Dichlorophenyl)-3-(2-hydroxyethyl)piperidine (Preparation 20) and 3-(3,4-Dichlorophenyl)-3-(2-[tetrahydropyran-2-yloxy]ethyl)piperidine (Preparation 21)

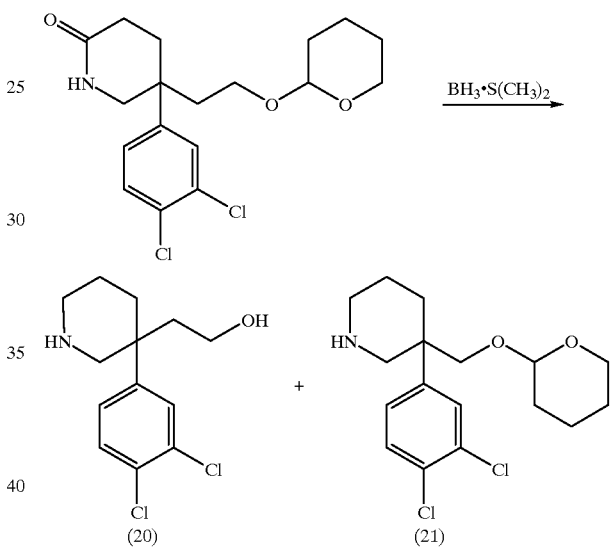

To a solution of 5-(3,4-dichlorophenyl)-5-(2-[tetrahydropyran-2-yloxy]ethyl)-2-(1H)-piperidone (PREPARATION 19) (1.75 g, 4.7 mmol) in tetrahydrofuran at 0° C. under nitrogen was added a solution of borane-dimethyl sulphide complex (2.36 ml, 5 mol. equiv., 10M solution) dropwise. The solution was then slowly warmed to room temperature and then heated under reflux for two hours. The solution was cooled to room temperature and the solvent was then removed under reduced pressure. The residue was then partitioned between dichloromethane (30 ml) and saturated aqueous sodium bicarbonate solution (30 ml). The aqueous phase was extracted with a further portion of dichloromethane (30 ml) and the combined organics dried using anhydrous magnesium sulphate. The solution was then filtered and the solvent was removed under reduced pressure. The residue was purified by column chromatography using silica, eluting with methanol:dichloromethane (1:19, by volume) to give first, the alcohol (20) as the borane-dimethyl sulphide complex and second, the protected alcohol (21) (132 mg). The fractions containing the borane complex of (20) were evaporated under reduced pressure, the residue dissolved in methanol (10 ml) and 2N aqueous hydrochloric acid (10 ml), and the mixture heated under reflux for one hour. The solution was then cooled to room temperature and the solvent was removed under reduced pressure to give the title alcohol (20) (424 mg). Spectral data for (20): LRMS m/z 274 (m+1)$^+$;

$^1$H-NMR (CDCl$_3$): δ=1.45–2.0 (m, 6H), 2.3 (s, br., 2H), 2.7–2.8 (m, 1H), 2.85–2.95 (m, 1H), 3.1 (s, br., 2H), 3.35–3.55 (m, 2H), 7.1–7.2 (m, 1H), 7.35–7.4 (m, 2H).

Spectral data for (21): LRMS m/z 358 (m+1)$^+$;

$^1$H-NMR (CDCl$_3$): δ=1.4–2.1 (m, 12H), 2.8–3.6 (m, 8H), 3.65–3.85 (m, 1H), 4.35 (s, br., 1H), 7.15–7.2 (m, 1H), 7.35–7.5 (m, 2H).

Preparation 22

1-Benzoyl-3-(3,4-dichlorophenyl)-3-(2-hydroxyethyl)piperidine

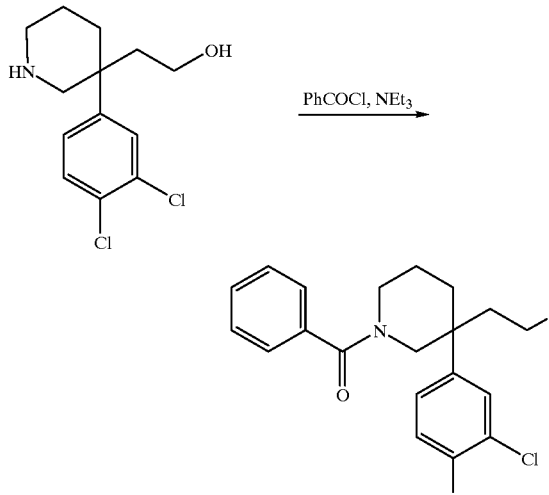

To a solution of the compound of PREPARATION 20 (150 mg, 0.55 mmol) in dichloromethane (5 ml) at 0° C. under nitrogen was added triethylamine (0.114 ml, 1.5 mol. equiv.) and benzoyl chloride (0.076 ml, 1.2 mol. equiv.) and the mixture was stirred at room temperature for one hour. Water (30 ml) and saturated aqueous sodium bicarbonate solution (30 ml) were added and the mixture was extracted with dichloromethane (3×40 ml). The combined organics were then dried using anhydrous magnesium sulphate, filtered and the solvent was removed under reduced pressure, to give the title compound (187 mg), which was used without further purification.

TLC R$_f$=0.34 (silica, dichloromethane:methanol, 19:1 by volume).

LRMS 378 m/z (m+1)$^+$.

$^1$H-NMR (CDCl$_3$): δ=1.4–2.3 (m, 7H), 3.25–4.3 (m, 6H), 7.15–7.6 (m, 8H).

Preparation 23

1-(2-Methoxybenzoyl)-3-(3,4-dichlorobiphenyl)-3-(2-hydroxyethyl)piperidine

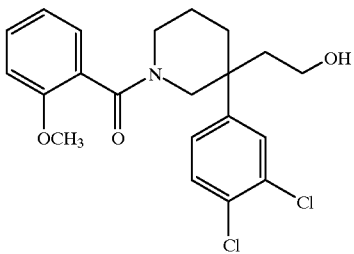

This compound was prepared in a similar method to that used in PREPARATION 22 using the compound prepared in Preparation 20 and 2-methoxybenzoyl chloride in place of benzoyl chloride. The compound was purified by column chromatography (silica, gradient elution, dichloromethane:methanol (49:1 to 24:1, by volume).

LRMS 410 m/z (m+1)$^+$.

$^1$H-NMR (CDCl$_3$): δ=1.35–2.2 (m, 8H), 3.1–4.5 (m, 8H), 6.8–7.1 (m, 2H), 7.2–7.55 (m, 5H).

Preparation 24

1-Benzoyl-3-(3,4-dichlorophenyl)-3-(2-methanesulphonyloxyethyl)piperidine

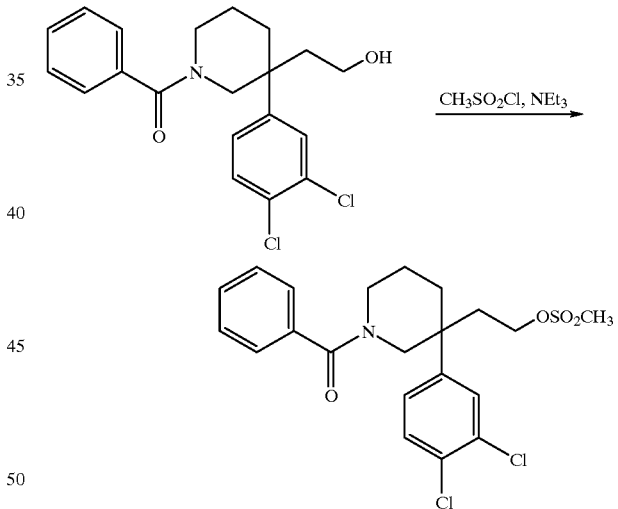

To a solution of the compound of PREPARATION 22 (170 mg, 0.45 mmol) in dichloromethane (4 ml) under nitrogen was added triethylamine (0.094 ml, 1.5 mol. equiv.), and the solution was cooled to 0° C. Methanesulphonyl chloride (0.042 ml, 1.2 mol. equiv.) was then added and the mixture was stirred for one hour. Water (20 ml) was added and the aqueous phase was extracted with dichloromethane (20 ml). The combined organics were then dried over anhydrous magnesium sulphate, filtered and the solvent was removed under reduced pressure. The residue was then chromatographed using silica, eluting with dichloromethane, to give the title compound (145 mg).

TLC R$_f$=0.39 (silica, dichloromethane:methanol, 19:1 by volume).

LRMS 456 m/z (m+1)⁺.

¹H-NMR CDCl₃): δ=1.65 (s, br., 1H), 1.9–2.0 (m, 2H), 2.1 (s, br., 2H), 2.9 (s, br., 2H), 3.35 (s, br., 2H), 3.6–3.75 (m, 1H), 3.9–4.0 (m, 2H), 4.1 (s, br., 1H), 4.3 (s, br., 1H), 7.3–7.5 (m, 8H).

Preparation 25

1-(2-Methoxybenzoyl)-3-(3,4-dichlorophenyl)-3-(2-methanesulphonyloxyethyl)piperidine

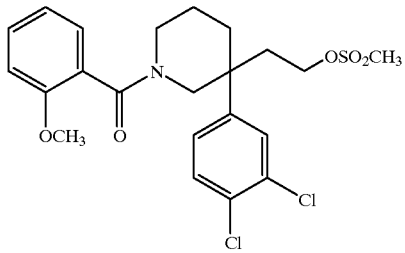

This was prepared in a similar method to that used in PREPARATION 24 using the compound described in PREPARATION 23

LRMS 486 m/z (m+1)⁺.

¹HNMR (CDCl₃): δ=1.4–2.4 (m, 6H), 2.9–4.6 (m, 12H), 6.75–7.6 (7H).

Preparation 27

1-(Phenylsulphonyl)-3-(3,4-dichlorophenyl)-3-([tetrahydropyran-2-yloxy]ethyl)piperidine

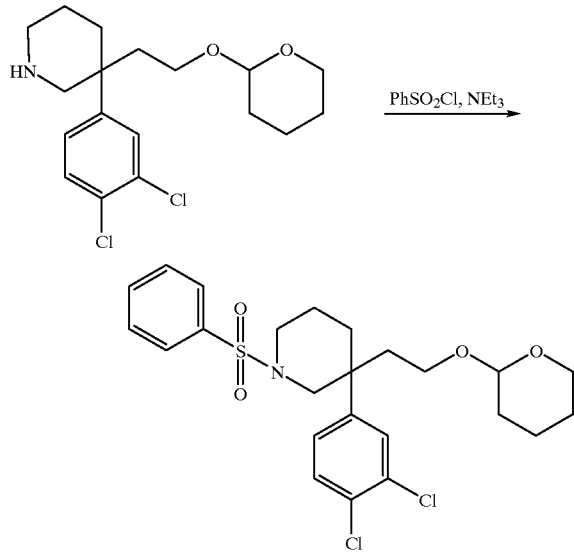

To a solution of the compound of PREPARATION 21 (123 mg, 0.34 mmol) in dichloromethane (3 ml) at 0° C. under nitrogen was added triethylamine (0.06 ml, 1.5 mol. equiv.) and benzenesulphonyl chloride (0.07 ml, 1.2 mol. equiv.). The reaction was stirred for one hour. Water (10 ml) and saturated aqueous sodium bicarbonate (10 ml) were then added and the mixture was extracted with dichloromethane (3×10 ml). The combined organics were then dried over anhydrous magnesium sulphate, filtered and the solvent was removed under reduced pressure to give a gum which was chromatographed, using silica gel eluting with dichloromethane to give the title compound (131 mg).

TLC R$_f$=0.92 (silica, dichloromethane:methanol, 19:1 by volume).

LRMS m/z 515 (m+NH₄)⁺.

¹H-NMR (CDCl₃): δ=1.45–2.05 (m, 12H), 2.55–2.65 (m, 2H), 2.95–3.1 (m, 1H), 3.3–3.55 (m, 3H), 3.7–3.8 (m, 1H), 3.9–4.05 (m, 1H), 4.3–4.4 (m, 1H), 7.3–7.8 (m, 8H).

Preparation 28

1-(Phenylsulphonyl)-3-(3,4-dichlorophenyl)-3-(2-hydroxyethyl)piperidine

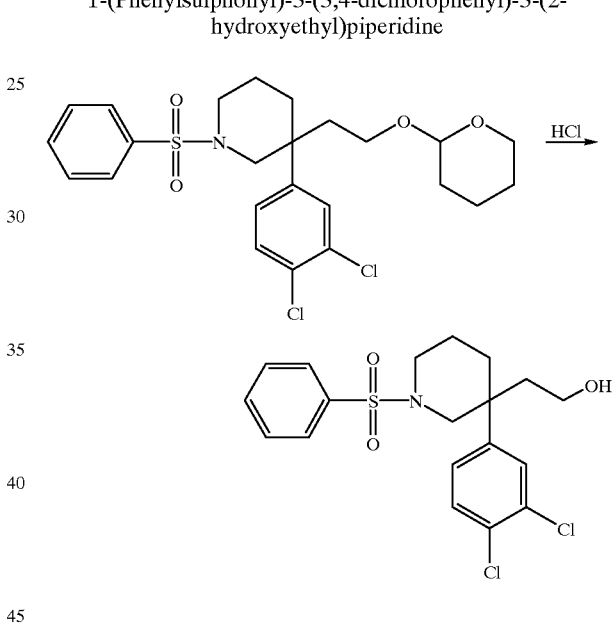

To a saturated solution of hydrogen chloride in methanol (5 ml) at room temperature was added the compound of PREPARATION 27(125 mg), and the mixture was stirred at room temperature for two hours. The solvent was then removed under reduced pressure. Saturated aqueous sodium bicarbonate solution (30 ml) was then added and the aqueous phase was extracted with ethyl acetate (3×30 ml). The combined organics were then dried over anhydrous magnesium sulphate, filtered and the solvent was removed under reduced pressure to give the title compound (155 mg), which was used without further purification. TLC R$_f$=0.45 (silica, dichloromethane:methanol, 19:1 by volume).

LRMS m/z 414 (m+1)⁺.

¹H-NMR (CDCl₃): δ=1.45–2.5 (m, 12H), 2.55–2.65 (m, 2H), 2.95–3.1 (m, 1H), 3.3–3.55 (m, 3H), 3.7–3.8 (m, 1H), 3.9–4.05 (m, 1H), 4.3–4.4 (m, 1H), 7.3–7.8 (m, 8H).

Preparation 29

Ethyl 3-cyano-3-(3,4-dichlorophenyl)-5-(tetrahydropyran-2-yloxy)pentanoate

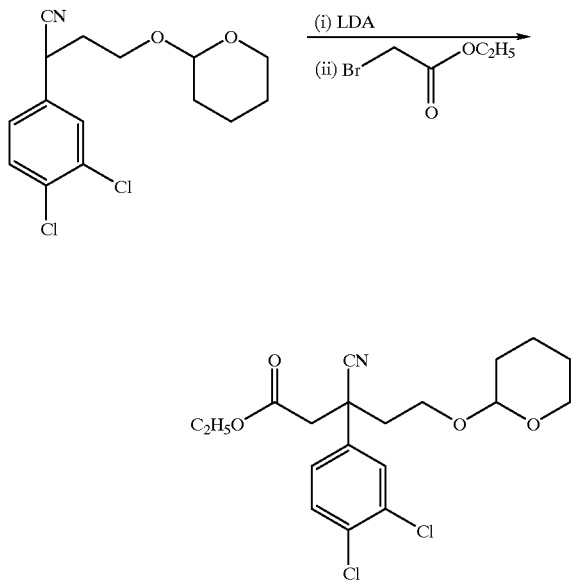

To a solution of diisopropylamine (25.9 ml, 1 mol. equiv.) in tetrahydrofuran (200 ml) at −78° C. under nitrogen was added n-butyllithium (73.9 ml of a 2.5M solution, 1 mol. equiv.). The solution was allowed to warm to room temperature over two hours. A solution of 2-(3,4-dichlorophenyl)-4-(tetrahydropyran-2-yloxy)butanenitrile (PREPARATION 17) (58 g, 158 mmol) in tetrahydrofuran (200 ml) was then added and the solution was stirred for one hour. A solution of ethyl-2-bromoacetate (20.5 ml, 1 mol. equiv.) in tetrahydrofuran (50 ml) was then added and the reaction was heated to reflux for two hours. Water (10 ml) was then added and the solution was concentrated under reduced pressure. Water (300 ml) and brine (300 ml) were added and the mixture was extracted with ethyl acetate (2×300 ml). The combined organic layers were washed with water (2×300 ml), dried over anhydrous magnesium sulphate, filtered and the solvent was removed under reduced pressure. Chromatography using silica gel, eluting with diethyl ether:hexane using gradient elution (4:1 to 1:1 by volume), gave the title compound.

LRMS m/z 417 (m+NH$_4$)$^+$.

$^1$H-NMR (CDCl$_3$): δ=0.85–0.9 (m, 1H), 1.1–1.75 (m, 10H), 2.1–2.3 (m, 1H), 2.35–2.45 (m, 1H), 2.95–3.3 (m, 2H), 3.4–3.55 (m, 1H), 3.7–3.8 (m, 1H), 4.05–4.15 (m, 2H), 4.45 (s, br., 1H), 7.3–7.55 (m, 3H).

Preparation 30

4-(3,4-Dichlorophenyl)-4-(2-[tetrahydropyran-2-yloxy]ethyl)-2-(1H)pyrrolidone

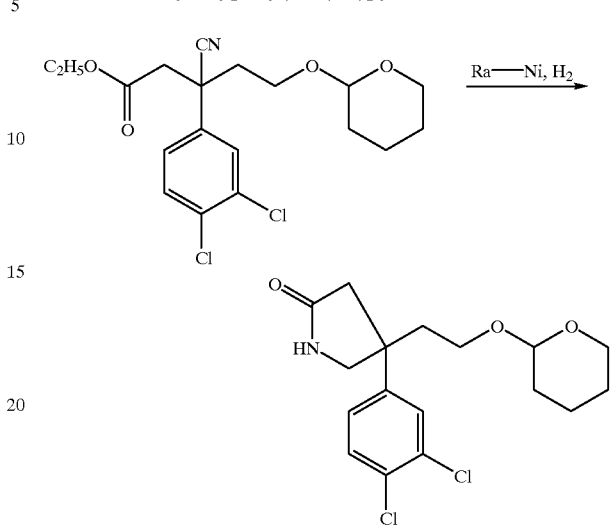

The compound of PREPARATION 29 (9.0 g, 22.5 mmol) was dissolved in saturated ammoniacal ethanol solution (100 ml) which contained Raney nickel (1.0 g). The mixture was stirred under hydrogen at 345 kPa (50 p.s.i.) and 50° C. for two hours and was then allowed to stand under an atmosphere of hydrogen for fourteen hours. A further portion of Raney nickel (0.2 g) was then added, and the reaction mixture was stirred under hydrogen at 345 kPa (50 p.s.i.) and 50° C. for a further three hours. The catalyst was removed by filtration, the ethanol was removed under reduced pressure, and the residue was chromatographed using silica gel, eluting with a solvent gradient of methanol:dichloromethane (1:19 to 1:9, by volume) to give the title compound (6.0 g).

LRMS m/z 358 (m+1)$^+$.

$^1$H-NMR (CDCl$_3$): δ=1.4–1.8 (m, 6H), 2.05–2.2 (m, 2H), 2.7–2.75 (m, 2H), 3.1–3.2 (m, 1H), 3.4–3.5 (m, 1H), 3.55–3.7 (m, 4H), 4.4 (s, br., 1H), 5.9 (s, br., 1H), 7.0–7.05 (m, 1H), 7.25–7.4 (m, 2H).

Preparation 31

3-(3,4-Dichlorophenyl)-3-(2-[tetrahydropyran-2-yloxy]ethyl)pyrrolidine

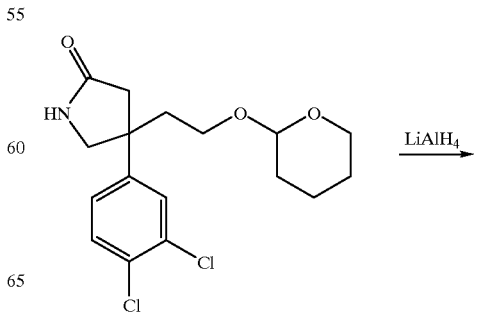

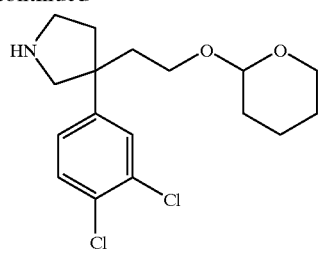

To a solution of lithium aluminium hydride (100 mg, 2 mol equiv.) in dry diethyl ether (20 ml) at 0° C. under nitrogen was added a solution of the compound of PREPARATION 30 (0.5 g, 1.4 mmol) in diethyl ether (20 ml), and the mixture was stirred for 24 hours. A further portion of lithium aluminium hydride (50 mg, 1 mol. equiv.) was then added and the reaction was stirred for a further 2 hours. after (0.1 ml) was added, followed by 15% aqueous sodium hydroxide solution (0.1 ml) and water (0.3 ml). The solid was removed by filtration. The filtrate was then concentrated under reduced pressure to give an oil. Chromatography using silica gel, eluting with dichloromethane:methanol:ammonia (94:5:1, by volume) gave the title compound (200 mg).

TLC $R_f$=0.42 (silica, dichloromethane:methanol:ammonia 90:9:1 by volume.

$^1$H-NMR (CDCl$_3$): δ=1.45–1.85 (m, 6H), 1.9–2.25 (m, 6H), 2.95–3.2 (m, 4H), 3.2–3.65 (m, 2H), 3.7–3.8 (m, 1H), 4.35–4.45 (m, 1H), 7.1–7.4 (m, 3H).

Preparation 32

1-Benzoyl-3-(3,4-dichlorophenyl)-3-(2-[tetrahydropyran-2-yloxy]ethyl)pyrrolidine

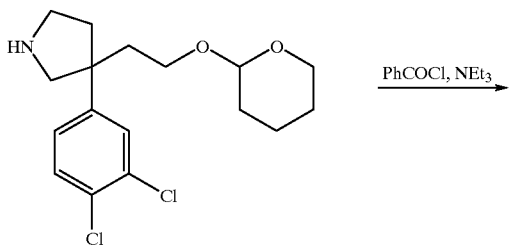

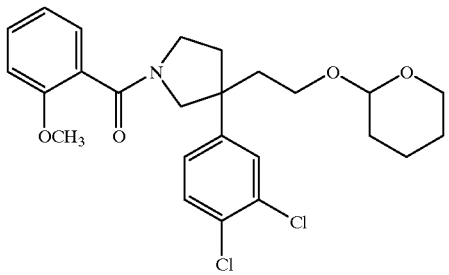

To a solution of the compound of PREPARATION 31 (1.4 g, 4.06 mmol) in dichloromethane (20 ml) was added triethylamine (0.57 ml, 1 mol. equiv.). The solution was then cooled to 0° C. Benzoyl chloride (0.47 ml, 1 mol. equiv.) was added dropwise and the solution stirred at 0° C. for 30 minutes, and then at room temperature for 1 hour. The crude reaction mixture was washed with water (50 ml), and then saturated aqueous sodium bicarbonate solution (50 ml). The organic layer was dried using anhydrous magnesium sulphate, filtered and the solvent was removed under reduced pressure, to give an oil. Chromatography using silica gel, eluting with a solvent gradient of methanol:dichloromethane (1:19 to 1:9, by volume), gave the title compound (1.5 g).

LRMS m/z 448 (m+1)$^+$.

$^1$H-NMR (CDCl$_3$): δ=1.25–2.4 (m, 10H), 3.0–4.4 (m, 9H), 6.9–7.6 (m, 8H).

Preparation 33

1-(2-Methoxybenzoyl-3-(3,4-dichlorophenyl)-3-(2-[tetrahydropyran-2-yloxy]ethyl)pyrrolidine This compound was prepared by a similar method to that used in PREPARATION 32 using the compound prepared in PREPARATION 31 and 2-methoxybenzoylchloride instead of benzoyl chloride.

$^1$H-NMR (CDCl$_3$): δ=1.2–2.25 (m, 10H), 3.05–4.45 (m, 11H), 6.9–7.45 (m, 7H).

Preparation 34

1-Benzoyl-3-(3,4-dichlorophenyl)-3-(2-hydroxyethyl)pyrrolidine

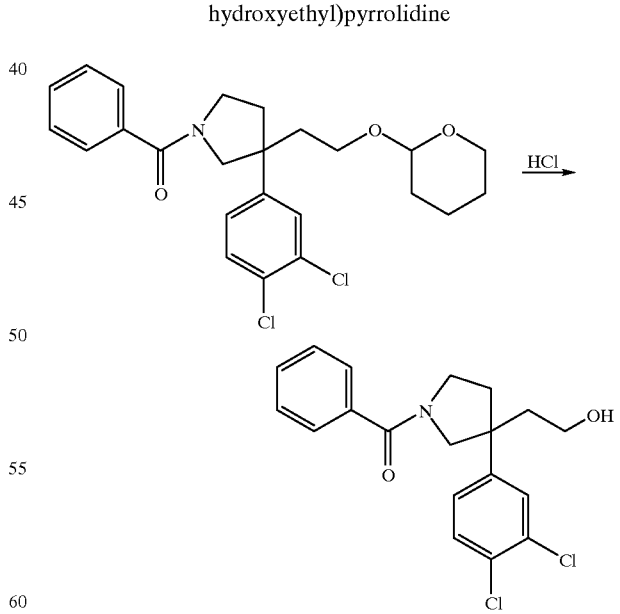

A solution of the compound of PREPARATION 32 (1.5 g, 3.34 mmol) in methanol saturated with hydrogen chloride (50 ml) was stirred at room temperature for one hour. The solvent was then removed under reduced pressure to give the title compound, which was used without further purification.

TLC R$_f$=0.61 (silica, dichloromethane:methanol, 9:1 by volume).

LRMS m/z 364 (m+1)$^+$.

$^1$H-NMR (CDCl$_3$): δ=1.9–2.4 (m, br., 4H), 3.3–4.1 (m, br., 6H), 5.5–5.9 (m, br., 2H), 7.0–7.6 (m, br., 7H).

Preparation 35

1-(2-Methoxybenzoyl-3-(3,4-dichlorophenyl)-3-(2-hydroxyethyl)pyrrolidine

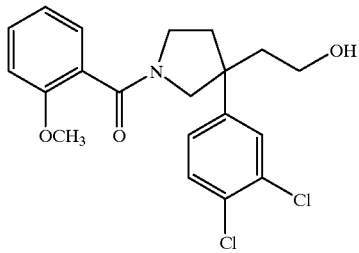

This compound was prepared by a similar method to that used in PREPARATION 34 using the compound prepared in PREPARATION 33.

LRMS m/z 394 (m+1)$^+$.

$^1$H-NMR (CDCl$_3$): δ=1.85–2.3 (m, 4H), 3.15–3.65 (m, 4H), 3.8–4.0 (m, 6H), 6.9–7.45 (m, 7H).

Preparation 36

1-Benzoyl-3-(3,4-dichlorophenyl)-3-(formylmethyl)pyrrolidine

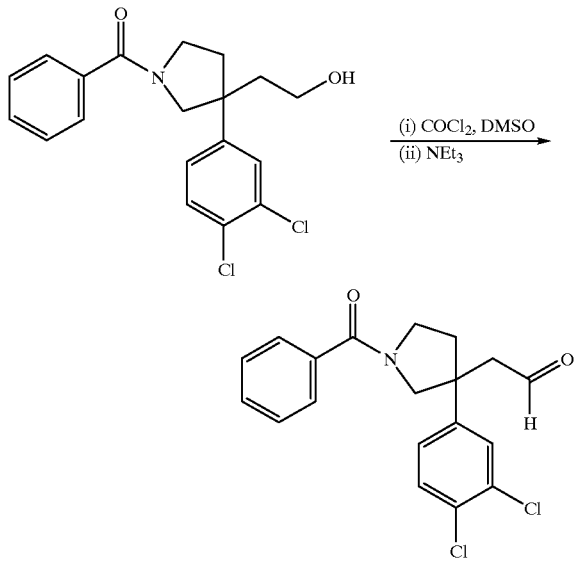

To a solution of oxalyl chloride (0.13 ml, 1.1 mol. equiv.) in dichloromethane (10 ml) at −78° C. under nitrogen was added dimethyl sulphoxide (0.23 ml, 2.4 mol. equiv.) and the solution stirred at −78° C. for forty five minutes. A solution of the compound of PREPARATION 34 (0.5 g, 1.37 mmol) in dichloromethane (10 ml) was added and the reaction was stirred at −78° C. for 1.75 hours. Triethylamine (0.95 ml, 5 mol. equiv.) was added and the reaction was allowed to warm to room temperature, and was stirred for one hour. The mixture was washed with saturated aqueous sodium carbonate solution (50 ml), and dried over magnesium sulphate. The solution was filtered, and the solvent was removed under reduced pressure. The residue was purified by chromatography using silica, eluting with ethyl acetate:methanol (19:1, by volume), to give the title compound (300 mg).

LRMS 362 m/z (m+1)$^+$.

$^1$H-NMR (CDCl$_3$): δ=2.25–2.45 (m), 2.65–2.9 (m), 3.4–4.1(m), 9.45–9.6 (m).

Preparation 37

1-(2-Methoxybenzoyl-3-(3,4-dichlorophenyl)-3-(formylmethyl)pyrrolidine

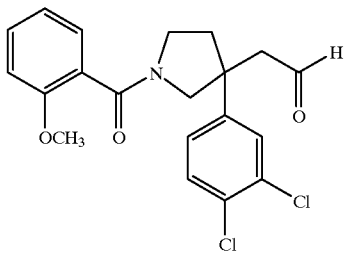

This compound was prepared by a similar method to that used in PREPARATION 36 using the compound prepared in PREPARATION 35.

LRMS m/z 392 (m+1)$^+$.

$^1$H-NMR (CDCl$_3$):δ=2.15–2.35 (m, 2H), 2.7–2.95 (m, 2H), 3.15–3.7 (m, 3H), 3.75–3.9 (m, 3H), 3.95–4.1 (m, 1H), 6.9–7.5 (m, 7H), 9.45–9.55 (m, 1H).

Preparation 38

4(S)-4-Cyano-4-(3,4-dichlorophenyl)-5-(1,3-dioxolan-2-yl)pentan-1-oic acid

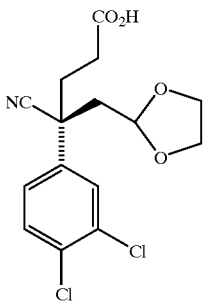

To a 1.0M solution of lithium hexamethyldisilyazide in tetrahydrofuran (4.69 l) at 5° C. under nitrogen was added a solution of 3,4-dichlorophenylacetonitrile (750 g, 4.28 moles) in tetrahydrofuran (750 ml), dropwise, over 45 minutes. The reaction was allowed to stir for 2 hours. The reaction was cooled again to 5° C. and a solution of 2-bromomethyl-1,3-dioxolane (782 g) in tetrahydrofuran (780 ml) added, dropwise, over fifty minutes. Tetra-n-butylammonium iodide (75 g) was added, portionwise, and the mixture was allowed to warm to room temperature, and was stirred for 14 hours. The reaction was then cooled to 5° C. and a solution of lithium hexamethyldisilylazide in tetrahydrofuran (1.0M, 4.69l) was added dropwise. The mixture was stirred for 5 hours at room temperature. The solution was cooled to 5° C. and a solution of ethyl-3-bromopropanoate (840.5 g) in tetrahydrofuran (840 ml) was added, dropwise, over 50 minutes. The reaction was allowed to stir for 14 hours. The reaction mixture was cooled to 5° C. and 1.5M aqueous sodium hydroxide solution (4.25 l, containing 255 g of sodium hydroxide) was added and the mixture was extracted with ethyl acetate (2×3 l). The combined organics were washed with water (2×5 l). The aqueous phases were combined and acidified to pH1 using 5N aqueous hydrochloric acid solution and then extracted with ethyl acetate (2×3 l).

The combined organic extracts were concentrated under reduced pressure to a concentration of approximately 3 ml/g based on the theoretical yield of the product. Dichloromethane (50 ml) was then added, and the solution was washed with water (100 ml). The organic phase was dried over anhydrous magnesium sulphate, filtered, and the solvent was removed under reduced pressuire, to give the title compound (390 mg), which was used without further purification.

TLC $R_f$=0.28 (silica, hexane:ethyl acetate, 2:3 by volume).

$^1$H-NMR (CDCl$_3$): δ=1.25–4.4 (m, 17H), 7.25–7.55 (m, 8H).

The above experimental procedure was then repeated on an identical scale.

To the combined organic solutions from both reactions was added (S)-(−)-alpha-methylbenzylamine (1.13 kg) and the mixture stirred for 14 hours. The thick slurry was then stirred with cooling in an ice-bath for 2 hours, filtered, the solid washed with ethyl acetate (2×1 l) and then dried under reduced pressure at 35° C. to give 1.85 kg of material. A portion of this material (1.34 kg) was dissolved in a mixture of butanone (2 l) and water (503 ml) that was heated under reflux. A further portion of butanone (4.7 l) was added and the solution was allowed to cool slowly to room temperature overnight. The resulting solid was filtered off, washed with butanone (2×1 l) and dried under reduced pressure at 35° C. for 10 hours to give 563 g of material (93.8% e.e.). A further recrystallisation from butanone/water gave the title compound as a (S)-(−)alpha-methylbenzylamine salt in 99.8% e.e. To a stirred solution of this salt in ethyl acetate and water was added 5N aqueous hydrochloric solution until pH1 was achieved. The mixture was stirred for a further 30 minutes, the layers separated and the aqueous phase extracted with ethyl acetate. The combined organic layers were washed with water and the solvent removed by evaporation under reduced pressure to give the title compound.

$^1$H-NMR (CDCl$_3$): δ=2.05–2.35 (m, 4H), 2.4–2.65 (m, 2H), 3.7–4.0 (m, 4H), 4.75–4.85 (m, 1H), 7.25–7.55 (m, 3H), 9.9 (s, br., 1H, acid).

Preparation 39

5(S)-5-(3,4-Dichlorophenyl)-5-(1,3-dioxolan-2-ylmethyl)-2 (1H)-piperidone

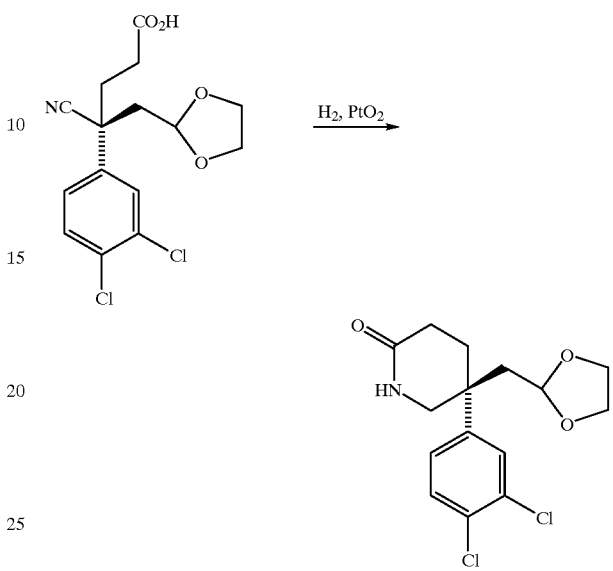

To a solution of the compound of PREPARATION 38 (13.5 g, 39.22 mmol) in glacial acetic acid (130 ml) was added platinum oxide (1.21 g) and the mixture stirred under an atmosphere of hydrogen at 414 kPa (60 psi) and at room temperature for 17 hours. The catalyst was removed by filtration and a further portion of platinum oxide (1.219 g) added. The reaction mixture was then stirred under an atmosphere of hydrogen at 414 kPa (60 psi) and at room temperature for 48 hours. The catalyst was removed by filtration and the solution concentrated under reduced pressure. The residue was dissolved in ethyl acetate (80 ml) and washed with saturated aqueous sodium bicarbonate solution (2×75 ml). The organic phase was then separated and the solvent removed under reduced pressure. The resulting solid was stirred in a solution of hexane (20 ml) and ethyl acetate (20 ml) for 2 hours at 0° C. and then filtered oft to give the title compound (8.15 g).

$^1$H-NMR (CDCl$_3$): δ=1.85–1.95 (m, 1H), 2.0–2.25 (m, 4H), 2.35–2.4 (m, 1H), 3.45–3.55 (m, 1H), 3.65–3.75 (m, 2H), 3.8–3.9 (m, 3H), 4.35–4.4 (m, 1H), 6.15 (s, br., 1H), 7.2–7.45 (m, 3H) ppm.

Preparation 40

3(S)-3-(3,4-Dichlorophenyl)-3-(1,3-dioxolan-2-ylmethyl)piperidine

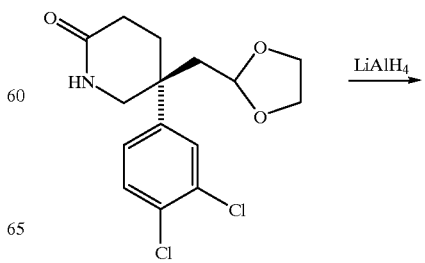

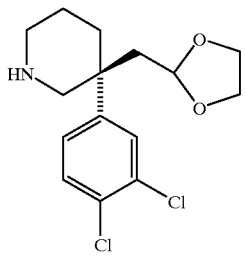

To a stirred solution of lithium aluminium hydride (12.7 ml, 1M solution in tetrahydrofuran, 2.1 mol. equiv.) in tetrahydrofuran (60 ml) under nitrogen was added 5(S)-5-(3,4-dichlorophenyl)-5-(1,3-dioxolan-2-ylmethyl)-2(1H) piperidone (2 g, 6.06 mmole) (PREPARATION 39) in three portions and the mixture heated under reflux for sixteen hours.

Water (0.48 ml) was added dropwise over twenty minutes followed by aqueous sodium hydroxide solution (0.48 ml, 15% solution w/w). After five minutes water (2×0.48 ml) was added and the mixture stirred for thirty minutes).

The mixture was filtered and the solvent was removed from the filtrate under reduced pressure and partitioned between ethyl acetate (100 ml) and saturated aqueous sodium bicarbonate solution (100 ml). The organic layer was dried over anhydrous magnesium sulphate to give an oil, which was then subjected to flash column chromatography using silica gel, eluting with dichloromethane:methanol (9:1), to give the title compound (1.3 g).

$^1$H-NMR (CDCl$_3$): δ=1.4–1.5 (m, 1H), 1.55–1.7 (m, 1H), 1.8–1.9 (m, 1H), 1.95–2.0 (m, 2H), 2.05–2.1 (m, 1H), 2.3 (s, br., 1H), 2.8–2.9 (m, 2H), 3.0–3.1 (m, 1H), 3.3–3.35 (m, 1H), 3.6–3.7 (m, 2H), 3.8–3.9 (m, 2H), 4.3–4.4 (m, 1H), 7.2–7.3 (m, 1H), 7.4–7.5 (m, 2H).

Preparation 41

3(S)-1-Cyclopropylacetyl-3-(3,4-dichlorophenyl)-3-((1,3-dioxolan-2-yl)methyl)piperidine

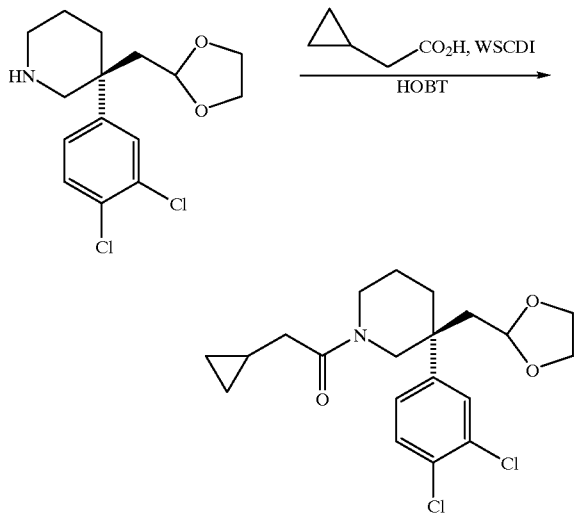

To a solution of the compound of PREPARATION 40 (0.65 g, 2.06 mmole) in dichloromethane (20 ml) at room temperature under nitrogen was added cyclopropyl acetic acid (206 mg, 1 mol. equiv.), N-methyl morpholine (0.23 ml, 1 mol. equiv.), 1-hydroxybenzotriazole hydrate (0.316 g, 1 mol. equiv.) and 1-(3-dimethylaminopropyl)-3-ethyl carbodiimide hydrochloride (0.546 g, 1.4 mol. equiv.). The mixture was stirred for sixteen hours. The mixture was then poured into ethyl acetate (50 ml) and saturated aqueous sodium bicarbonate solution, and the organic phase was separated and dried over anhydrous magnesium sulphate. The solution was filtered, the solvent removed under reduced pressure and the residue was chromatographed using silica gel, eluting with ethyl acetate:hexane (1:1 by volume) to give the title compound (0.7 g).

TLC R$_f$ 0.25 (silica, ethyl acetate:hexane, 1:1, by volume).

LRMS m/z=398 (m+1)$^+$.

$^1$H-NMR (CDCl$_3$): δ=0.05–0.2 (m, 2H), 0.4–0.5 (m, 2H), 0.85–0.95 (m, 1H), 1.35–2.4 (m, 8H), 3.1–4.2 (m, 9H), 4.7–4.75 (m, 1H), 7.2–7.5 (m, 3H).

Preparation 42

3(S)-1-Cyclopropylacetyl-3-(3,4-dichlorophenyl)-3-formylmethyl piperidine

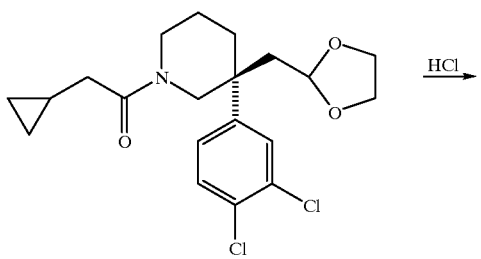

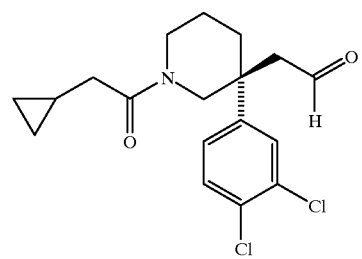

To a solution of the compound of PREPARATION 41 (0.7 g, 1.76 mmol) in tetrahydrofuran (10 ml) was added hydrochloric acid (10 ml, 5N solution), and the mixture was stirred at room temperature for 5 hours. The mixture was then partitioned between ethyl acetate (30 ml) and saturated aqueous sodium bicarbonate solution (30 ml), and the organic phase was dried over anhydrous magnesium sulphate. The solvent was removed under reduced pressure to give the title compound (0.62 g) which was used without any further purification.

$^1$H-NMR (CDCl$_3$): δ=0.1–0.2 (m, 2H), 0.5–0.6 (m, 2H), 0.9–1.0 (m, 1H), 1.6–2.3 (m, 6H), 2.65–2.7 (m, 2H), 3.4–3.5 (m, 2H), 3.8, (d, 1H), 4.05 (d, 1H), 7.3–7.5 (m, 3H), 9.5 (s, 1H).

Preparation 43

1-t-Butoxycarbonyl)-3-(1-piperazinyl)azetidine

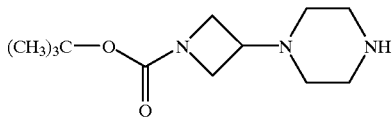

Piperazine (23.69 g, 8 mol. equiv.) was melted and 1-(t-butoxycarbonyl)-3-methanesulphonyloxyazetidine (see International Patent Application Publication no. WO93/19059) (8.64 g, 34.4 mmol) added. The mixture was heated at 120° C. for 15 hours under nitrogen. The reaction was cooled to room temperature and the excess piperazine removed under reduced pressure. The residue was then chromatographed on silica gel using gradient elution (methanol:dichloromethane 1:19 changing to 1:4, by volume) to give the title compound (6.32 g).

LRMS m/z=242 (m+1)$^+$.

$^1$H-NMR (d$_6$-DMSO): δ=1.35 (s, 9H), 2.4–2.5 (m, 4H), 3.0–3.1 (m, 5H), 3.2–4.2 (m, br., 5H).

Preparation 44

1-(t-Butoxycarbonyl)-3-(4-methylsulphonylpiperazin-1-yl)azetidine

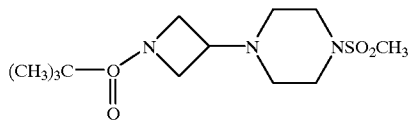

To a solution of the compound of PREPARATION 43 (8.06 g, 21.3 mmol) in dichloromethane (160 ml) was added triethylamine (13.4 ml). The solution was kept under a nitrogen atmosphere and cooled to 0° C. Methanesulphonyl chloride (5.25 ml, 7.77 g, 3 mol. equiv.) was added, dropwise, over 30 minutes. The reaction was allowed to warm to room temperature over 2.5 hours and then stirred for a further 18 hours. The reaction was washed with water (3×50 ml) and then brine (2×30 ml). The organic layer was dried using anhydrous magnesium sulphate. The mixture was then filtered and the solvent removed from the filtrate under reduced pressure. The residue was chromatographed on silica gel eluting with concentrated aqueous ammonia:methanol:dichloromethane (1:10:89, by volume). The product from this chromatography step was then column chromatographed again on silica gel eluting with methanol:ethyl acetate (1:10, by volume) to give the title compound (0.9 g).

TLC R$_f$=0.6 (silica, concentrated aqueous ammonia solution:methanol:dichloromethane, 1:10:89 by volume).

LRMS m/z=320 (m+1)$^+$.

$^1$H-NMR (CDCl$_3$): δ=1.4 (s, 9H), 2.45 (t, 4H), 3.8 (s, 3H), 3.1–3.2 (m, 1H), 3.2–3.3 (m, 4H), 3.75–3.8 (m, 2H), 3.9–4.0 (m, 2H).

Preparation 45

3-(3,4-Dichlorophenyl)-3-(2-methanesulphonyloxyethyl)-1-phenylsulphonylpiperidine

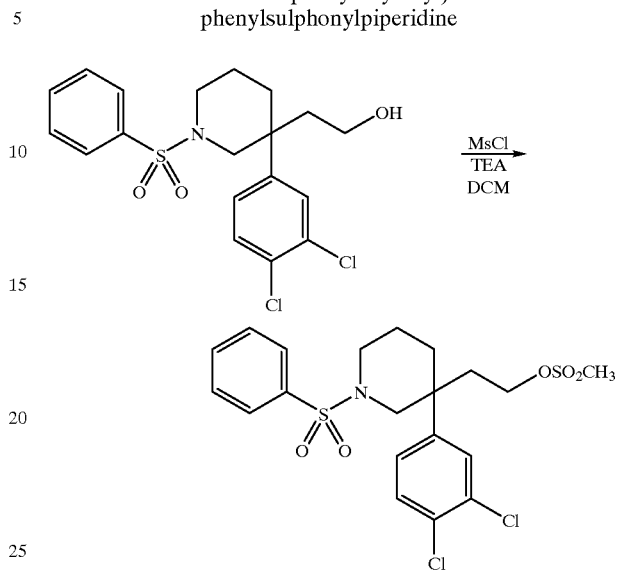

To a solution of the compound of PREPARATION 28 (109 mg, 0.29 mmol) in dichloromethane (4 ml) while under nitrogen at 0° C., was added methanesulphonyl chloride (0.026 ml, 1.2 mol. equiv.). The reaction mixture was stirred at room temperature for one hour. Water (30 ml) and saturated aqueous sodium bicarbonate solution (30 ml) were added, and the mixture was extracted with dichloromethane (3×40 ml). The combined organics were then dried using anhydrous magnesium sulphate, filtered and the solvent removed under reduced pressure. This gave the title compound (106 mg) as a gum which was used without further purification.

TLC Rf=0.89 (silica, methanol:dichloromethane 1:19 by volume)

Preparation 46

3-(4-Methylsulphonylpiperazin-1-yl)azetidine bistrifluoroacetate

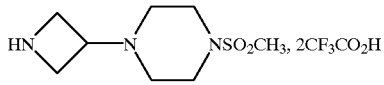

To a solution of the compound of PREPARATION 44 (1.4 g, 5.8 mmol) in dichloromethane (10 ml) at 0° C. under nitrogen was added trifluoroacetic acid (5 ml), dropwise. The mixture was then allowed to warm to room temperature and stirred for one hour. The mixture was concentrated under reduced pressure, the resulting gum washed with diethyl ether, then triturated with diethyl ether and filtered to give the title compound.

LRMS m/z 220 (m+1)$^+$.

$^1$H-NMR (d$_6$-DMSO): δ=2.4–2.5 (m, 2H), 2.9 (s, 3H), 3.1–3.2 (m, 4H), 3.3–3.5 (m, 1H), 3.8–4.0 (m, 4H), 8.7–8.9 (m, 3H).

Preparation 47

2-(3,4-Dichlorophenyl)pent-4-enenitrile

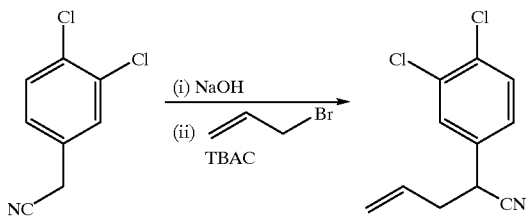

To a stirred solution of 3,4-dichlorophenylacetonitrile (800 g, 4.3 mol) in cyclohexane (16 L) at room temperature was carefully added aqueous sodium hydroxide solution (1600 g of sodium hydroxide in 8 L of water). This addition caused an elevation of the reaction temperature to 50°. Allyl bromide (572 g, 1.1 mol. equiv.) and tetra-n-butylammonium chloride hydrate (40 g, 0.03 mol. equiv.) were then added and the reaction stirred for one hour at 50° C. The aqueous phase was removed and the organic layer washed with water (10 L). The organic phase was filtered through silica gel (1 kg) under reduced pressure to give a yellow filtrate solution. The solvent was removed from the filtrate under reduced pressure to give the title compound as an oil (960 g) of 70% purity which was used without any further purification.

TLC $R_f$=0.71 (silica, diethyl ether:hexane, 1:1, by volume).

LRMS m/z=226 (m+1)$^+$.

$^1$H-NMR (CDCl$_3$): δ=2.6–2.75 (m, 2H), 3.85 (t, 1H), 5.1–5.25 (m, 2H), 5.7–5.9 (m, 1H), 7.2–7.25 (m, 1H), 7.5–7.55 (m, 2H).

Preparation 48

4-Cyano-4-(3,4-dichlorophenyl)hept-6-enoic acid

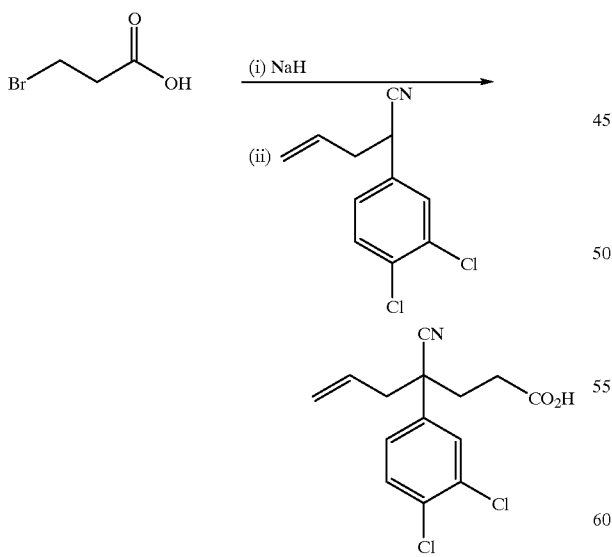

To a stirred suspension of 60% w/w sodium hydride oil dispersion (231 g) in tetrahydrofuran (17 L) under nitrogen at −10° C. was added a solution of 3-bromopropanoic acid (806.5 g) in tetrahydrofuran (6 L) dropwise over three hours. The reaction was allowed to warm to room temperature over 22 hours. The reaction was then cooled to −10° C. Simultaneously, a solution of the compound of PREPARATION 47 (1633.5 G) in tetrahydrofuran (2.5 L) was added dropwise over two hours to a stirred tetrahydrofuran suspension (2.5 L) of 60% w/w sodium hydride oil dispersion (221 g) in tetrahydrofuran (2.5 L) under nitrogen at −10° C. When the addition was complete, this second reaction was allowed to warm to room temperature over eighteen hours. The reaction was then cooled to −10° C. and cannulated into the above 3-bromopropanoic acid sodium salt mixture over 3 hours. The reaction mixture was heated at 50° C. for five hours. The reaction was then cooled, poured into water (8 L) and basified to pH 9.3 using aqueous sodium bicarbonate solution. This mixture was washed with dichloromethane (5×2.5 L), and the aqueous portion acidified to pH 1.0 using concentrated hydrochloric acid. The aqueous solution was extracted with dichloromethane (4×2.5 L), and the organic layers were combined, dried using anhydrous magnesium sulphate, filtered and the filtrate concentrated under reduced pressure to give a yellow oil. This oil was then triturated with hexane (1.5 L) to give the title compound as a cream-coloured solid (1153.3 g) which was used without any further purification.

TLC $R_f$=0.42 (silica, methanol:dichloromethane, 1:9, by volume).

LRMS m/z=316 (m+NH$_4$)$^+$.

$^1$H-NMR (CDCl$_3$): δ=2.15–2.8 (m, 6H), 5.1–5.25 (m, 2H), 5.55–5.7 (m, 1H), 7.2–7.25 (m, 1H), 7.5–7.55 (m, 2H) ppm.

PREPARATION 49

4(S)-4-Cyano-4-(3,4-dichlorophenyl)hept-6-enoic acid (R)-(+)-1-(1-naphthyl)ethylamine salt.

To a solution of the compound of PREPARATION 48 (16 g) in ethyl acetate (50 ml) was added R-(+)-1-(1-naphthyl)ethylamine (4.8 g). The solution was stirred for thirty minutes at room temperature and then the solvent removed under reduced pressure to give a gum. This gum was partially dissolved in hexane:diethyl ether (4:1, by volume, 150 ml) and the sides of the flask scratched to induce crystallisation. The white solid that formed was filtered off and crystallised three times from ethyl acetate to give the title compound (4.9 g).

m.p. 153–154° C.

$[α]_{589}^{25}$ 7.1° (c=0.0012).

$^1$H-NMR (CDCl$_3$): δ=1.6 (d, 3H), 2.0–2.2 (m, 2H), 2.25–2.5 (m, 2H), 2.5–2.7 (m, 2H), 3.8–4.1 (s, br, 3H), 5.0–5.2 (m, 3H), 5.5–5.7 (m, 1H), 7.15–7.25 (m, 1H), 7.4–7.6 (m, 6H), 7.75 (d, 1H), 7.9 (d, 1H), 8.1 (d, 1H).

Preparation 50

4(S)-4-Cyano-4-(3,4-dichlorophenyl)hept-6-enoic acid

To a stirred solution of the compound of PREPARATION 49 (5.5 g) in dichloromethane (100 ml) was added 1N aqueous hydrochloric acid solution (100 ml). The aqueous layer was then removed and the organic portion washed with 1N aqueous hydrochloric acid solution (70 ml). The organic layer was dried using anhydrous magnesium sulphate, filtered, and the filtrate evaporated to dryness under reduced pressure to give the title compound (3.6 g.)

LRMS m/z=316 (m+NH$_4$)$^+$.

¹H-NMR (CDCl₃): δ=2.15–2.8 (m, 6H), 5.1–5.25 (m, 2H), 5.55–5.7 (m, 1H), 7.2–7.25 (m, 1H), 7.5–7.55 (m, 2H).

Preparation 51

3(S)-3-(3,4-Dichlorophenyl)-3-allylpiperidine

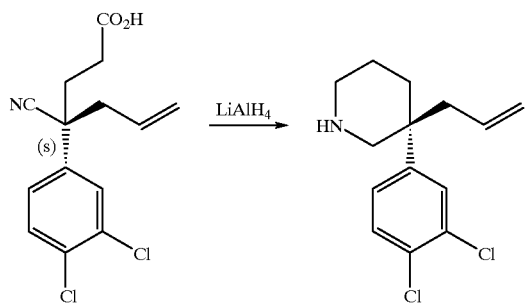

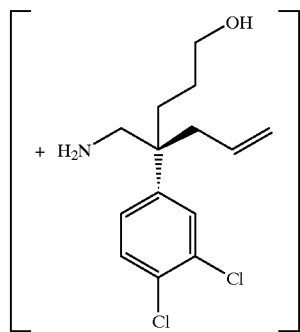

To a mixture of lithium aluminium hydride (867 mg, 2 mol. equiv.) in tetrahydrofuran (30 ml) at 0° C. under nitrogen was added dropwise a solution of 4(S)-4-cyano-4-(3,4-dichlorophenyl)hept-6-enoic acid (3.4 g, 11.41 mol) (PREPARATION 50) in tetrahydrofuran (30 ml). The mixture was stirred for two hours. Water (20 ml) was added carefully followed by aqueous sodium hydroxide solution (2×20 ml). The solid was filtered off and the filter cake was washed with t-butylmethylether (100 ml). The organic phase was then dried over anhydrous magnesium sulphate and filtered. The solvent was removed under reduced pressure. The residue was purified by flash column chromatography using silica gel, using gradient elution (98:2, 19:1, 9:1 ethyl acetate:methanol, by volume) to give (a) the title compound which was contaminated with (b) (S)-4-(aminomethyl)-4-(3,4-dichlorophenyl)-hept-6-en-1-ol (2.55 g), which was used without further purification.

LRMS m/z 270 (m+1)⁺.

Preparation 52

3(S)-1-Benzoyl-3-(3,4-dichlorophenyl)-3-allylpiperidine

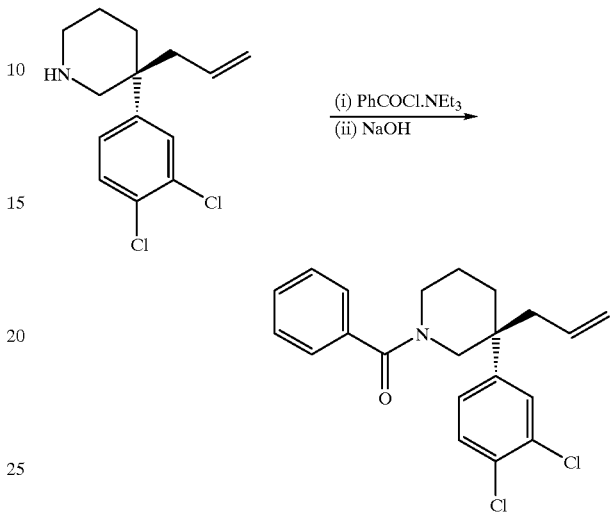

To a solution of the produce of (PREPARATION 51) (2.55 g) in dichloromethane (70 ml) at 0° C. under nitrogen was added triethylamine (3.9 ml) and benzoyl chloride (1.43 ml). The mixture was stirred for 15 minutes.

Dichloromethane (50 ml) was added, the solution was washed with hydrochloric acid (2N, 2×200 ml) and the organic phase dried over anhydrous magnesium sulphate. The solution was filtered and the solvent removed under reduced pressure to give a residue, which was chromatographed on silica gel, eluting with a solvent gradient of hexane:ethyl acetate (9:1 to 1:4, by volume).

This product (2.02 g) was then stirred together with 2% sodium hydroxide in methanol (60 ml) for one hour. Dichloromethane (60 ml) was added, the mixture was washed with water (100 ml) and the organic phase dried over anhydrous magnesium sulphate. The solution was filtered and the solvent was removed under reduced pressure to give a residue. This was chromatographed on silica gel eluting with a solvent gradient of hexane:ethyl acetate (4:1 to 2:3, by volume) to give the title compound (1.24 g).

LRMS m/z 374 (m+1)⁺.

TLC R$_f$=0.59 (silica,hexane:ethyl acetate, 1:1 by volume).

¹H-NMR (CDCl₃) 67 : 1.35–1.7 (m, 2H), 1.8–1.9 (m, 2H), 2.1–2.2 (m, 1H), 2.3–2.5 (m, 2H), 3.2–3.8 (m, 2H), 4.5–4.6 (m, 1H), 4.9–5.1 (m, 2H), 5.4–5.5 (m, 1H), 7.2–7.6 (m, 8H).

Preparation 53

3(S)-1-Benzoyl-3-(3,4-dichlorophenyl)-3-(3-hydroxypropyl)piperidine

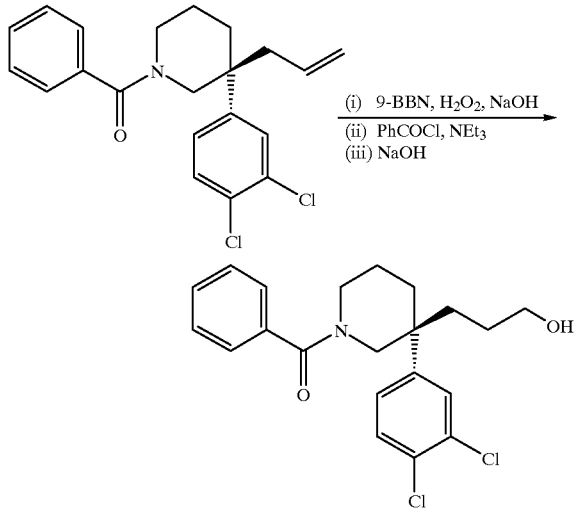

To 9-boracyclo[3.3.1]nonane (22.06 ml, 0.5M solution in tetrahydrofuran) was added a solution of the compound of PREPARATION 52 (825 mg, 2.21 mmol) in tetrahydrofuran (15 ml). The mixture was stirred at room temperature for 90 minutes. Aqueous sodium hydroxide (3.7 ml, 3M solution) and ethanol (7 ml) were then added, and the mixture was cooled in an ice-water bath. Hydrogen peroxide (3.7 ml, 30% w/w aqueous solution) was then added dropwise and the solution was stirred for one hour.

Ethyl acetate (50 ml) was added, the solution was washed with water (2×50 ml) and the organic phase dried over anhydrous magnesium sulphate. The solution was filtered and the solvent removed under reduced pressure. The residue was dissolved in dichloromethane (20 ml) and the solution was cooled in an ice-bath. Triethylamine (1.5 ml, 5 mol. equiv.) and benzoyl chloride (0.65 ml, 2.5 mol. equiv.) were added, and the mixture was stirred for 40 minutes.

Dichloromethane (50 ml) was added and the mixture was washed with aqueous hydrochloric acid (2×50 ml, 2M solution). The organic phase was dried over anhydrous magnesium sulphate, filtered, and the solvent removed under reduced pressure.

The residue was stirred together with 4% sodium hydroxide in methanol solution (50 ml) for one hour. Dichloromethane (60 ml) was added, and the mixture was washed with water (100 ml). The organic phase was dried over anhydrous magnesium sulphate. The solution was filtered and the solvent was removed under reduced pressure to give a residue which was chromatographed on silica gel, eluting with a solvent gradient of hexane:ethyl acetate (4:1 to 1:3, by volume) to give the title compound (320 mg).

LRMS m/z=392 (m+1)$^+$.

TLC $R_f$=0.22 (silica, hexane: ethyl acetate, 2:3 by volume).

$^1$H-NMR (CDCl$_3$): δ31.1–1.3 (m, 1H), 1.4–1.55 (m, 2H), 1.6–1.95 (m, 6H), 2.1–2.2 (m, 1H), 3.3–3.85 (m, 4H), 4.25–4.35 (m, 1H), 7.25–7.5 (m, 8H).

Preparation 54

3(R)-1-Benzoyl-3-(3,4-dichlorophenyl)-3-(3-methane-sulphonyloxypropyl)piperidine

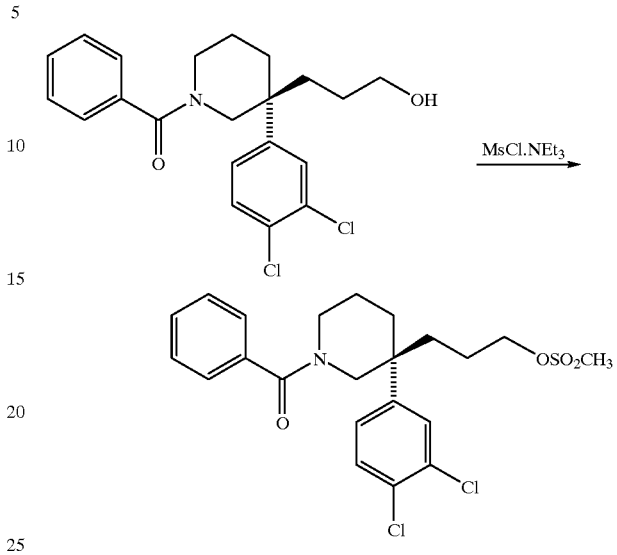

To a solution of the compound of PREPARATION 53 (320 mg, 0.82 mol) in dichloromethane (10 ml) under nitrogen, cooled in an ice-water bath, was added triethylamine (0.34 ml, 3 mol. equiv.) and methanesulphonyl chloride (0.096 ml, 1.5 mol. equiv.). The mixture was stirred for fifteen minutes.

Dichloromethane (50 ml) was then added, and the solution was washed with water (100 ml). The organic phase was dried over anhydrous magnesium sulphate, filtered, and the solvent was removed under reduced pressure, to give the title compound (390 mg), which was used without further purification.

TLC $R_f$=0.28 (silica, hexane:ethyl acetate, 2:3, by volume).

$^1$H-NMR (CDCl$_3$): δ1.25–4.4 (m, 17H), 7.25–7.55 (m, 8H).

Pharmacological Data

The compound of Example 2 was tested for NK$_3$ activity by the method described on page 43 and gave a pIC$_{50}$ of 8.4.

What is claimed is:

1. A compound of the formula:

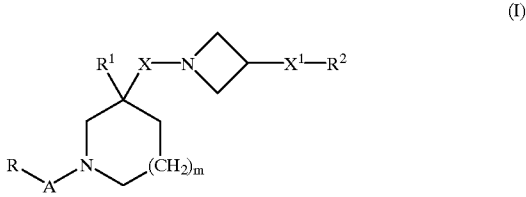

(I)

or a pharmaceutically acceptable salt thereof, wherein

R is C$_3$–C$_7$ cycloalkyl, aryl or C$_1$–C$_6$ alkyl, said C$_1$–C$_6$ alkyl being optionally substituted by fluoro, —COOH, —COO(C$_1$–C$_4$) alkyl, C$_3$–C$_7$ cycloalkyl, adamantyl, aryl or het$^1$, and said C$_3$–C$_7$ cycloalkyl being optionally substituted by 1 or 2 substituents each independently selected from C$_1$–C$_4$ alkyl, C$_3$–C$_7$ cycloalkyl, C$_1$–C$_4$ alkoxy, hydroxy, fluoro, fluoro($C_1$–$C_4$) alkyl and fluoro ($C_1$–$C_4$)alkoxy;

A is CO or $SO_2$;

R is phenyl, benzyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;

$R^2$ is —$CO_2H$, —$CONR^3R^4$, —$CONR^5$($C_3$–$C_7$ cycloalkyl), —$NR^5$($C_2$–$C_5$ alkanoyl), —$NR^3R^4$, —$NR^5CONR^5R^6$, ($C_3$–$C_7$ cycloalkyl-$C_1$–$C_4$ alkyl) $R^5N$—, ($C_3$–$C_7$ cycloalkyl-$C_1$–$C_4$ alkyl)$_2N$—, —$NR^5COCF_3$, —$NR^5SO_2CF_3$, —$NR^5$($SO_2C_1$–$C_4$ alkyl), —$NR^5SO_2NR^5R^6$, —$NR^5$($SO_2$ aryl), —N(aryl)($SO_2C_1$–$C_4$ alkyl), —$OR^5$, —O($C_3$–$C_7$ cycloalkyl), —$SO_2NR^5R^6$, $het^3$ or a group of the formula:

[chemical structures]

$R^3$ and $R^4$ are each independently selected from H and $C_1$–$C_4$ alkyl optionally substituted by hydroxy, $C_1$–$C_4$ alkoxy, —S(O)$_p$($C_1$–$C_4$ alkyl), amino, —NH($C_1$–$C_4$ alkyl), —N($C_1$–$C_4$ alkyl)$_2$ or $het^2$;

$R^5$ and $R^6$ are each independently selected from H, $C_1$–$C_4$ alkyl and $C_3$–$C_7$ cycloalkyl-$C_1$–$C_4$ alkyl, said $C_1$–$C_4$ alkyl and $C_3$–$C_7$ cycloalkyl-$C_1$–$C_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro ($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5$($SO_2C_1$–$C_4$ alkyl), —$NR^5SO_2NR^5R^6$, —$NR^5COO$($C_1$–$C_4$ alkyl), —$NR^5CONR^5R^6$, —$NR^5$($SO_2$morpholino), —$NR^5$($SO_2$ aryl), —N(aryl)($SO_2C_1$–$C_4$ alkyl) or a group of the formula:

[chemical structure]

X is $C_1$–$C_4$ alkylene;

$X^1$ is a direct link or $C_1$–$C_6$ alkylene;

$X^2$ is a direct link, CO, $SO_2$ or $NR^5CO$;

W is methylene, CO, CH(OH), C(OH)$_2$, CH($C_1$–$C_4$ alkoxy), $CHCO_2H$, $CHCO_2$($C_1$–$C_4$ alkyl), $CHCONR^5R^6$, CHF, $CF_2$, CH(azetidin-1-yl), CH(pyrrolidin-1-yl), CH(piperidin-1-yl), CH(morpholino), CH(benzoxazol-2-yl), $CHR^9$, O, S(O)$_p$, $NR^5$, N($C_3$–$C_7$ cycloalkyl), $NSO_2$($C_1$–$C_4$ alkyl), $NSO_2NR^5R^6$, $NSO_2CF_3$, $NSO_2$(morpholino), $NSO_2$(aryl),

[chemical structure]

$NCONR^5R^6$, $NCOR^5$, NCO(aryl) or $NCO_2$($C_1$–$C_4$ alkyl);

$W^1$ is methylene, CO, CH(OH), C(OH)$_2$, CH($C_1$–$C_4$ alkoxy), $CHCO_2H$, $CHCO_2$($C_1$–$C_4$ alkyl), $CHCONR^5R^6$, CHF, $CF_2$, CH(azetidin-1-yl), CH(pyrrolidin-1-yl), CH(piperidin-1-yl), CH(morpholino) or $CHR^9$;

$W^2$ is $W^1$, —$CH_2W^1$—, —$CH_2WCH_2$— or —$CH_2CH_2WCH_2$—;

m is 0, 1 or 2;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R_9$ and W, means naphthyl or phenyl, each optionally substituted by $C_1$–$C_4$ alkyl, halo, —$OR^5$, fluoro($C_1$–$C_4$)alkyl, $C_2$–$C_5$ alkanoyl, —$CONR^5R^6$, —$SO_2NR^5R^6$ or phenyl;

"$het^1$", used in the definition of R, means thienyl or a 5- or 6-membered ring heteroaryl group containing either 1 or 2 nitrogen heteroatoms or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro ($C_1$–$C_4$ alkyl) and fluoro($C_1$–$C_4$ alkoxy);

"$het^2$", used in the definitions of $R^3$ and $R^4$, means a 4- to 7-membered ring, non-aromatic, heterocyclic group containing 1 or 2 heteroatoms each independently selected from nitrogen, oxygen and S(O)$_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —$CONR^5R^6$ or —$SO_2NR^5R^6$ substituent;

and "$het^3$", used in the definition of $R^2$ means an optionally benzo-fused, N-linked, 5-membered ring heteroaryl group containing from 1 to 4 nitrogen heteroatoms, which is optionally substituted, including in the benzo-fused portion, by 1 or 2 substituents each independently selected from $C_1$–$C_4$ alkyl, fluoro and fluoro($C_1$–$C_4$)alkyl.

2. A compound or salt according to claim 1 wherein R is aryl, $C_3$–$C_7$ cycloalkyl optionally substituted by fluoro or $C_1$–$C_6$ alkyl substituted by $C_3$–$C_7$ cycloalkyl.

3. A compound or salt according to any one of the previous claims wherein A is CO.

4. A compound or salt according to any one of the previous claims wherein $R^1$ is phenyl optionally substituted by 1 or 2 halo substituents.

5. A compound or salt according to any one of the previous claims wherein $R^2$ is —$CONR^3R^4$, —$CONR^5$ ($C_3$–$C_7$ cycloalkyl), —$NR^3R^4$, $het^3$ or a group of the formula:

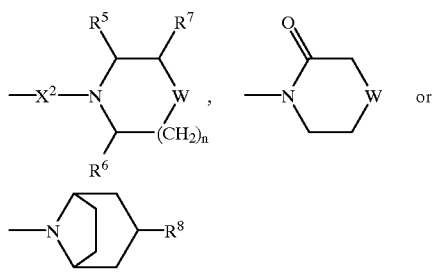

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CHF, CO, CH($C_1$–$C_4$ alkoxy), $CHCO_2H$, $CHCO_2$ ($C_1$–$C_4$ alkyl), CH(benzoxazol-2-yl), $CHNR^5R^6$, $CHNR^5COR^5$, $CHNR^5(SO_2C_1$–$C_4$ alkyl), $CHNR^5COO$ ($C_1$–$C_4$ alkyl), O, $S(O)_p$, $NR^5$, $NSO_2(C_1$–$C_4$ alkyl), $NSO_2NR^5R^6$, $NSO_2$(morpholino), $NCONR^5R^6$, $NCOR^5$, NCO(aryl) or $NCO_2(C_1$–$C_4$ alkyl), n is 1 or 2 when W is other than methylene and is 0 or 1 when W is methylene, and p is 0, 1 or 2.

6. A compound or salt according to any one of the previous claims wherein X is ethylene or propylene.

7. A compound or salt according to any one of the previous claims wherein $X^1$ is a direct link.

8. A compound or salt according to any one of the previous claims wherein $R^2$ is a group of the formula

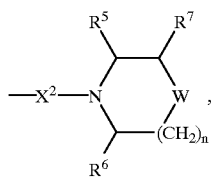

$X^2$ is a direct link, and $R^5$, $R^6$, $R^7$, W and n are as defined in claim 5.

9. A compound or salt according to any one of the previous claims wherein m is 0 or 1.

10. A compound or salt according to any one of the previous claims, which has the stereochemistry shown in formula (IA):

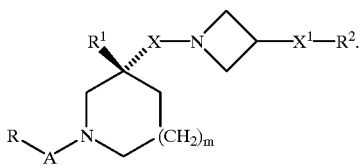

(IA)

11. A compound or salt according to any one of the previous claims wherein:

(i) R is phenyl, A is CO, $R^1$ is 3,4-dichlorophenyl, $R^2$ is morpholino, X is propylene, $X^1$ is a direct link and m is 1;

(ii) R is phenyl, A is CO, $R^1$ is 3,4-dichlorophenyl, $R^2$ is 4-aminosulphonylpiperazin-1-yl, X is propylene, $X^1$ is a direct link and m is 1;

(iii) R is cyclohexyl, A is CO, $R^1$ is 3,4-dichlorophenyl, $R^2$ is morpholino, X is propylene, $X^1$ is a direct link and m is 1;

(iv) R is cyclohexyl, A is CO, $R^1$ is 3,4-dichlorophenyl, $R^2$ is 4-aminosulphonylpiperazin-1-yl, X is propylene, $X^1$ is a direct link and m is 1;

(v) R is cyclopropyl, A is CO, $R^1$ is 3,4-dichlorophenyl, $R^2$ is morpholino, X is propylene, $X^1$ is a direct link and m is 1;

(vi) R is cyclopropyl, A is CO, $R^1$ is 3,4-dichlorophenyl, $R^2$ is 4-aminosulphonylpiperazin-1-yl, X is propylene, $X^1$ is a direct link and m is 1;

(vii) R is phenyl, A is CO, $R^1$ is 3,4-dichlorophenyl, $R^2$ is morpholino, X is ethylene, $X^1$ is a direct link and m is 0;

(viii) R is 2-methoxyphenyl, A is CO, $R^1$ is 3,4-dichlorophenyl, $R^2$ is morpholino, X is ethylene, $X^1$ is a direct link and m is 0;

(ix) R is phenyl, A is CO, $R^1$ is 3,4-dichlorophenyl, $R^2$ is morpholino, X is ethylene, $X^1$ is a direct link and m is 1;

(x) R is 2-methoxyphenyl, A is CO, $R^1$ is 3,4-dichlorophenyl, $R^2$ is morpholino, X is ethylene, $X^1$ is a direct link and m is 1;

(xi) R is phenyl, A is $SO_2$, $R^1$ is 3,4-dichlorophenyl, $R^2$ is morpholino, X is ethylene, $X^1$ is a direct link and m is 1;

(xii) R is cyclopropylmethyl, A is CO, $R^1$ is 3,4-dichlorophenyl, $R^2$ is morpholino, X is ethylene, $X^1$ is a direct link and m is 1; or (xiii) R is cyclopropylmethyl, A is CO, $R^1$ is 3,4-dichlorophenyl, $R^2$ is 4-methanesulphonylpiperazin-1-yl, X is ethylene, $X^1$ is a direct link and m is 1.

12. A pharmaceutical composition comprising a compound or salt according to any one of the previous claims, and a pharmaceutically acceptable diluent or carrier.

13. A method of treating a disease selected from an inflammatory disease, a central nervous system disorder, a gastro-intestinal (GI) disorder, a urogenital tract disorder, chronic obstructive airways disease, an allergy poisoning, a peripheral neuropathy, a cough or acute or chronic pain comprising administering a tachykinin antagonistic amount of a compound of claim 1.

14. A process for the preparation of a compound or salt according to any one of claims 1 to 11, comprising:

(a) where X is ($C_0$–$C_3$ alkylene)$CH_2$—, the methylene group of which is attached to the azetidine nitrogen atom, and R, $R^1$, A, $R^2$, $X^1$ and m are as defined in claim 1, reductive amination using as starting materials a compound of the formula:

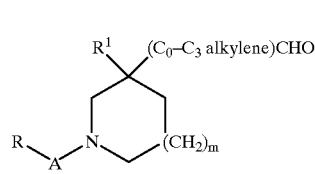

(II)

where R, A, $R_1$ and m are as previously defined for a compound of the formula (I), and a compound of the formula:

(III)

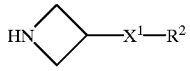

or an acid addition salt thereof, where $R^2$ and $X^1$ are as defined in claim 1;

(b) where X, A, $X^1$, $R^1$, $R^2$ and m are as defined in claim 1, reaction of a compound of the formula (XXII):

(XXII)

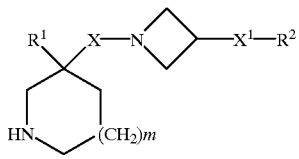

with a compound of the formula R—A—$Z^2$, where R is as defined in claim 1, and R—A—$Z^2$ is $RCO_2H$ or a derivative thereof suitable for acylation of amines, or is $RSO_2Z^2$ suitable for the sulphonylation of amines, where $Z^2$ is a suitable leaving group such as chloro, bromo or iode;

(c) where X, $X^1$, R, A, $R^1$, $R^2$ and m are as defined in claim 1, reaction of a compound of the formula:

(XXIII)

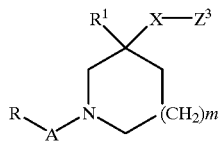

where X, R, A, $R^1$ and m are as defined in claim 1 and $Z^3$ is a suitable leaving group, e.g. chloro, bromo, iodo, methanesulphonyl, trifluoromethanesulphonyloxy or p-toluenesulphonyloxy, with a compound of the formula:

(III)

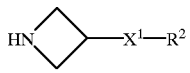

where $R^2$ and $X^1$ is as defined in claim 1;

(d) where $R^1$ is phenyl and X, $X^1$, R, A, $R^2$ and m are as defined in claim 1, hydrogenolysis of a compound of the formula (I) where $R^1$ is phenyl substituted by chloro, bromo or iodo and X, $X^1$, R, $R^2$ and m are as defined in claim 1;

(e) where $R^2$ is a group of the formula:

—$NHR^4$, ($C_3$–$C_7$ cycloalkyl-$C_1$–$C_4$ alkyl)HN—,

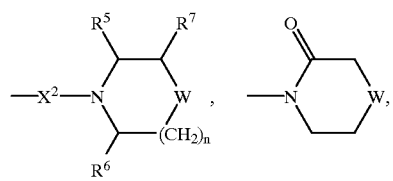

-continued

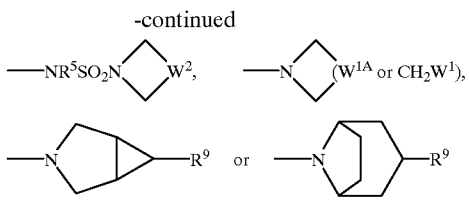

$R^9$ is —$NHR^5$, W is NH or $CHNHR^5$, $W^1$ is $CHNHR^5$, $W^2$ is $W^1$, —$CH_2W^1$—, —$CH_2WCH_2$— or —$CH_2CH_2WCH_2$—, and X, $X^1$, $X^2$, R, $R^1$, $R^5$, $R^6$, $R^7$, m and n are as previously defined for a compound of the formula (I), deprotection of a compound of the formula:

(XXIV)

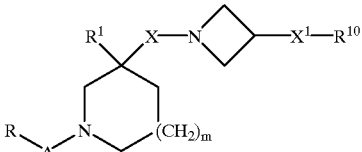

where $R^{10}$ is a group of the formula:

—$NZ^4R^4$, ($C_3$–$C_7$ cycloalkyl-$C_1$–$C_4$ alkyl)$Z^4N$—,

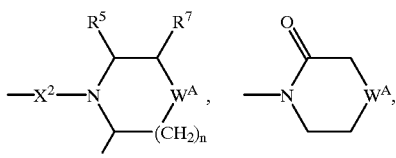

respectively, $R^{9A}$ is —$NZ^4R^5$, $W^A$ is $NZ^4$ or $CHNZ^4R^5$, $W^{1A}$ is $CHNZ^4R^5$, $W^{2A}$ is $W^{1A}$, —$CH_2W^{1A}$, —$CH_2W^ACH^2$— or —$CH_2CH_2W^ACH_2$—, X, $X^1$, $X^2$, R, A, $R^1$, $R^4$, $R^5$, $R^6$, $R^7$, m and n are as previously defined for a compound of the formula (I) and $Z^4$ is a suitable protecting group, e.g. t-butoxycarbonyl or benxyloxycarbonyl;

(f) where $R^2$ is a group of the formula:

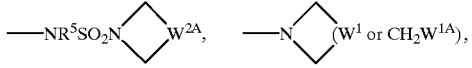

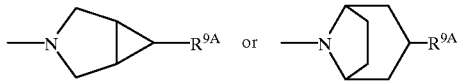

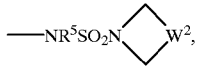

where p is 1 or 2, $W^2$ is —$CH_2S(O)_pCH_2$— or —$CH_2CH_2S(O)_pCH_2$— and X, $X^1$, $X^2$, R, A, $R^1$, $R^5$, $R^6$, $R^7$, m and n are as defined in claim 1, oxidation of a compound of the formula (I) where $R^2$ is a group of the formula:

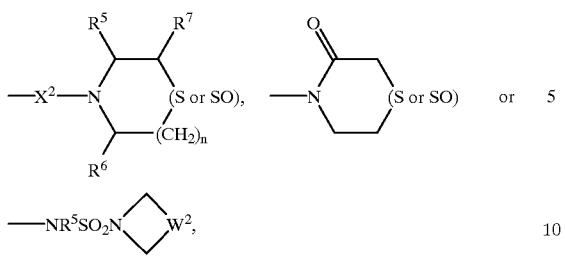

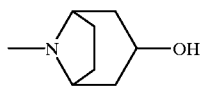

(g) where $R^2$ is a group of the formula:

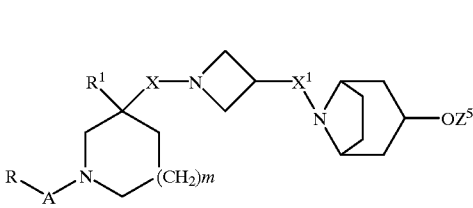

and X, $X^1$, R, A, $R^1$ and m are as defined in claim 1, deprotection of a compound of the formula:

(XXV)

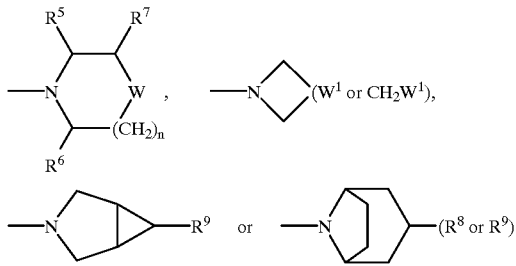

where $Z^5$ is a suitable protecting group (e.g. acetyl or tetrahydropyran-2-yl), and X, $X^1$, R, A, $R^1$ and m are as defined in claim 1;

(h) where $X^1$ is a direct link and $R^2$ is —$NR^3R^4$, ($C_3$–$C_7$ cycloalkyl-$C_1$–$C_4$ alkyl)$R^5N$—, ($C_3$–$C_7$ cycloalkyl-$C_1$–$C_4$ alkyl)$_2N$—, or is a group of the formula:

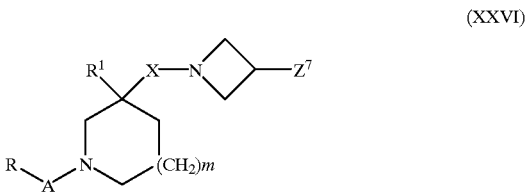

and X, W, $W^1$, R, A, $R^1$, $R^3$, $R^4$, $R^5$, $R^6$, $R^7$, $R^8$, $R^9$, m and n are as defined in claim 1, reaction of a compound of the formula:

(XXVI)

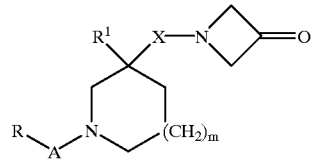

were X, R, A, $R^1$ and m are as defined in claim 1 and $Z^7$ is a suitable leaving group (e.g. methanesulphonyloxy or p-toluenesulphonyloxy), with a compound of the formula:

$HNR^3R^4$, ($C_3$–$C_7$ cycloalkyl-$C_1$–$C_4$ alkyl)$R^5NH$, ($C_3$–$C_7$ cycloalkyl-$C_1$–$C_4$ alkyl)$_2NH$,

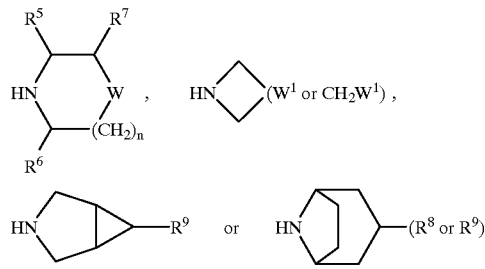

respectively, where W, $W^1$, $R^3$, $R^4$, $R^5$, $R^6$, $R^7$, $R^8$, $R^9$ and n are as defined in claim 1;

(i) where X, $X^1$, R, A, $R^1$, $R^2$ and m are as defined in (h) above, reductive amination using as starting materials a compound of the formula:

(XXVII)

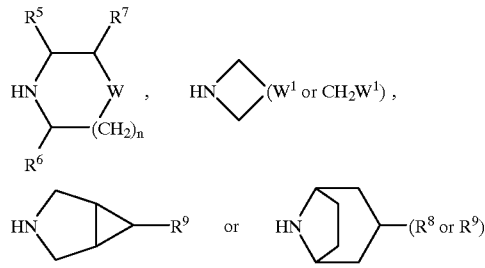

were X, R, A, $R^1$ and m are as defined in claim 1, and a compound of the formula:

$HNR^3R^4$, ($C_3$–$C_7$ cycloalkyl-$C_1$–$C_4$ alkyl)$R^5NH$, ($C_3$–$C_7$ cycloalkyl-$C_1$–$C_4$ alkyl)$_2NH$,

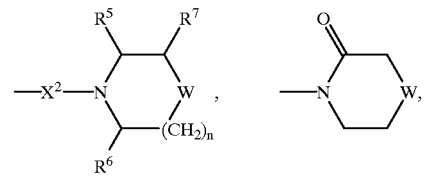

as appropriate, or an acid addition salt thereof, where W, $W^1$, $R^3$, $R^4$, $R^5$, $R^6$, $R^7$, $R^8$, $R^9$ and n are as defined in claim 1;

(j) where $R^2$ is morpholino and X, $X^1$, R, A, $R^1$ and m are as defined in claim 1, reaction of a compound of the formula (I) where $R^2$ is —$NH_2$ and X, $X^1$, R, A, $R^1$ and m are as defined in claim 1, with bis(2-chloroethyl) ether;

(k) derivatisation of certain amine compounds of formula (I), wherein $R^2$ is

—NR⁵SO²N⟨⟩W², —N⟨⟩(W¹ or CH₂W¹),

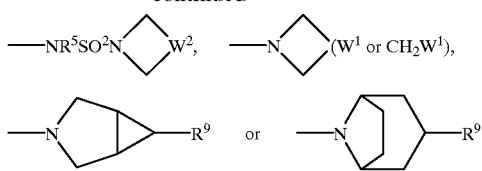

wherein W is NH or CHNHR⁵, W¹ is CHNHR⁵, W² is W¹, —CH₂W¹—, —CH₂WCH₂— or

—CH₂CH₂WCH₂—, or R⁹ is —NHR⁵ and X, X¹, X², R, A, R¹, R⁵, R⁶, R⁷, m and n are as defined in claim 1, to produce (i) a compound of the formula (I) wherein W is NR⁵ or CHNR⁵R⁶, W¹ is CHNR⁵R⁶ or R⁹ is —NHR⁵, or an acid addition salt thereof, as appropriate, wherein R⁵ and R⁶ are as defined in claim 1, with the provisos that R⁵ is not H and it has a methylene group bonded to the nitrogen atom, by reductive amination with an aldehyde of the formula (C₁–C₃ alkyl)-CHO or (C₃–C₇ cycloalkyl-C₁–C₃ alkyl)-CHO, said C₁–C₃ alkyl and C₃–C₇ cycloalkyl-C₁–C₃ alkyl being optionally substituted by fluoro;

(ii) a compound of the formula (I) wherein W is NCONHR⁶ or CHNR⁵CONHR⁶, W¹ is CHNR⁵CONHR⁶ or R⁹ is —NR⁵CONHR⁶, as appropriate, wherein R⁵ and R⁶ are as defined in claim 1, with the proviso that R⁶ is not H, by reaction with an isocyanate of the formula:

R⁶NCO wherein R⁶ is defined in claim 1;

(iii) a compound of the formula (I) wherein W is NSO₂CF₃ or CHNR⁵SO₂CF₃, W¹ is CHNR⁵SO₂CF₃ or R⁹ is —NR⁵SO₂CF₃, as appropriate, wherein R⁵ is as defined in claim 1 by reaction with trifluoromethanesulphonyl chloride or trifluoromethanesulphonic anhydride, optionally in the presence of a suitable acid acceptor, e.g. triethylamine, pyridine or potassium carbonate;

(iv) a compound of the formula (I) wherein W is NSO₂(C₁–C₄ alkyl) NSO₂NR⁵R⁶, NSO₂ (morpholino), NSO₂(aryl) CHNR⁵(SO₂ C₁–C₄ alkyl) or CHNR⁵SO₂NR⁵R⁶, W¹ is CHNR⁵(SO₂ C₁–C₄ alkyl) or CHNR⁵SO₂NR⁵R⁶, or R⁹ is —NR⁵(SO₂ C₁–C₄ alkyl) or —NR⁵SO₂NR⁵R⁶, as appropriate, wherein R⁵ and R⁶ are as defined in claim 1, by reaction with a C₁–C₄ alkanesulphonyl chloride or bromide, a C₁–C₄ alkanesulphonic anhydride or a compound of the formula:

R⁵R⁶NSO₂(Cl or Br), (morpholino)SO₂(Cl or Br) or (aryl)SO₂(Cl or Br), as appropriate, optionally in the presence of a suitable acid acceptor, e.g. triethylamine;

(v) a compound of the formula (I) wherein W is NCOR⁶ or CHNR⁵COR⁶, W¹ is CHNR⁵COR⁶ or R⁹ is —NR⁵COR⁶, as appropriate, wherein R⁵ and R⁶ are as defined in claim 1, with the proviso that R⁶ is not H, by reaction with a compound of the formula:

R⁶CO(Cl or Br) or (R⁶CO)₂O wherein R⁶ is as defined in claim 1, optionally in the presence of a suitable acid acceptor, e.g. triethylamine;

(vi) a compound of the formula (I) wherein W, W¹ or R⁹ is as defined in (v) above, as appropriate, by condensation with a compound of the formula:

R⁶CO₂H wherein R⁶ is as defined in claim 1; or (vii) a compound of the formula (I) where W is NSO₂NR⁵R⁶ or CHNR⁵SO₂NR⁵R⁶, W¹ is CHNR⁵SO₂NR⁵R⁶ or R⁹ is —NR⁵SO₂NR⁵R⁶, as appropriate, wherein R⁵ and R⁶ are as defined in claim 1, by reaction with a compound of the formula:

R⁵R⁶NSO₂NH₂;

(I) wherein R² is:

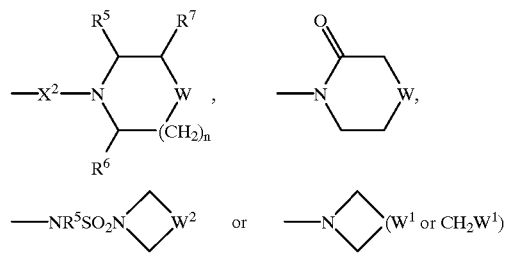

wherein W and W¹ are CHCO₂H and W² is W¹, —CH₂W¹—, —CH₂WCH₂— or —CH₂CH₂WCH₂— and X, X¹, X², A, R, R¹, R², R⁵, R⁶, R⁷, m and n are as defined in claim 1, hydrolysis of a compound of the formula (I) wherein W and W¹ are CHCO₂(C₁–C₄ alkyl), W² is W¹, —CH₂W¹—, —CH₂WCH₂— or —CH₂CH₂WCH₂— and X, X¹, X², A, R, R¹, R², R⁵, R⁶, R⁷, m and n are as defined in claim 1;

(m) wherein R² is

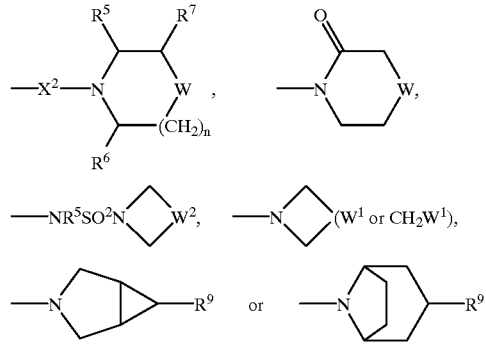

wherein W and W¹ are CHNR⁵R⁶, W² is W¹, —CH₂W¹—, —CH₂WCH₂— or —CH₂CH₂WCH₂—, R⁹ is —NR⁵R⁶ and X, X¹, X², A, R, R¹, R², R⁵, R⁶, R⁷, m and n are as defined in claim 1, reaction of a compound of the formula:

(XXVIII)

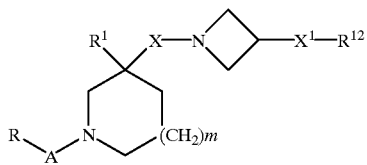

wherein $R^{12}$ is

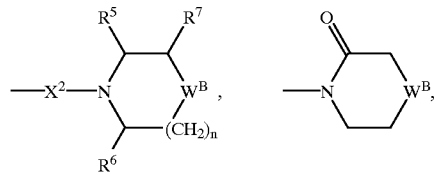

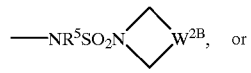

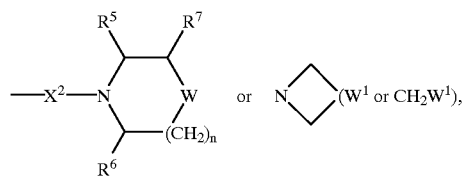

wherein $W^B$ and $W^{1B}$ are $CHZ^8$, $W^{2B}$ is $W^{1B}$, —$CH_2W^{1B}$—, —$CH_2W^BCH_2$— or —$CH_2CH_2W^BCH_2$—, $Z^8$ is a suitable leaving group, (e.g. halo, methanesulphonyloxy, trifluoromethanesulphonyloxy or p-toluenesulphonyloxy), and X, $X^1$, $X^2$, R, A, $R^1$, $R^5$, $R^6$, $R^7$, m and n are as defined in claim 1, with a compound of the formula:

$HNR^5R^6$ wherein $R^5$ and $R^6$ are as defined in claim 1, optionally in the presence of a suitable additional acid acceptor, e.g. triethylamine or potassium carbonate;

(n) wherein $R^2$ is

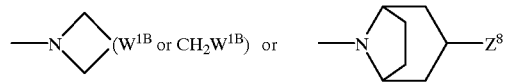

W and $W^1$ are $CHNR^5R^6$ and X, $X^1$, $X^2$, R, A, $R^1$, $R^5$, $R^6$, $R^7$, m and n are defined in claim 1, reductive amination using as the starting materials a compound of the formula (I):

wherein $R^2$ is

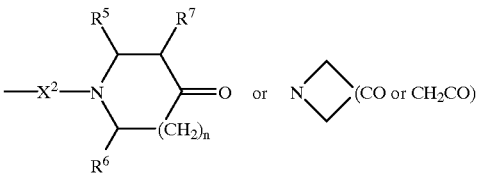

and X, $X^1$, $X^2$, R, A, $R^1$, $R^5$, $R^6$, $R^7$, m and n are as defined in claim 1, and a compound of the formula:

$HNR^5R^6$ wherein $R^5$ and $R^6$ are as defined in claim 1;

(o) intramolecular cyclisation of a compound of the formula:

(XXIX)

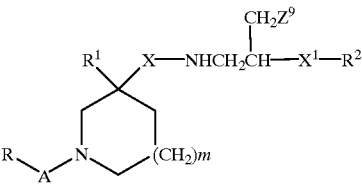

wherein X, $X^1$, R, A, $R^1$, $R^2$ and m are as defined in claim 1 and $Z^9$ is a suitable leaving group (e.g. halo, methanesulphonyloxy or p-toluenesulphonyloxy), optionally in the presence of a suitable acid acceptor, e.g. triethylamine; and/or (p) where A is CO, intramolecular cyclisation of a compound of the formula (XXX):

(XXX)

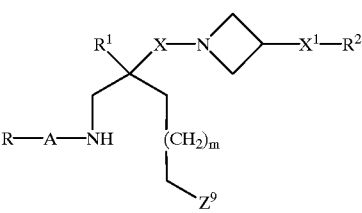

wherein X, $X^1$, R, A, $R^1$, $R^2$ and m are as defined above in method (o), and the reaction is carried out by treatment with a suitable base such as n-butyllithium said process being followed by, optionally, conversion of the compound of formula (I) into a pharmaceutically acceptable salt thereof.

15. A method as in claim 13 there the disease is an inflammatory disease selected from arthritis, psoriasis, asthma or inflammatory bowel disease, a central nervous system disorder selected from anxiety depression, dementia or psychosis, a gastro-intestinal (GI) disorder selected from function bowel disease, irritable bowel syndrome, gastrooesophageal reflux, faecal incontinence or Crohn's disease; a urogenital tract disorder selected from incontinence, hyperreflexia or cystitus, a pulmonary disorder chronic obstructive airways disease, or allergy selected from eczema, contact dermatitis, or rhinitis, poison ivy, a peripheral neuropathy selected from diabetic neuropathy, neuralgia, causalgia, painful neuropathy, a burn, herpetic neuralgia, or post-herpetic neuralgia, a cough or a acute or chronic pain.

16. A compound of formula:

(IIIA)

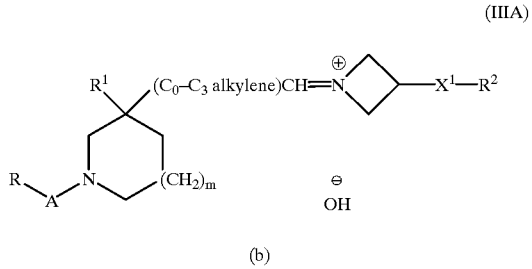

(b)

where R, A, R¹, m, X¹ and R² are as defined in claim 1;

(XXII)

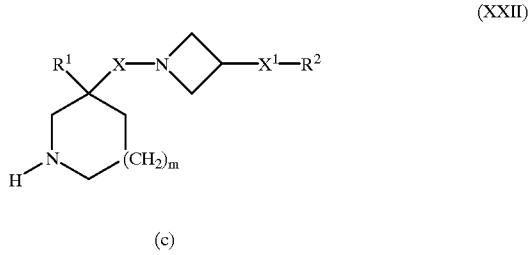

(c)

where R¹, m, X, X¹ and R² are as defined in claim 1;

(XXIV)

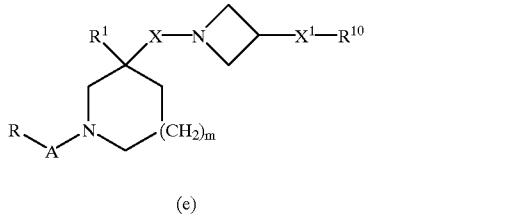

(e)

where R¹⁰ is a group of the formula:

—NZ⁴R⁴, (C₃–C₇ cycloalkyl-C₁–C₄alkyl)Z⁴N—,

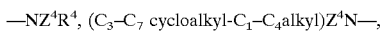

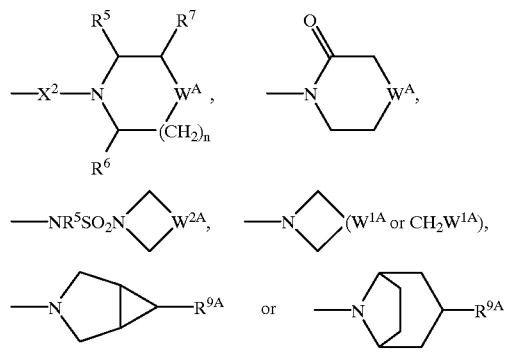

respectively, $R^{9A}$ is —NZ⁴R⁵, $W^A$ is NZ⁴ or CHNZ⁴R⁵, $W^{1A}$ is CHNZ⁴R⁵, $W^{2A}$ is $W^{1A}$, —CH₂$W^{1A}$—, CH₂$W^A$CH₂— or —CH₂CH₂$W^A$CH₂—, X, X¹, X², R, A, R¹, R⁴, R⁵, R⁶, R⁷, m and n are as previously defined for a compound of the formula (I) and Z⁴ is a protecting group, e.g. t-butoxycarbonyl;

(XXV)

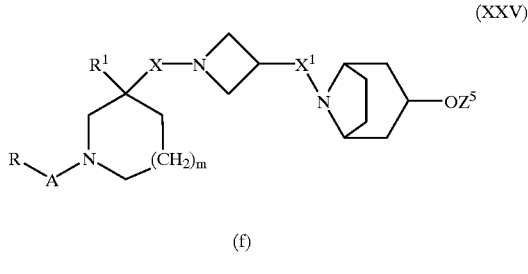

(f)

where Z⁵ is a suitable protecting group, eg. acetyl or tetrahydropyran-2yl, and X, X¹, R, A, R¹ and in are as previously defined in claim 1;

(XXVI)

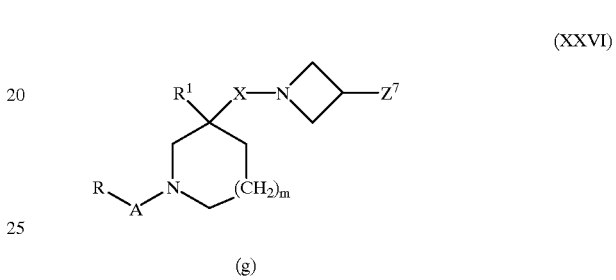

(g)

where X, R, A, R¹ and m are as previously defined in claim 1 and Z⁷ is a leaving group, e.g. methanesulphonyloxy or p-toluene-sulphonyloxy;

(XXVII)

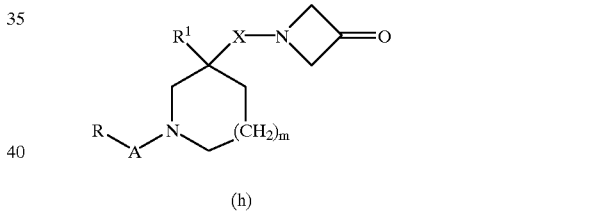

(h)

where X, R, A, R¹ and m are as defined in claim 1;

(XXVIII)

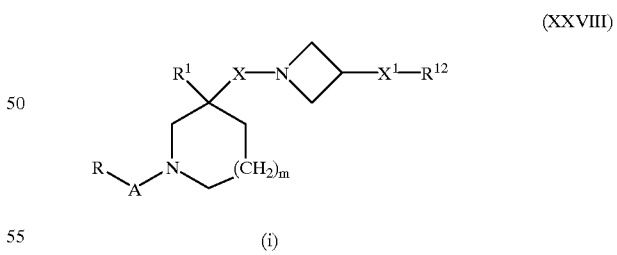

(i)

wherein R¹² is

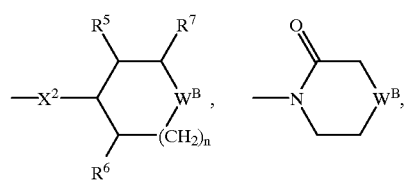

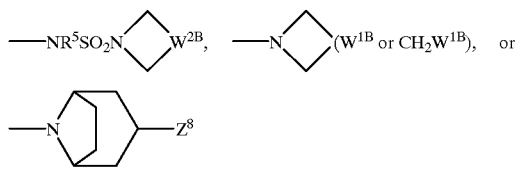

wherein $W^B$ and $W^{1B}$ are $CHZ^8$, $W^{2B}$ is $W^{1B}$, —$CH_2W^{1B}$—, —$CH_2W^BCH_2$— or —$CH_2CH_2W^BCH_2$—, $Z^8$ is a suitable leaving group (e.g. halo, methanesulphonyloxy, trifluoromethanesulphonyloxy or p-toluenesulphonyloxy) and X, $X^1$, $X^2$, R, A, $R^1$, $R^5$, $R^6$, $R^7$, m and n are as defined in claim 1;

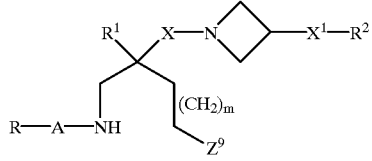

wherein X, $X^1$, R, A, $R^1$, $R^2$ and m are defined in claim 1 and $Z^9$ is as defined above in section (j).

* * * * *